(12) United States Patent
Lee et al.

(10) Patent No.: US 11,427,551 B2
(45) Date of Patent: Aug. 30, 2022

(54) TRIAZINE DERIVATIVE AND PHOTOSENSITIVE COMPOSITION COMPRISING SAME

(71) Applicant: TREEEL CO., LTD, Yongin-si (KR)

(72) Inventors: Gyu Sung Lee, Yongin-si (KR); Bong Seok Moon, Yongin-si (KR); Sung Min Chin, Yongin-si (KR); Ji Soung Kang, Yongin-si (KR); Min Su Ha, Yongin-si (KR); No Gill Park, Yongin-si (KR); Hyun Woo Lee, Yongin-si (KR); Ugun Byun, Yongin-si (KR)

(73) Assignee: TREEEL CO., LTD, Yongin-si (KR)

( * ) Notice: Subject to any disclaimer, the term of this patent is extended or adjusted under 35 U.S.C. 154(b) by 0 days.

(21) Appl. No.: 16/643,250

(22) PCT Filed: Sep. 10, 2018

(86) PCT No.: PCT/KR2018/010549
§ 371 (c)(1),
(2) Date: Feb. 28, 2020

(87) PCT Pub. No.: WO2019/054707
PCT Pub. Date: Mar. 21, 2019

(65) Prior Publication Data
US 2020/0262798 A1    Aug. 20, 2020

(30) Foreign Application Priority Data

Sep. 13, 2017 (KR) .................. 10-2017-0117396
Sep. 7, 2018 (KR) .................. 10-2018-0107042

(51) Int. Cl.
*C07D 251/54* (2006.01)
*C08F 220/68* (2006.01)

(52) U.S. Cl.
CPC .......... *C07D 251/54* (2013.01); *C08F 220/68* (2013.01)

(58) Field of Classification Search
None
See application file for complete search history.

(56) References Cited

U.S. PATENT DOCUMENTS 3,053,812 A * 9/1962 Gaetano .................. C08F 22/00
                                                  526/260
5,597,485 A    1/1997 Mazza et al.
2006/0147847 A1  7/2006 Guire et al.

FOREIGN PATENT DOCUMENTS

| DE | 1810285 A1 | 4/1970 |
|---|---|---|
| JP | S4634897 B | 10/1971 |
| JP | S552611 A | 1/1980 |
| JP | S60155214 A | 8/1985 |
| JP | S626252 A | 1/1987 |
| JP | H02242852 A | 9/1990 |
| JP | H03256048 A | 11/1991 |
| JP | H04110193 A | 4/1992 |
| JP | 2000191729 A | 7/2000 |
| JP | 2002028904 A | 1/2002 |
| JP | 2002075453 A | 3/2002 |
| JP | 2003089759 A | 3/2003 |
| JP | 2008094732 A | 4/2008 |
| JP | 2009215455 A | 9/2009 |
| JP | WO2008053864 A1 | 2/2010 |
| JP | WO2011018990 A1 | 1/2013 |
| KR | 101569344 B1 | 11/2015 |
| KR | 101692343 B1 | 1/2017 |
| KR | 1020170013674 A | 2/2017 |
| KR | 20170049983 A | 5/2017 |

OTHER PUBLICATIONS

Ikkai, F et al. Macromolecular Chemistry and Physics, 2007, 208, 271-276.*
JPWO2011018990 machine translation, downloaded Dec. 31, 2021 from Google Patents.*
International Search Report of PCT/KR2018/010549, dated Dec. 20, 2018, English translation.
Office Action from Korean intellectual Property Office of 10-2018-0107042, dated Dec. 18, 2919.
Jiang Bu et al, Preparation and expansion properties of a novel UV-curable intumescent flame-retardant coating, Journal of Thermal Analyse and Calorimetry, May 20, 2015, pp. 329-338, vol. 122, Springer, New York City, USA.
Ivo Grabchev and Vladimir Bojinov, Photoisomerization of Triazine-stilbene Fluorescent Brighteners in Solution and in their Copolymers with Styrene, Zeitschrift fur Naturforschung, Jun. 13, 2000, pp. 833-836, vol. 55a, Walter De Gruyter GmbH , Berlin, Germany.
Klaus Bretterbauer et al, UV-curable coatings of highly crosslinked trimethylmelamine based acrylates and methacrylates, European Polymer Journal, Sep. 2013, vol. 49, pp. 4141-4148, ELSEVIER, Amsterdam, Netherlands.
Dr. L. Dimter et al, On the use of the reaction products of methylolmelamines and unsaturated carboxylic acids as polymerizable adhesives, Plaste und Kautschuk, 1967, vol. 14, No. 3, p. 148-151, Verlag für Grundstoffindustrie, Leipzig, Germany.
Yasuo Yuki et al, Preparation and Polymerization of Acrylamidoanilino or Acrylamidophenyl-1, 3, 5-triazines, Kobunshi Ronbunshu, Nov. 1983, vol. 40, No. 11, pp. 739-744, The Society of Polymer Science, Tokyo, Japan, English translation of abstract.

* cited by examiner

*Primary Examiner* — Clinton A Brooks
(74) *Attorney, Agent, or Firm* — STIP Law Group, LLC

(57) ABSTRACT

The present invention relates to a compound represented by any one of the following formula A to formula C, and a photosensitive composition comprising the same, wherein the structure of the compound represented by any one of formula A to formula C is as described in the detailed description of the invention.

23 Claims, No Drawings

TRIAZINE DERIVATIVE AND PHOTOSENSITIVE COMPOSITION COMPRISING SAME

CROSS-REFERENCE TO RELATED APPLICATIONS

This application is the U.S. National Phase under 35 U.S.C. § 371 of International Application No. PCT/KR2018/010549 filed on Sep. 10, 2018, which in turn claims the benefit of Korean Applications No. 10-2017-0117396 filed on Sep. 13, 2017, and 10-2018-0107042, filed on Sep. 7, 2018, and the disclosures of which are incorporated by reference into the present application.

TECHNICAL FIELD

The present disclosure relates to a novel triazine derivative and a photosensitive composition comprising the same. More particularly, the present disclosure relates to a novel triazine derivative that exhibits a high refractive index following a photocrosslinking process and high curability when used in a fabrication process of refractive index optical materials and is superior in terms of transmittance and anti-yellowing properties after being cured, and a photosensitive composition comprising the same.

BACKGROUND ART

A liquid crystal display (LCD) comprises a substrate film and an optical sheet formed on the substrate film and having an optical pattern, wherein a light guide plate may be arranged beneath the optical sheet or another optical sheet may be disposed between the optical sheet and the light guide plate.

Here, examples of the optical sheet include a reflector sheet, a diffuser sheet, a prism sheet, and a microlens. Such optical sheets are used in order to enhance the luminance of the backlight unit.

In an LCD, light comes from a light guide plate of a backlight unit and is refracted by an optical sheet before traversing the liquid crystal to reach the screen. In this regard, the optical sheet is designed to enhance the luminance of the light. To this end, optical sheets such as prism sheets, DBEF, etc. should have high refractive indices.

With the development of LCD panel fabrication technology, particularly, there has been a demand for LCD devices that are thin and show high luminance. Various attempts have therefore been made to increase the luminance of the backlight unit.

However, conventional high refractive index monomers can bring about only a limited effect in luminance enhancement because of the poor refractive indices thereof. In addition, even when made to increase the refractive index, optical sheets suffer from the problem of a yellowing phenomenon.

With respect to related arts concerning high refractive index monomers, reference may be made to Korean Patent No. 10-1692343 (issued on Dec. 28, 2016) and Korean Patent No. 10-2017-0013674 A (issued on 2017 Feb. 7), which suggest acryl-based monomers as high refractive index monomers.

In spite of conventional techniques including the related arts, there has been a requirement of high refractive index monomers that are excellent in transmittance and anti-yellowing properties and have high refractive indices in order to enhance the luminance of LCD devices. Therefore, a need for developing novel high refractive index monomers is ongoing.

DETAILED DESCRIPTION OF THE INVENTION

Technical Problem

Therefore, a purpose of the present disclosure is to provide a novel triazine derivative compound that has high transmittance and excellent photocrosslinking and anti-yellowing properties and can be used as a monomer in a photosensitive composition having a high refractive property.

Another purpose of the present disclosure is to provide a photosensitive composition comprising the triazine derivative compound and an optical product article obtained by polymerizing the same.

Technical Solution

In order to achieve the purposes, the present disclosure provides a compound represented by any one of the following [Chemical Formula A] to [Chemical Formula C]:

[Chemical Formula A]

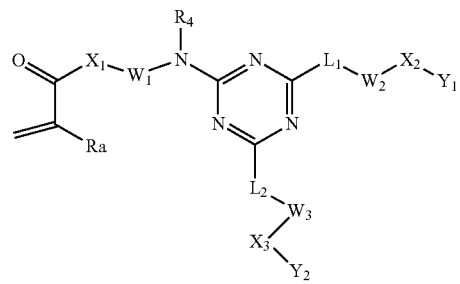

wherein,

Ra is a substituent selected from a hydrogen atom, a deuterium atom, a substituted or unsubstituted alkyl of alkyl of $C_1$-$C_6$, $L_1$ is any one selected from a single bond, O, S, and —N(—$R_5$)—, $L_2$ is any one selected from a single bond, O, S, and —N(—$R_6$)—, $X_1$ to $X_3$, which may be the same or different, are each independently any one selected from a single bond, O, S, —N(—$R_7$)—, and —O(($CH_2$)$_m$O)$_n$— wherein m and n, which may be the same or different, are each independently an integer of 1 to 4 and wherein when at least two of $X_1$ to $X_3$ are each —N(—$R_7$)— or —O(($CH_2$)$_m$O)$_n$—, the individual —N(—$R_7$)— moieties or the individual —O(($CH_2$)$_m$O)$_n$— moieties may be the same or different, $R_4$ to $R_7$, which may be the same or different, are each independently any one selected from a hydrogen atom, a deuterium atom, a substituted or unsubstituted alkyl of $C_1$-$C_{30}$, a substituted or unsubstituted aryl of $C_6$-$C_{50}$, a substituted or unsubstituted cycloalkyl of $C_3$-$C_{30}$, and a substituted or unsubstituted arylalkyl of $C_7$-$C_{24}$, $W_1$ is any one selected from a single bond, a substituted or unsubstituted arylene of $C_6$-$C_{30}$, and a substituted or unsubstituted alkylene of $C_1$-$C_{12}$, $W_2$ and $W_3$, which may be the same or different, are each independently any one selected from a single bond, a substituted or unsubstituted alkylene of $C_1$-$C_{30}$, a substituted or unsubstituted arylene of $C_6$-$C_{30}$, a substituted or unsubstituted alkenylene of alkenylene of $C_2$-$C_{30}$, a substituted or unsubstituted cycloalkylene of cycloalkylene of $C_3$-$C_{30}$, a substituted or unsubstituted cycloalkenylene of $C_5$-$C_{30}$, a substituted or unsubstituted heteroarylene of $C_2$-$C_{50}$, and a substituted or unsubstituted heterocycloalkylene of heterocycloalkylene of $C_2$-$C_{30}$, $Y_1$ and $Y_2$, which may be the same or different, are each independently any one selected from a hydrogen atom, a deuterium atom a substituted or unsubstituted alkyl of $C_1$-$C_{30}$, a substituted or unsubstituted aryl of $C_6$-$C_{30}$, a substituted or unsubstituted alkenyl of $C_2$-$C_{30}$, a substituted or unsubstituted alkynyl of $C_2$-$C_{20}$, a substituted or unsubstituted cycloalkyl of $C_3$-$C_{30}$, a substituted or unsubstituted cycloalkenyl of $C_5$-$C_{30}$, a substituted or unsubstituted heteroaryl of heteroaryl of $C_2$-$C_{50}$, a substituted or unsubstituted heterocycloalkyl of heterocycloalkyl of $C_2$-$C_{30}$, a substituted or unsubstituted alkylsilyl of $C_1$-$C_{30}$, a substituted or unsubstituted arylsilyl of $C_6$-$C_{30}$, and a substituent represented by the following Structural Formula 1 or 2:

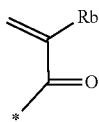

[Structural Formula 1]

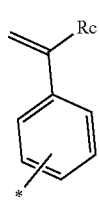

[Structural Formula 2]

wherein,

Rb and Rc, which may be the same or different, are each independently any one selected from a hydrogen atom, a deuterium atom, and a substituted or unsubstituted alkyl of $C_1$-$C_6$, and -*" means a bonding site at which the substituent represented by Structural Formula 1 or Structural Formula 2 is bonded to $X_2$ or $X_3$ in Chemical Formula A; and

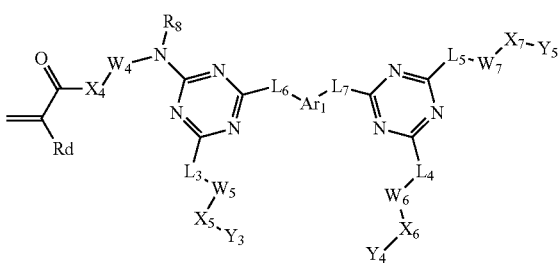

[Chemical Formula B]

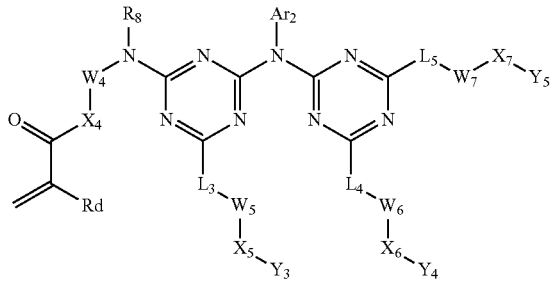

[Chemical Formula C]

wherein, $Ar_1$ is any one selected from a substituted or unsubstituted arylene of $C_6$-$C_{30}$, a substituted or unsubstituted heteroarylene of $C_2$-$C_{30}$, a substituted or unsubstituted alkylene of $C_1$-$C_{30}$, a substituted or unsubstituted alkenylene of $C_2$-$C_{30}$, a substituted or unsubstituted cycloalkylene of $C_3$-$C_{30}$, and a substituted or unsubstituted cycloalkenylene of $C_5$-$C_{30}$, $L_6$ is any one selected from a single bond, O, S, and —N(—$R_1$)—, and $L_7$ is any one selected from a single bond, O, S, and —N(—$R_{12}$)—; and $Ar_2$ is any one selected from a hydrogen atom, a deuterium atom, a substituted or unsubstituted aryl of $C_6$-$C_{30}$, a substituted or unsubstituted heteroaryl of heteroaryl of $C_2$-$C_{30}$, a substituted or unsubstituted alkyl of $C_1$-$C_{30}$, a substituted or unsubstituted cycloalkyl of $C_3$-$C_{30}$, a substituted or unsubstituted alkenyl of $C_2$-$C_{30}$, and a substituted or unsubstituted cycloalkenyl of $C_5$-$C_{30}$, Rd is a substituent selected from a hydrogen atom, a deuterium atom, and a substituted or unsubstituted alkyl of $C_1$-$C_6$, $L_3$ to $L_5$, which may be the same or different, are each independently any one selected from a single bond, O, S, and —N(—R9)—, wherein when at least two of $L_3$ to $L_5$ are each —N(—$R_9$)—, the individual —N(—$R_9$) moieties may be the same or different, $X_4$ to $X_7$, which may be the same or different, are each independently any one selected from a single bond, O, S, —N(—$R_{10}$)—, and —O(($CH_2$)$_m$O)$_n$— wherein m and n, which may be the same or different, are each independently an integer of 1 to 4, wherein when at least two of $X_4$ to $X_7$ are each —N(—$R_{10}$)— or —O(($CH_2$)$_m$O)$_n$—, the individual —N(—$R_{10}$)— moieties or the individual —O(($CH_2$)$_m$O)$_n$- moieties may be the same or different, $R_8$ to $R_{12}$, which may be the same or different, are each independently any one selected from a hydrogen atom, a deuterium atom, a substituted or unsubstituted alkyl of $C_1$-$C_{30}$, a substituted or unsubstituted aryl of $C_6$-$C_{30}$, a substituted or unsubstituted cycloalkyl of $C_3$-$C_{30}$, and a substituted or unsubstituted arylalkyl of $C_7$-$C_{24}$, $W_4$ is any one selected from a single bond, a substituted or unsubstituted arylene of $C_6$-$C_{30}$, and a substituted or unsubstituted alkylene of $C_1$-$C_{12}$, $W_5$ to $W_7$, which may be the same or different, are each independently any one selected from a single bond, a substituted or unsubstituted alkylene of $C_1$-$C_{30}$, a substituted or unsubstituted arylene of $C_6$-$C_{30}$, a substituted or unsubstituted alkenylene of $C_2$-$C_{30}$, a substituted or unsubstituted cycloalkylene of $C_3$-$C_{30}$, a substituted or unsubstituted cycloalkenylene of $C_5$-$C_{30}$, a substituted or unsubstituted heteroarylene of $C_2$-$C_{50}$, and a substituted or unsubstituted heterocycloalkylene of $C_2$-$C_{30}$, $Y_3$ to $Y_5$, which may be the same or different, are each independently any one selected from a hydrogen atom, a deuterium atom a substituted or unsubstituted alkyl of $C_1$-$C_{30}$, a substituted or unsubstituted aryl of $C_6$-$C_{30}$, a substituted or unsubstituted alkenyl of $C_2$-$C_{30}$, a substituted or unsubstituted alkynyl of $C_2$-$C_{20}$, a substituted or unsubstituted cycloalkyl of $C_3$-$C_{30}$, a substituted or unsubstituted cycloalkenyl of $C_5$-$C_{30}$, a substituted or unsubstituted heteroaryl of $C_2$-$C_{50}$, a substituted or unsubstituted heterocycloalkyl of $C_2$-$C_{30}$, a substituted or unsubstituted alkylsilyl of $C_1$-$C_{30}$, a substituted or unsubstituted arylsilyl of $C_6$-$C_{30}$, and a substituent represented by the [Structural Formula 1] or [Structural Formula 2]

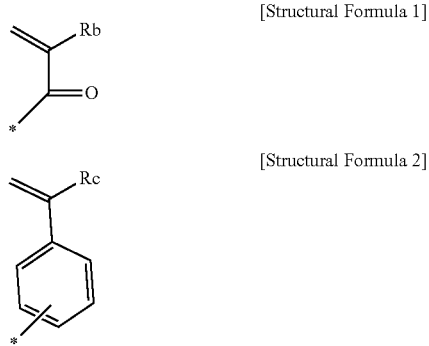

[Structural Formula 1]

[Structural Formula 2]

wherein,

Rb and Rc, which may be the same or different, are each independently any one selected from a hydrogen atom, a deuterium atom, and a substituted or unsubstituted alkyl of $C_1$-$C_6$, and "-*" means a bonding site at which the substituent represented by Structural Formula 1 or Structural Formula 2 is bonded to $X_5$ to $X_7$ in [Chemical Formula B] or [Chemical Formula C], wherein the term "substituted" in the expression "substituted or unsubstituted" used for [Chemical Formula A] to [Chemical Formula C] means having at least one substituent selected from the group consisting of a deuterium atom, a cyano, a halogen, a hydroxy, a nitro, an alkyl of $C_1$-$C_{24}$, an halogenated alkyl of $C_1$-$C_{24}$, an alkenyl of $C_2$-$C_{24}$, an alkynyl of $C_2$-$C_{24}$, a heteroalkyl of $C_1$-$C_{24}$, an aryl of $C_6$-$C_{24}$, an arylalkyl of $C_7$-$C_{24}$, a heteroaryl of $C_2$-$C_{24}$, a heteroarylalkyl of $C_2$-$C_{24}$, an alkoxy of $C_1$-$C_{24}$, an alkylthionyl of $C_1$-$C_{24}$, an alkylamino of $C_1$-$C_{24}$, an arylamino of $C_6$-$C_{24}$, a heteroarylamino of $C_1$-$C_{24}$, an alkylsilyl of $C_1$-$C_{24}$, an arylsilyl of $C_6$-$C_{24}$, an aryloxy of $C_6$-$C_{24}$, and an arylthionyl of $C_6$-$C_{24}$.

In addition, the present disclosure provides a photosensitive composition comprising the compound represented by any one of [Chemical Formula A] to [Chemical Formula C] and an optical material or optical product article obtained by polymerizing the same.

Advantageous Effect

The novel triazine derivative compound, represented by any one of [Chemical Formula A] to [Chemical Formula C], according to the present disclosure is available in a photosensitive composition, allowing for provision of a high refractive index.

Particularly, provided is a photosensitive composition that exhibits high transmittance and excellent anti-yellowing properties. Having the effect of being able to solving the problems with conventional techniques, including the limited enhancement in luminance due to poor refractive indices and the yellowing phenomenon resulting in the discoloration of optical sheets, the photosensitive composition can find advantageous applications in the preparation of prism sheets, microlenses, LCD coating materials, dual brightness enhancement films (DBEF), OLED coating materials, optical lenses, multifocal lenses, and so on.

BEST MODE FOR INVENTION

Mode for Carrying Out the Invention

Below, a detailed description will be given of the present disclosure. Unless defined otherwise, all technical and scientific terms used herein have the same meaning as commonly understood by one of ordinary skill in the art to which this invention belongs. In general, the nomenclature used herein is well known and commonly used in the art.

Throughout the specification, when a portion may "include" a certain constituent element, unless explicitly described to the contrary, it may not be construed to exclude another constituent element but may be construed to further include other constituent elements.

The compound, represented by any one of [Chemical Formula A] to [Chemical Formula C], according to the present disclosure has a structure including one to three triazine skeletons in which the carbon atoms as members of each triazine moiety are respectively bonded with a first linker selected from N, O, S, and a single bond, a second linker selected from a single bond, an alkylene group, and an arylene group; and a third linker selected from N, O, S, alkylene oxide, and a single bond, with at least one double bond moiety, such as an acrylic acid derivative, grafted to the end thereof, wherein a nitrogen atom is bonded to at least one of the three carbon atom as members in each triazine moiety and the structure terminates with a double bond moiety, such as an acrylic acid derivative.

When the triazine compound represented by any one of [Chemical Formula A] to [Chemical Formula C] is used as a monomer, a photosensitive composition comprising the same guarantees superiority in refractive index and transmittance and excellency in anti-yellowing properties.

The expression indicating the number of carbon atoms, such as "a substituted or unsubstituted alkyl of $C_1$-$C_{20}$", "a substituted or unsubstituted aryl of $C_6$-$C_{50}$", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of $C_6$, even though it is substituted with a butyl radical of $C_4$.

As used herein, the term "aryl" means an organic radical derived from an aromatic hydrocarbon by removing one hydrogen that is bonded to the aromatic hydrocarbon. It may be a single or fused aromatic system including a 5-to 7-membered ring, and preferably a 5- to 6-membered ring. Further, the aromatic system may include a fused ring that is formed by adjacent substituents on the aryl radical.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl at least one hydrogen atom of which may be substituted by a deuterium atom, a halogen atom, a hydroxy, a nitro, a cyano, a silyl, an amino (—$NH_2$, —NH(R), —N(R')(R") wherein R' and R" are each independently an alkyl of $C_1$-$C_{10}$, in this case, called "alkylamino"), an amidino, a hydrazine, a hydrazone, a carboxyl, a sulfonic acid, a phosphoric acid, an alkyl of $C_1$-$C_{24}$, a halogenated alkyl of $C_1$-$C_{24}$, an alkenyl of $C_2$-$C_{24}$, an alkynyl of $C_2$-$C_{24}$, a heteroalkyl of $C_1$-$C_{24}$, an aryl of $C_6$-$C_{24}$, an arylalkyl of $C_7$-$C_{24}$, a heteroaryl of $C_2$-$C_{24}$, or a heteroarylalkyl of $C_2$-$C_{24}$.

The substituent heteroaryl used in the compound of the present disclosure refers to a heteroaromatic radical of $C_2$-$C_{24}$ bearing one, two, or three heteroatoms selected from among N, O, P, Si, S, Ge, Se, and Te in each ring of the aryl, wherein the rings may be fused. One or more hydrogen atoms on the heteroaryl may be substituted by the same substituents as on the aryl.

Examples of the substituent alkyl useful in the present disclosure include methyl, ethyl, propyl, propyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the compound of the present disclosure include methoxy, ethoxy, propoxy, isobutyloxy, sec-butyloxy, pentyloxy, iso-amyloxy, and hexyloxy.

At least one hydrogen atom of the alkoxy may be substituted by the same substituent as in the aryl.

Concrete examples of the alkylaryl used in the compound of the present disclosure include methylphenyl, dimethylphenyl, n-propylphenyl, t-butylphenyl, and methylnaphthyl. At least one hydrogen atom of the alkylaryl may be substituted by the same substituents as in the aryl.

Concrete examples of the cycloalkyl used in the compound of the present disclosure include cyclobutyl, cyclopentyl, cyclohexyl, methylcyclopentyl, methylcyclohexyl, ethylcyclopentyl, and ethylcyclohexyl. At least one hydrogen atom of the cycloalkyl may be substituted by the same substituents as in the aryl.

Representative among examples of the silyl useful in the compound of the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted by the same substituent as in the aryl.

In Chemical Formula A, the substituents $R_4$ to $R_6$, which may be the same or different, are each independently any one selected from a hydrogen atom, a deuterium atom, a substituted or unsubstituted alkyl of $C_1$-$C_{20}$, and a substituted or unsubstituted aryl of $C_6$-$C_{20}$, and Ra, Rb, and Rc, which may be the same or different, are each independently any one selected from a hydrogen atom, a deuterium atom, and a methyl.

In addition, at least one of $Y_1$ and $Y_2$ in Chemical Formula A may be represented by Structural Formula 1 or Structural Formula 2. Given to either or both of $Y_1$ and $Y_2$, the structure provides the opposite ends of the monomer with a double bond and thus can control the photocrosslinking rate upon photopolymerization.

In Chemical Formula A, $L_1$ may be —N(—$R_5$)— or S and $L_2$ may be —N(—$R_6$)— or S. More preferably, $L_1$ may be —N(—$R_5$)—, $L_2$ may be —N(—$R_6$)—, and $R_5$ and $R_6$, which may be the same or different, may each be independently any one selected from a hydrogen atom, a deuterium atom, an alkyl of $C_1$-$C_{10}$, and an aryl of $C_6$-$C_{20}$.

That is, $L_1$ and $L_2$ in Chemical Formula A may each bear a nitrogen atom or a sulfur atom. In this case, excellent transmittance and high refractive index properties can be obtained.

According to the present disclosure, at least one of $W_1$ to $W_3$ in Chemical Formula A may be a substituted or unsubstituted arylene of $C_6$-$C_{30}$. Preferably, at least two or all of $W_1$ to $W_3$ may be a substituted or unsubstituted arylene of $C_6$-$C_{30}$.

In this regard, the aromatic planar structure of the arylene of $C_6$-$C_{30}$ forms a flat domain, together with the planar structure of the triazine, whereby high refractive index properties would be obtained.

In an exemplary embodiment wherein at least one of $W_1$ to $W_3$ in Chemical Formula A is a substituted or unsubstituted arylene of $C_6$-$C_{30}$, $W_1$ may be a substituted or unsubstituted phenylene and $W_2$ and $W_3$, which may be the same or different, are each independently any one selected from a single bond, a substituted or unsubstituted arylene of $C_6$-$C_{30}$, and a substituted or unsubstituted alkylene of $C_1$-$C_{12}$.

In another exemplary embodiment wherein at least two of $W_1$ to $W_3$ are a substituted or unsubstituted arylene of $C_6$-$C_{30}$, $W_1$ is a substituted or unsubstituted phenylene and at least one of $W_2$ and $W_3$, which may be the same or different, is a substituted or unsubstituted arylene of $C_6$-$C_{30}$, at least two of $W_1$ to $W_3$, which may be the same or different, are a substituted or unsubstituted phenylene, or all of $W_1$ to $W_3$, which may be the same or different, are a substituted or unsubstituted phenylene.

In [Chemical Formula B] and [Chemical Formula C] of the present disclosure, $R_8$ to $R_{12}$, which may be the same or different, are each independently any one selected from a hydrogen atom, a deuterium atom, a substituted or unsubstituted alkyl of $C_1$-$C_{20}$, a substituted or unsubstituted aryl of $C_6$-$C_{20}$, and Ra, Rb, and Rc, which may be the same or different, are each independently any one selected from a hydrogen atom, a deuterium atom, and a methyl.

In [Chemical Formula B] and [Chemical Formula C], at least one of $Y_3$ and $Y_5$ may be represented by Structural Formula 1 or Structural Formula 2. Given to either or both of $Y_3$ and $Y_5$, the structure provides the opposite ends of the monomer with a double bond and thus can control the photocrosslinking rate upon photopolymerization.

In addition, $L_3$ to $L_7$ in [Chemical Formula B], which may be the same or different, are each independently a single bond, —N(—$R_9$)—, or S, wherein when at least two of $L_3$ to $L_7$ are each —N(—$R_9$)—, the individual —N(—$R_9$)— moieties may be the same or different and may each be independently any one selected from a hydrogen atom, a deuterium atom, an alkyl of $C_1$-$C_{10}$, and an aryl of $C_6$-$C_{20}$.

In [Chemical Formula C], $L_3$ to $L_5$, which may the same or different, are each independently a single bond, —N(—$R_9$)—, or S, wherein when at least two of $L_3$ to $L_5$ are —N(—$R_9$)—, the individual —N(—$R_9$)— moieties may be the same or different and may each be independently any one selected from a hydrogen atom, a deuterium atom, an alkyl of $C_1$-$C_{10}$, and an aryl of $C_6$-$C_{20}$.

Herein, $L_3$ to $L_7$ in [Chemical Formula B] and [Chemical Formula C] may each bear a nitrogen atom or a sulfur atom. In this case, excellent transmittance and high refractive index properties can be obtained.

In [Chemical Formula B] and [Chemical Formula C], $R_9$ and $R_{11}$ to $R_{12}$, which may be the same or different, are each independently any one selected from a hydrogen atom, a deuterium atom, an alkyl of $C_1$-$C_{10}$, an aryl of $C_6$-$C_{20}$.

In [Chemical Formula B] and [Chemical Formula C], two, three, or all of $W_4$ to $W_7$ may be a substituted or unsubstituted arylene of $C_6$-$C_{30}$.

In this regard, the aromatic planar structure of the arylene of $C_6$-$C_{30}$ forms a flat domain, together with the planar structure of the triazine, whereby high refractive index properties would be obtained.

In an exemplary embodiment wherein at least two substituents of $W_4$ to $W_7$ in [Chemical Formula B] and [Chemical Formula C] are each independently a substituted or unsubstituted arylene of $C_6$-$C_{30}$, the two or more substituents may be a substituted or unsubstituted phenylene.

In this regard, the remaining one or two substituents of $W_4$ to $W_7$ other than the phenylene group may be the same or different and may be each independently a single bond, a substituted or unsubstituted arylene of $C_6$-$C_{30}$, or a substituted or unsubstituted alkylene of $C_1$-$C_{12}$.

In another exemplary embodiment, at least three of $W_4$ to $W_7$ in [Chemical Formula B] and [Chemical Formula C] are each independently a substituted or unsubstituted arylene of $C_6$-$C_{30}$, and three or all of $W_4$ to $W_7$ may each be a substituted or unsubstituted phenylene. When three of $W_4$ to $W_7$ are each independently a substituted or unsubstituted phenylene, the remaining one other than the phenylene group may be a single bond, a substituted or unsubstituted arylene of $C_6$-$C_{30}$, or a substituted or unsubstituted alkylene of $C_1$-$C_{12}$.

Concrete examples of the compound represented by any one of [Chemical Formula A] to [Chemical Formula C] Compound include, but are not limited to, the compounds listed below:

[Compound 1]

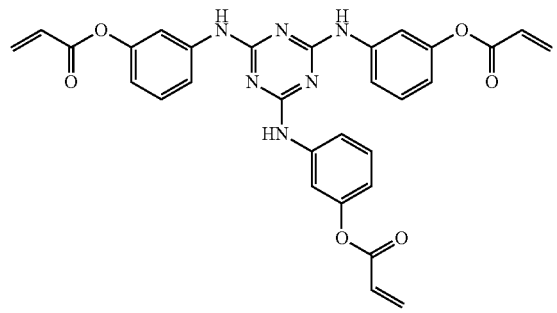

[Compound 2]

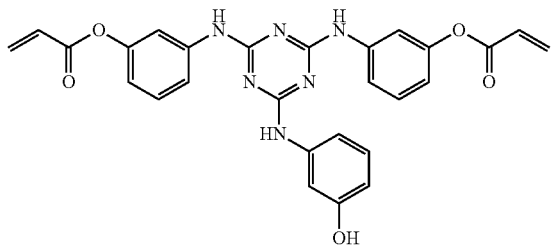

[Compound 3]

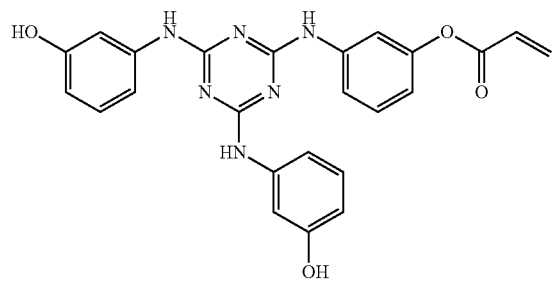

[Compound 4]

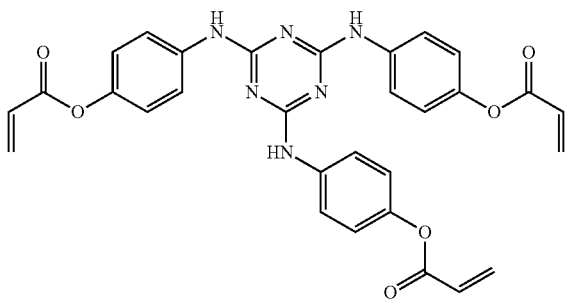

[Compound 5]

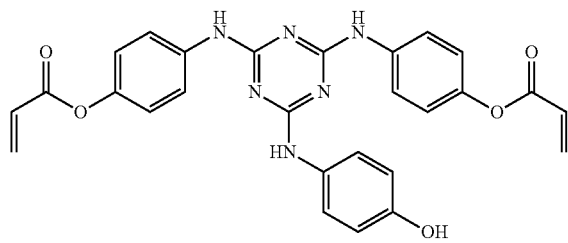

[Compound 6]

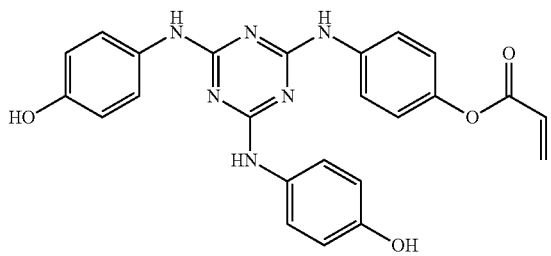

-continued
[Compound 7]
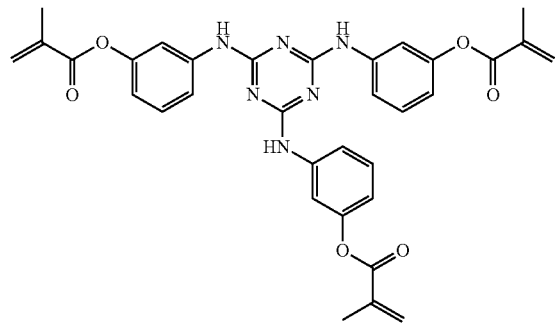
[Compound 8]
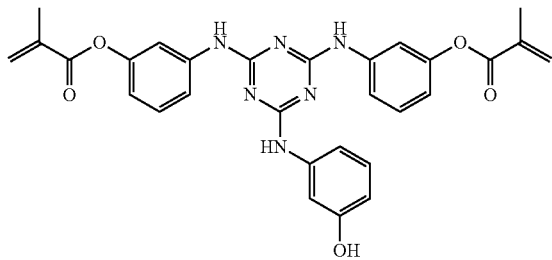
[Compound 9]
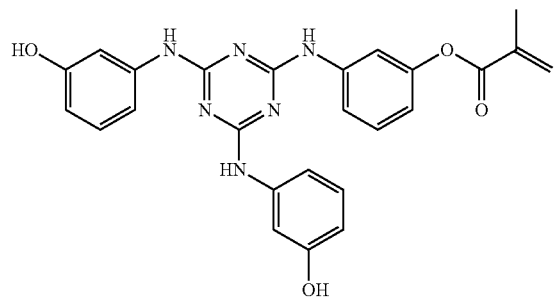
[Compound 10]
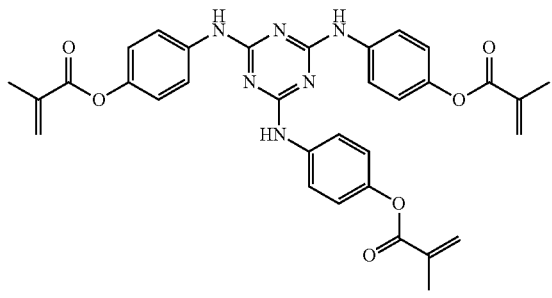
[Compound 11]
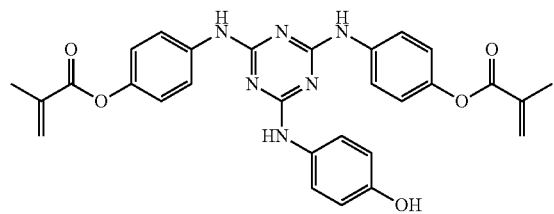
[Compound 12]
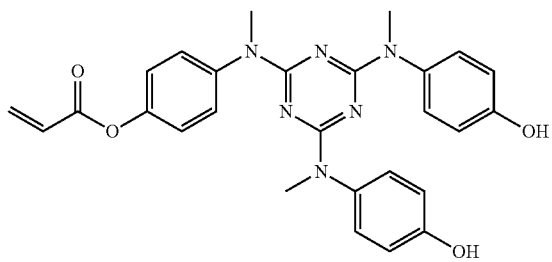
[Compound 13]
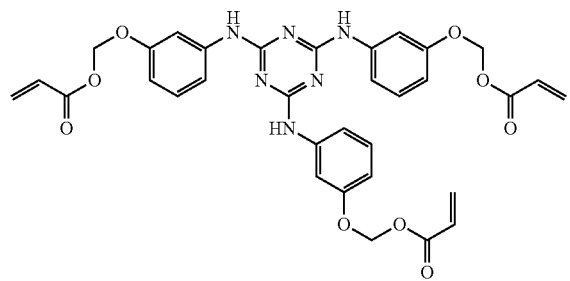
[Compound 14]
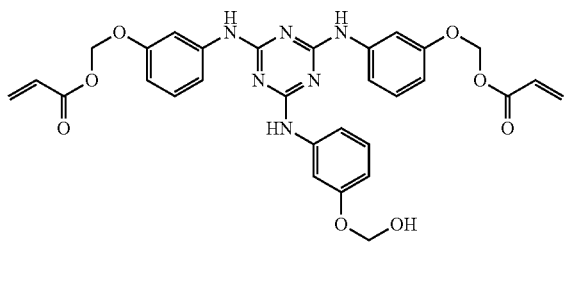
[Compound 15]
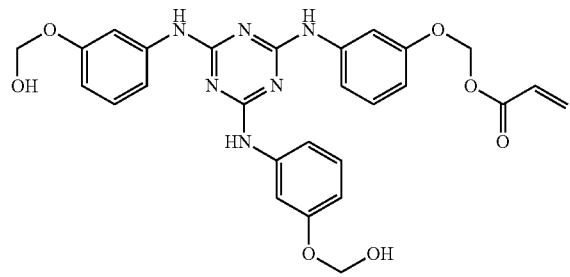
[Compound 16]
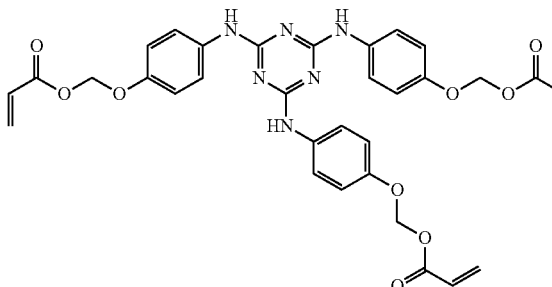

-continued
[Compound 17]
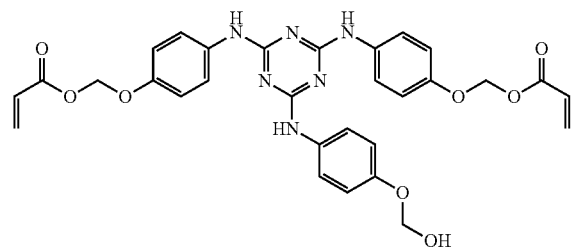
[Compound 18]
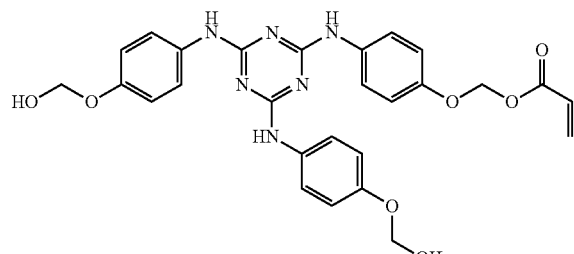
[Compound 19]
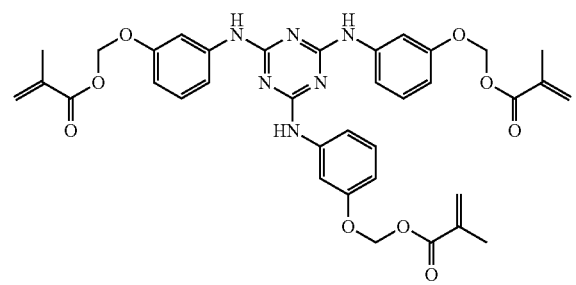
[Compound 20]
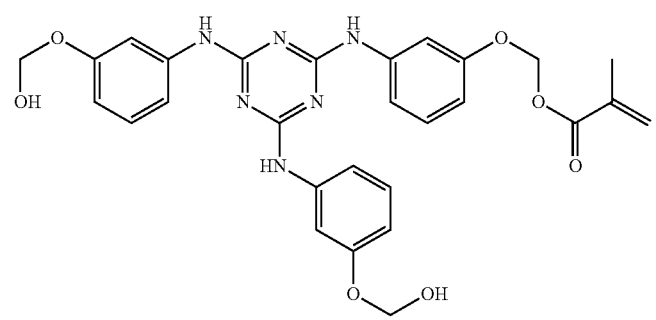
[Compound 21]
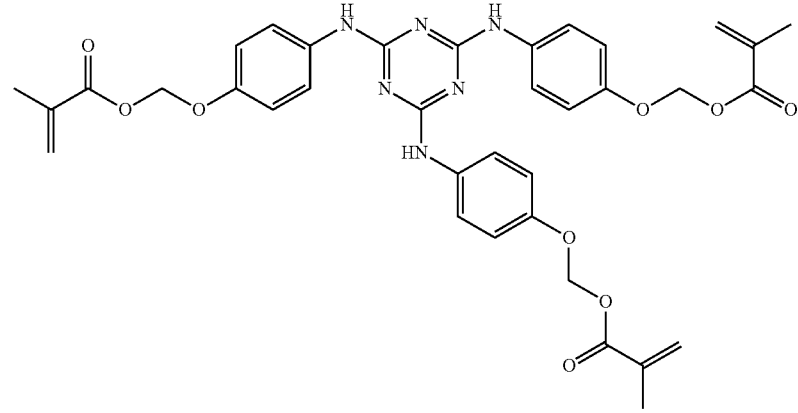
[Compound 22]
[Compound 23]
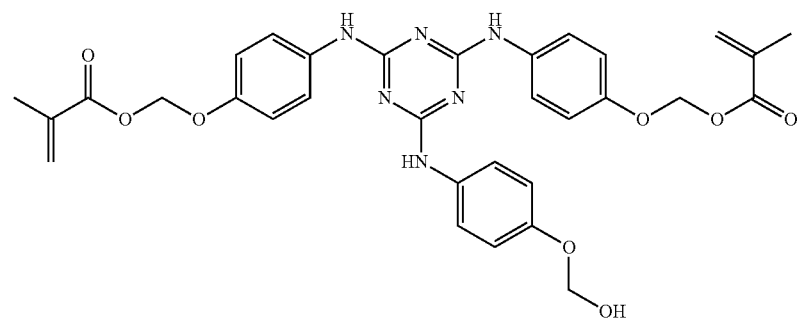

[Compound 24]
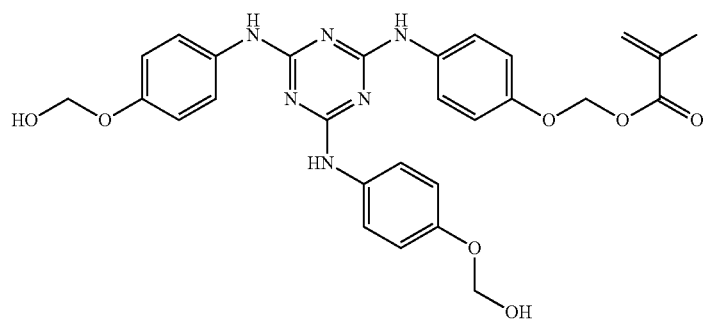
[Compound 25]
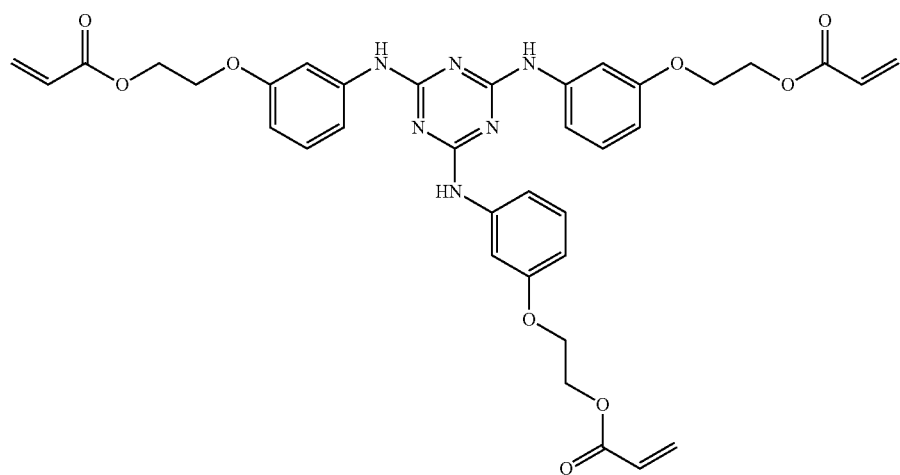
[Compound 26]
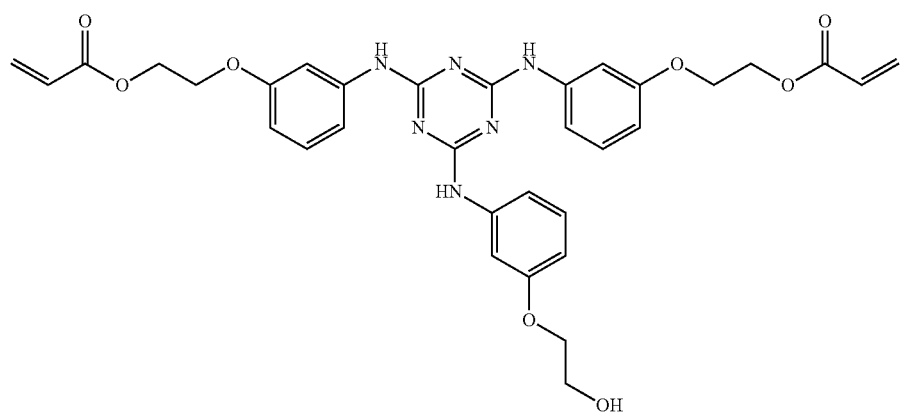
[Compound 27]
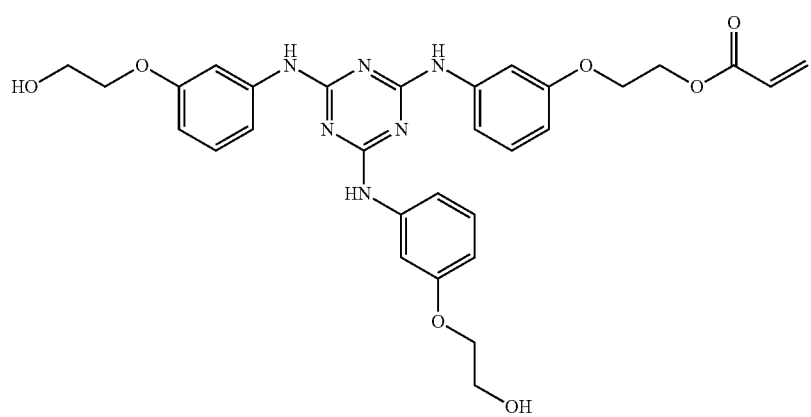

-continued
[Compound 28]
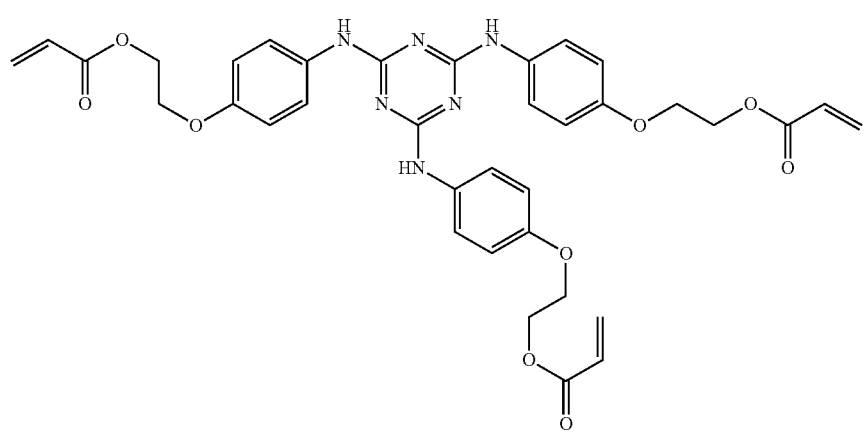
[Compound 29]
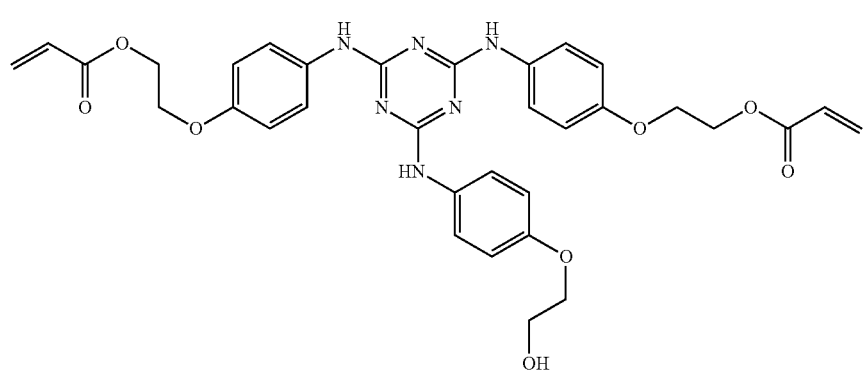
[Compound 30]
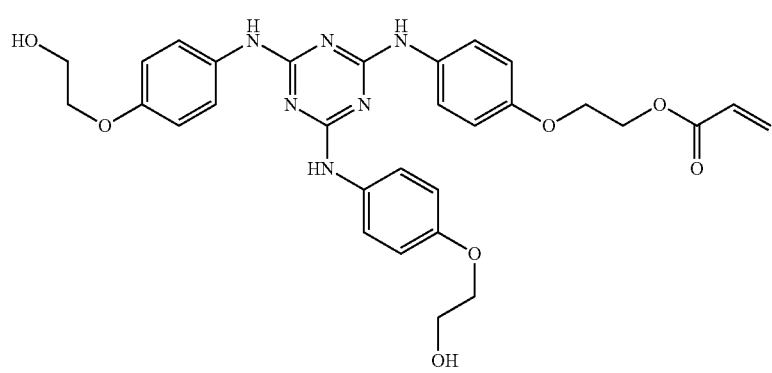
[Compound 31]
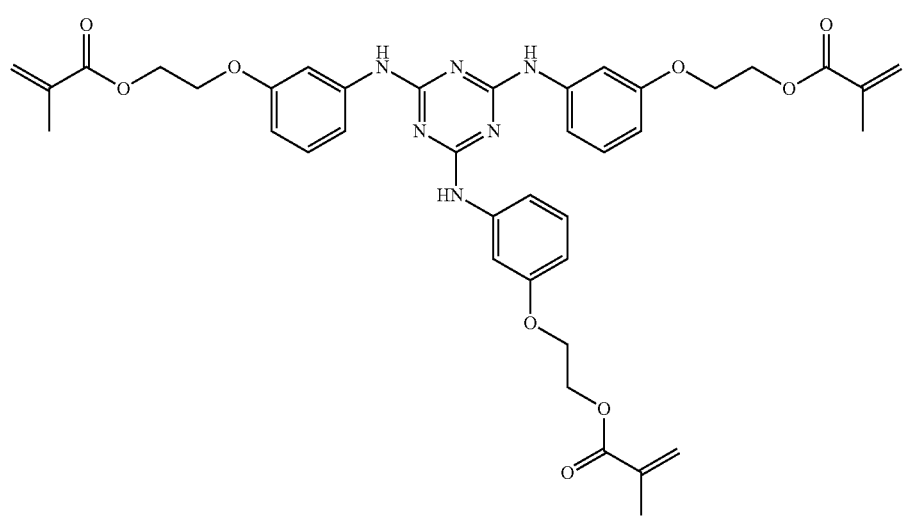

-continued
[Compound 32]
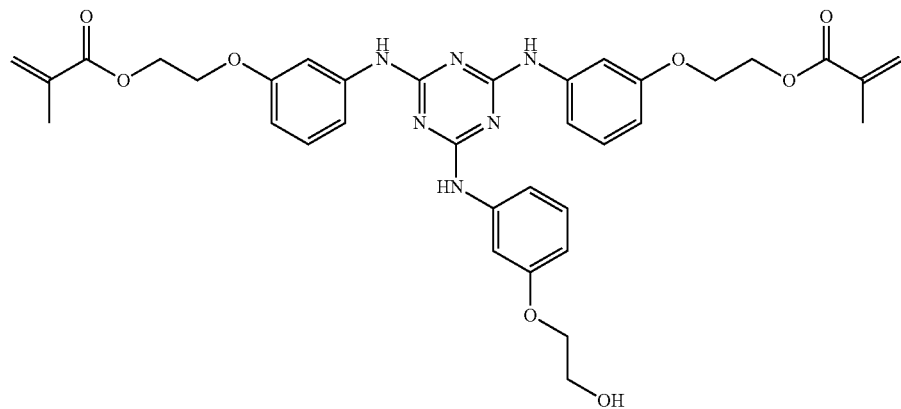
[Compound 33]
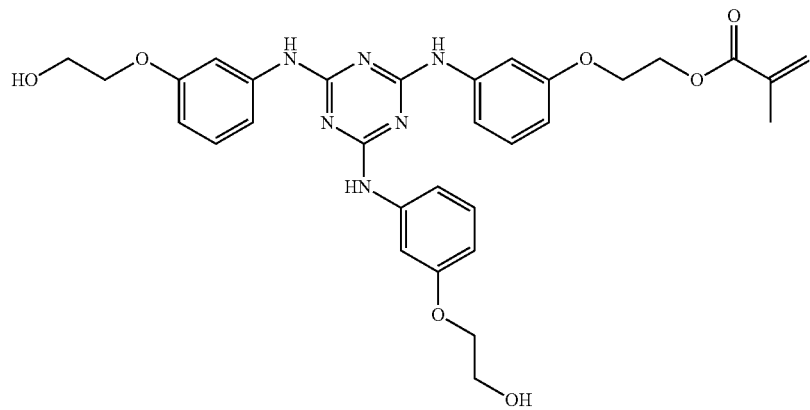
[Compound 34]
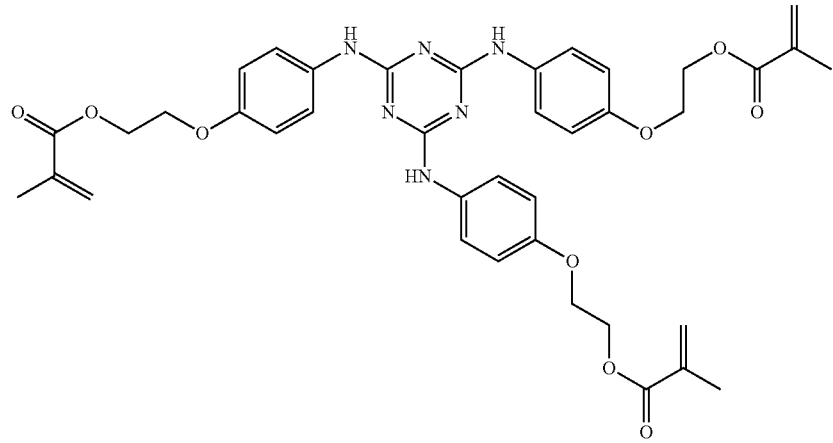
[Compound 35]
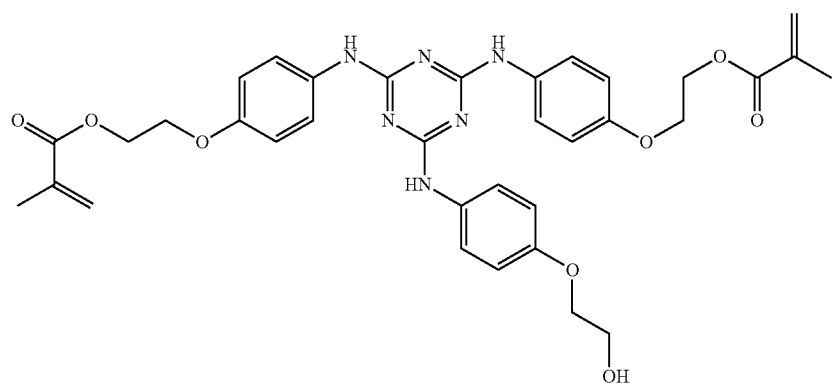

[Compound 36]
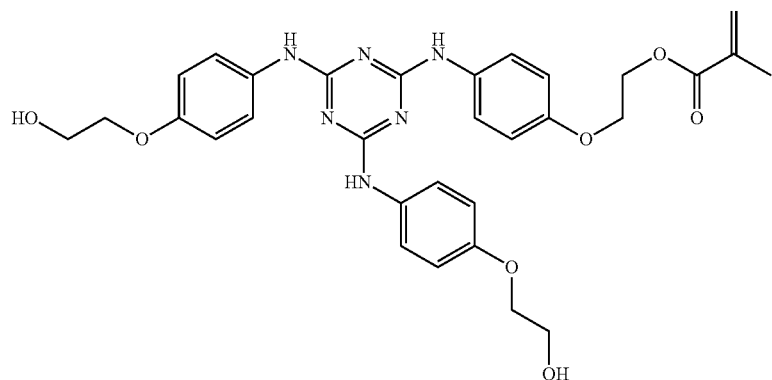
[Compound 37]
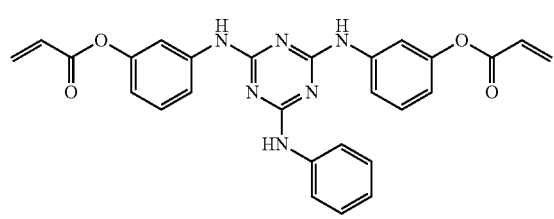
[Compound 38]
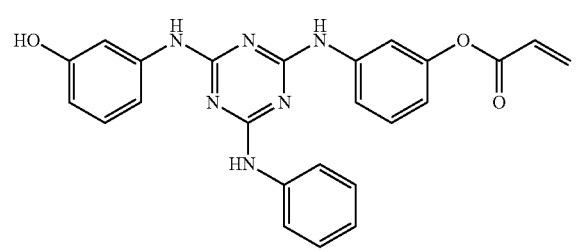
[Compound 39]
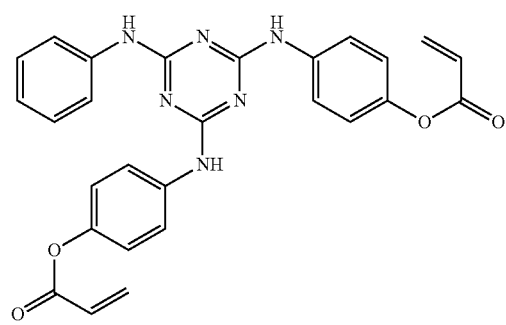
[Compound 40]
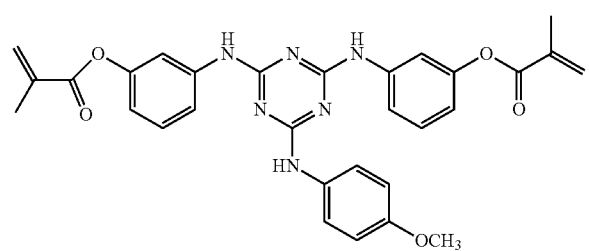
[Compound 41]
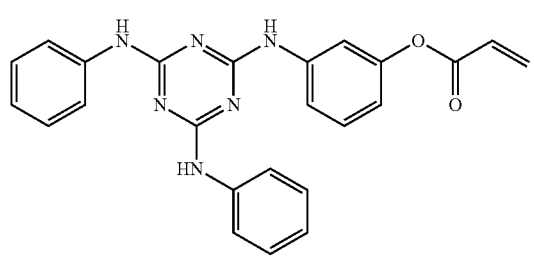
[Compound 42]
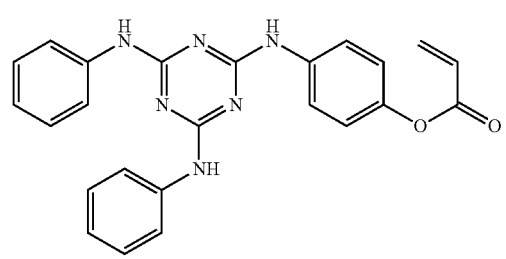
[Compound 43]
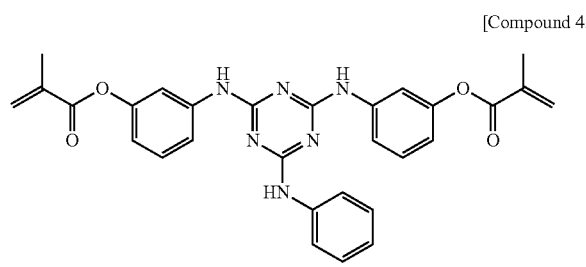
[Compound 44]
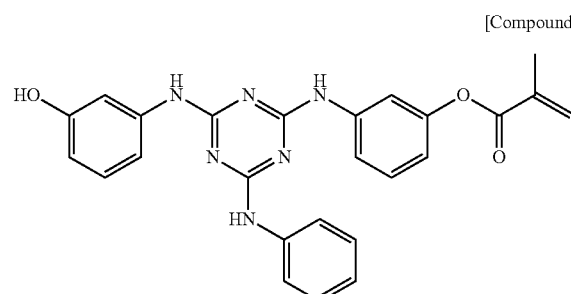

-continued
[Compound 45]
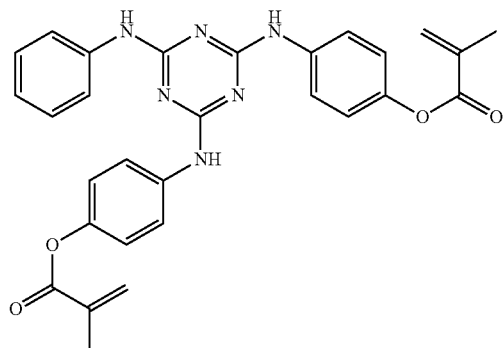
[Compound 46]
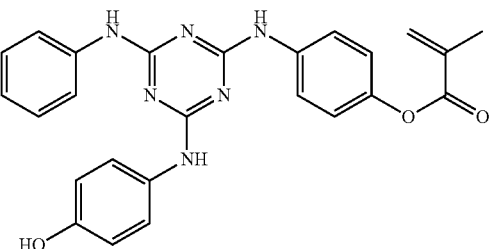
[Compound 47]
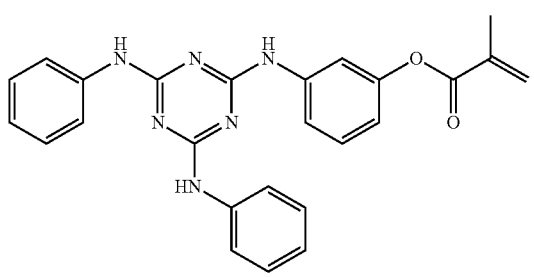
[Compound 48]
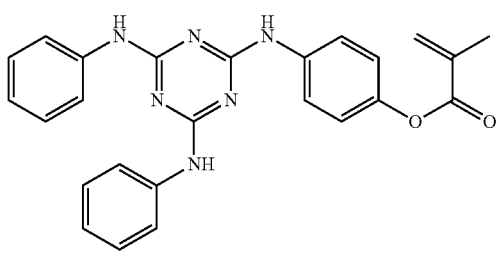
[Compound 49]
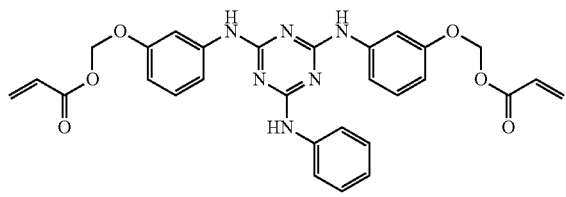
[Compound 50]
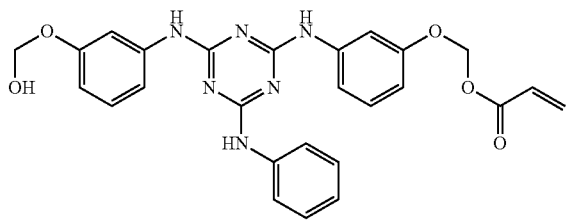
[Compound 51]
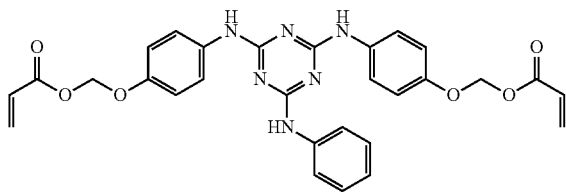
[Compound 52]
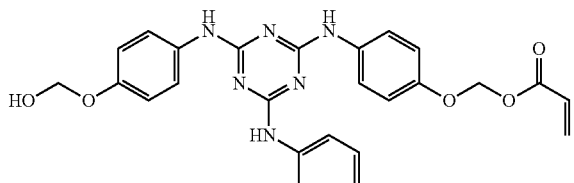
[Compound 53]
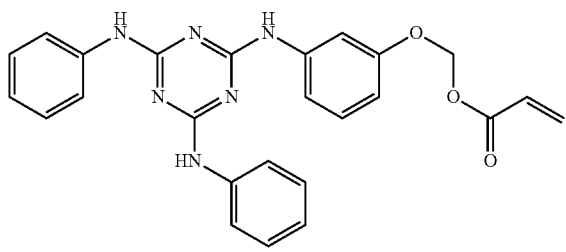
[Compound 54]
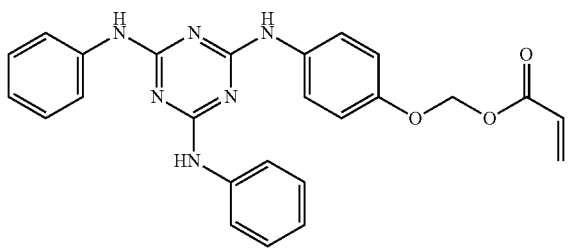

-continued
[Compound 55]
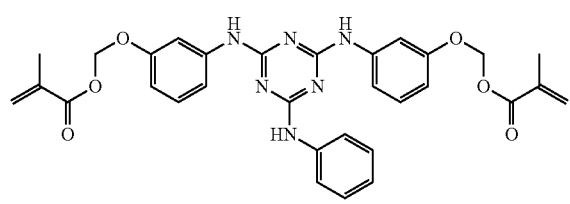
[Compound 56]
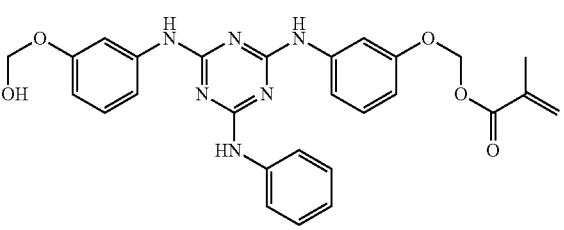
[Compound 57]
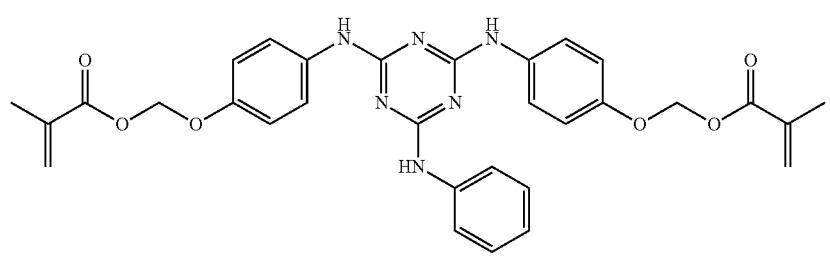
[Compound 58]
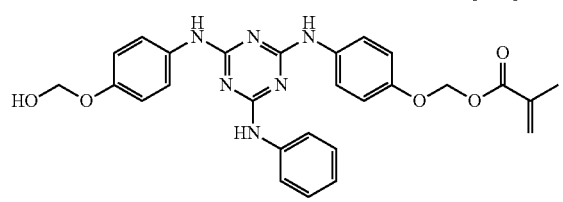
[Compound 59]
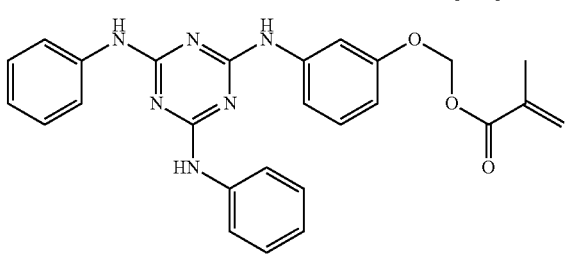
[Compound 60]
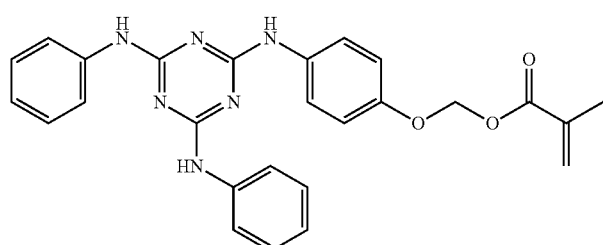
[Compound 61]
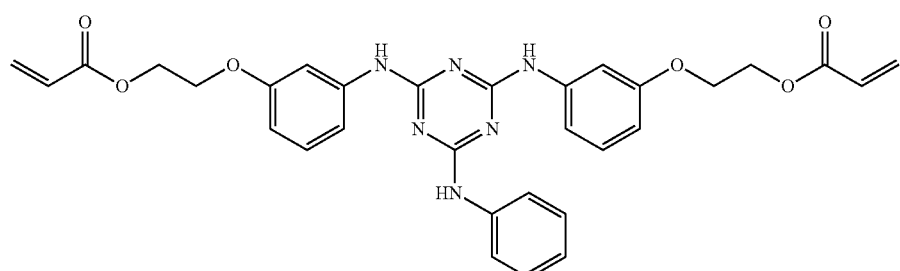
[Compound 62]
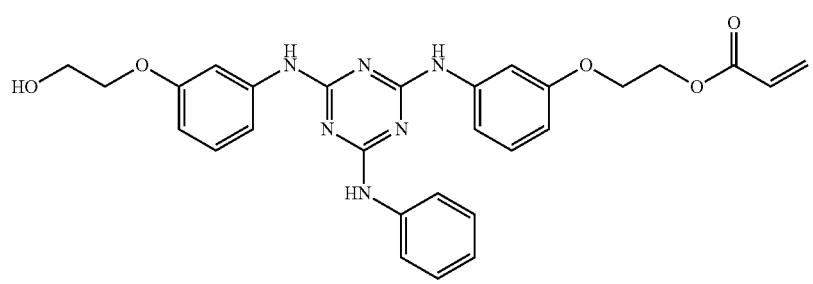

[Compound 63]
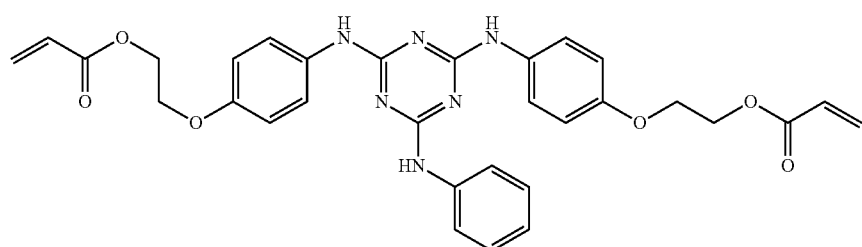
[Compound 64]
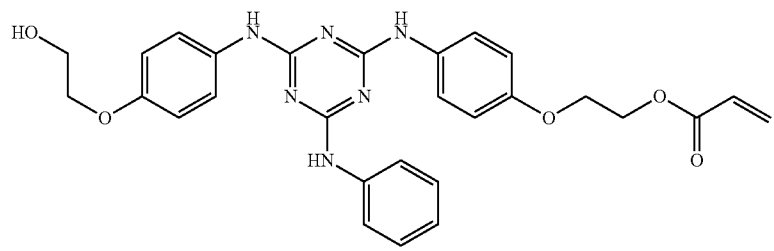
[Compound 65] [Compound 66]
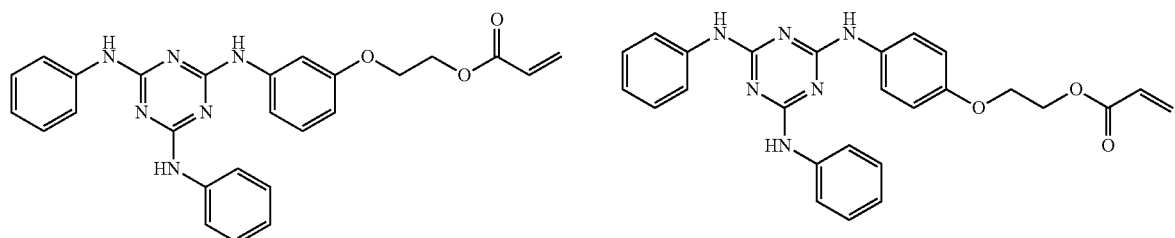
[Compound 67]
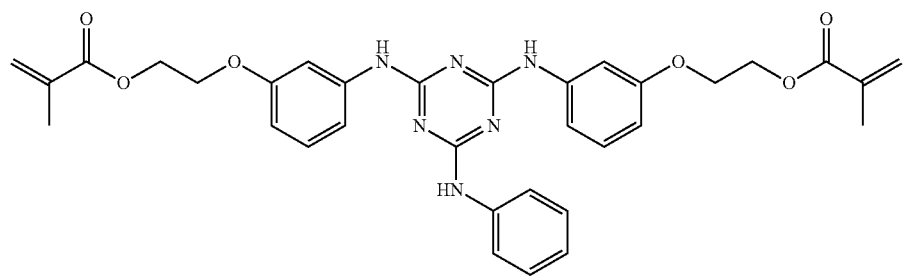
[Compound 68]
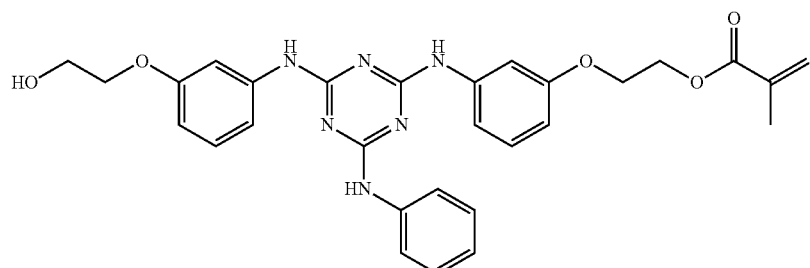
[Compound 69]
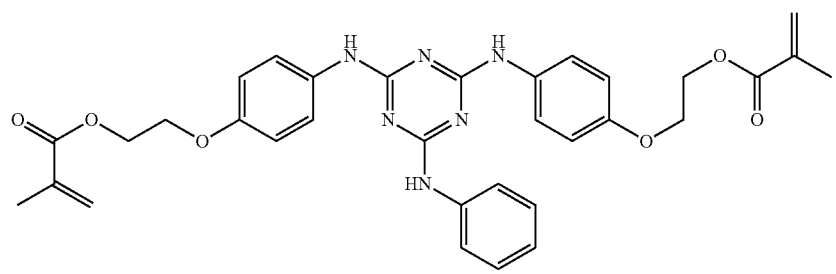

[Compound 70]
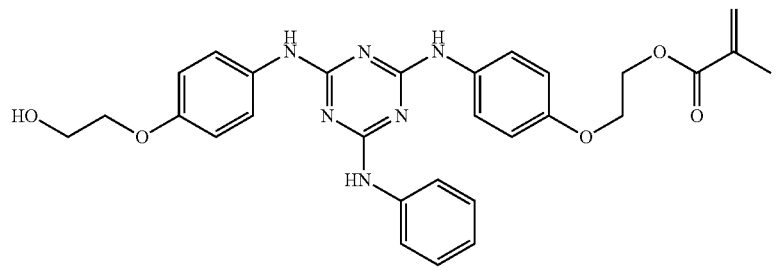
[Compound 71] [Compound 72]
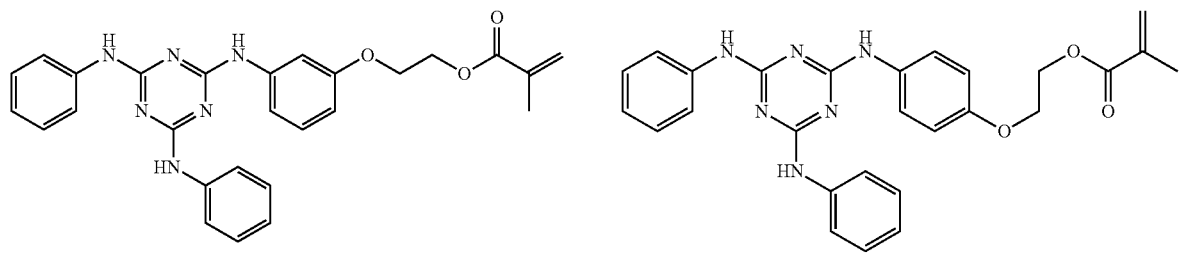
[Compound 73] [Compound 74]
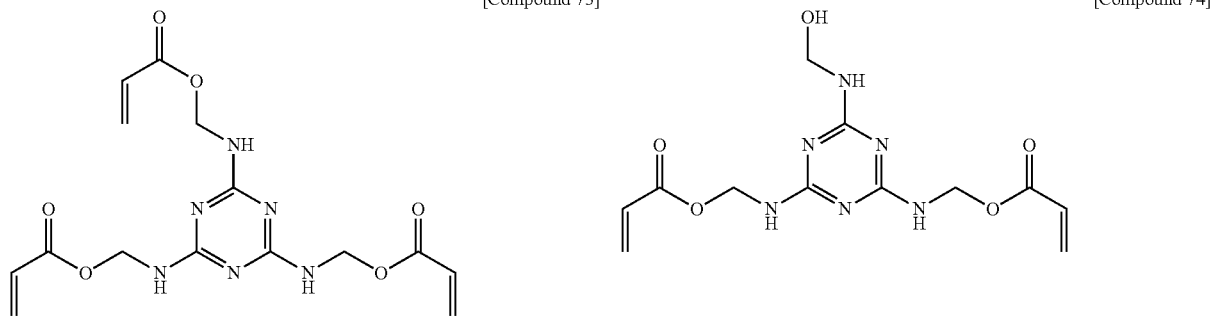
[Compound 75] [Compound 76]
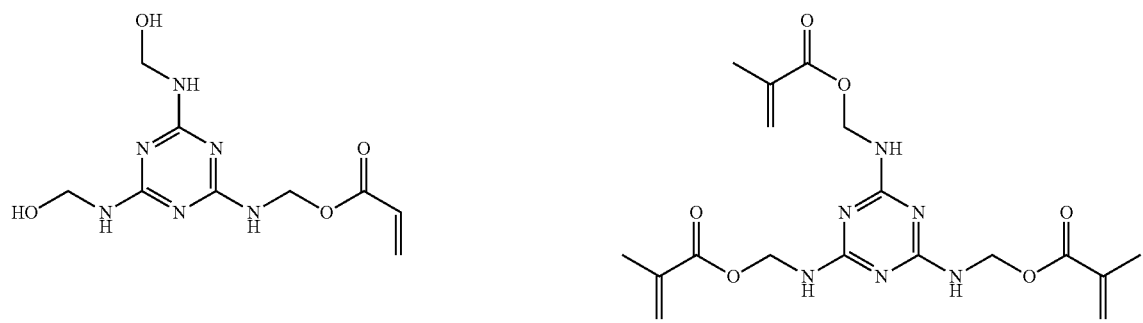
[Compound 77] [Compound 78]
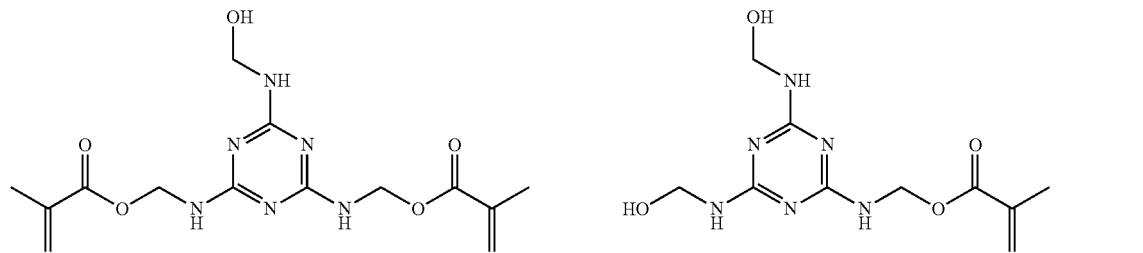

-continued
[Compound 79]
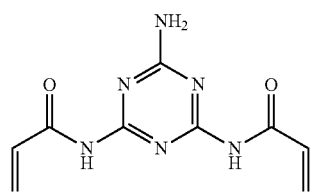
[Compound 80]
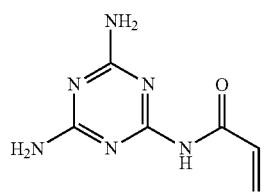
[Compound 81]
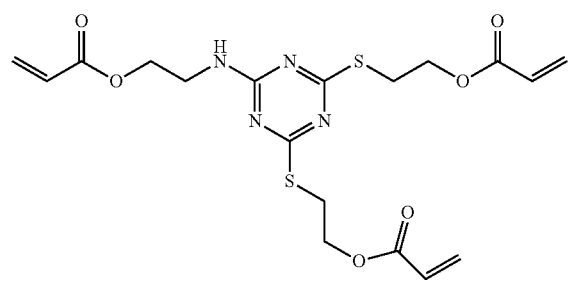
[Compound 82]
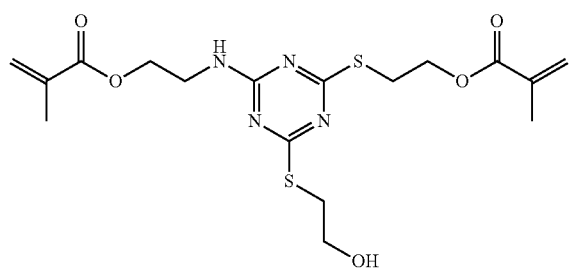
[Compound 83]
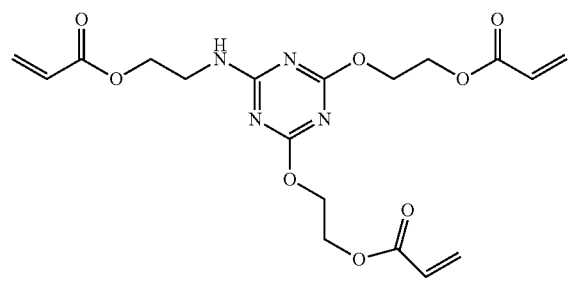
[Compound 84]
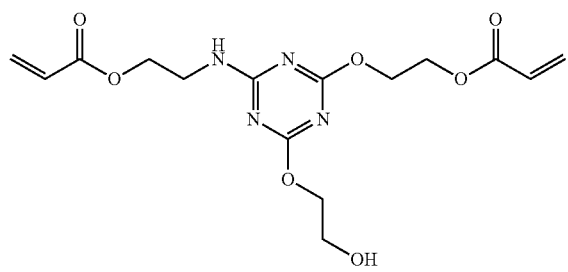
[Compound 85]
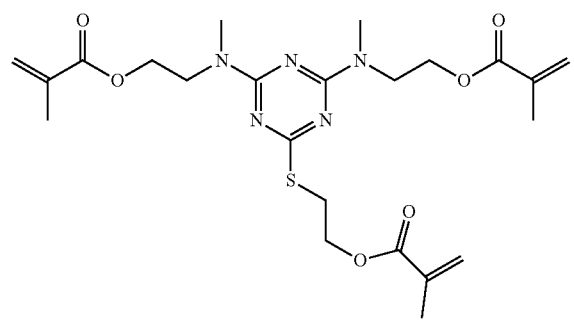
[Compound 86]
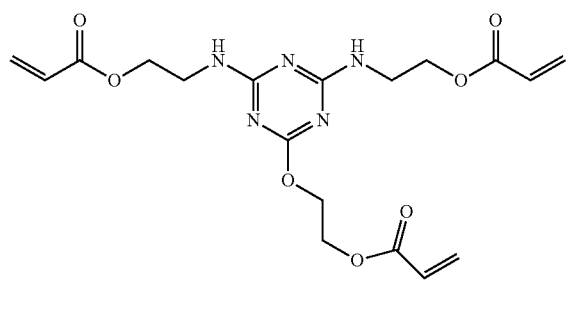
[Compound 87]
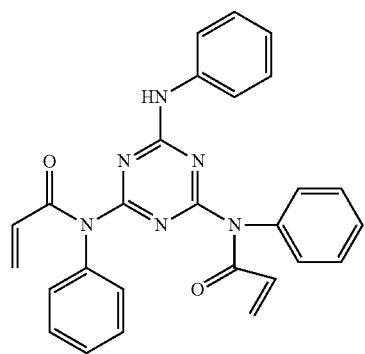
[Compound 88]
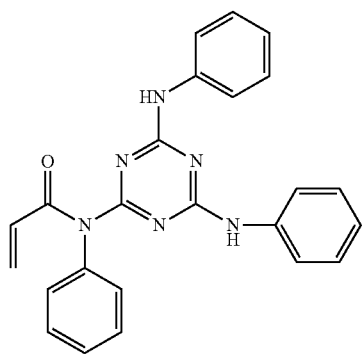

-continued
[Compound 89]
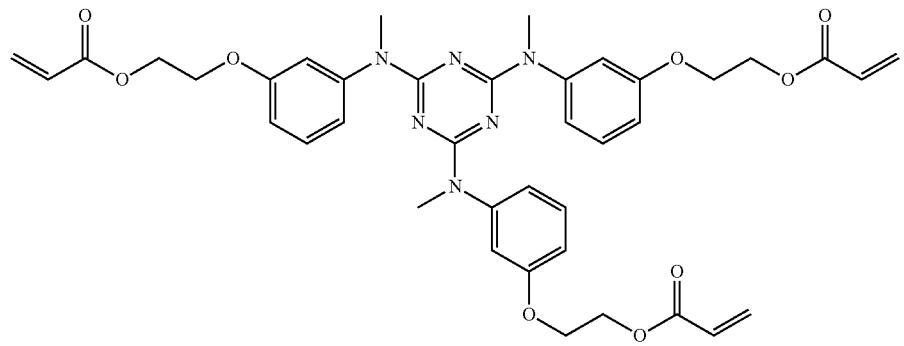
[Compound 90]
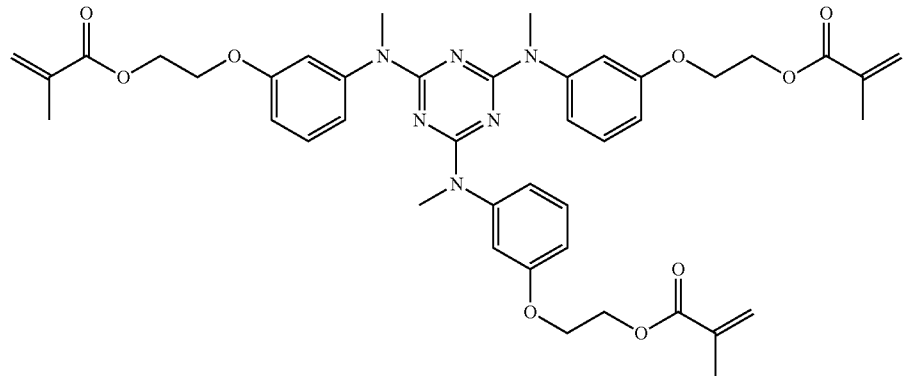
[Compound 91]
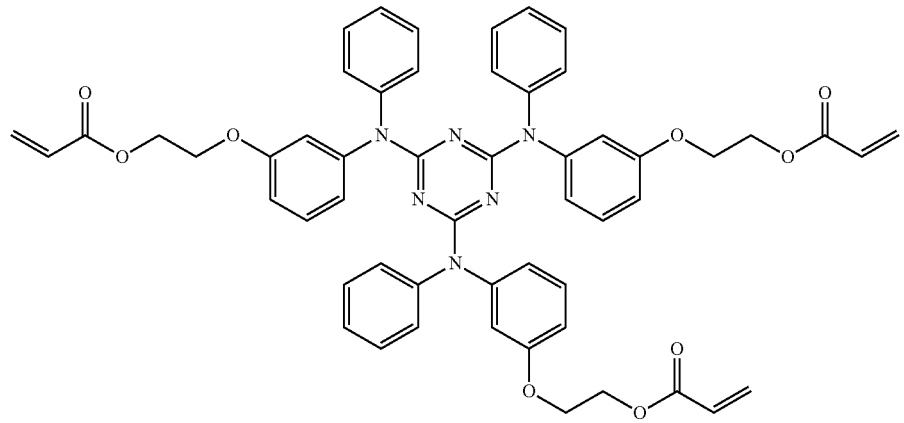
[Compound 92]
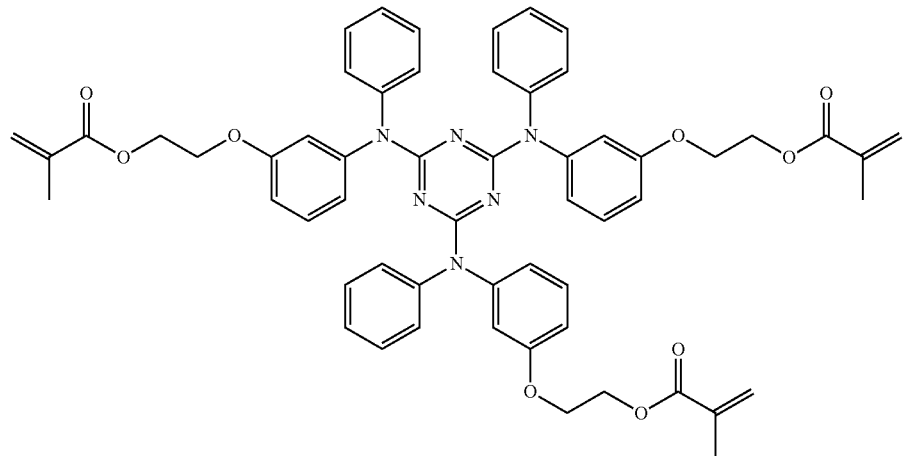

[Compound 93]
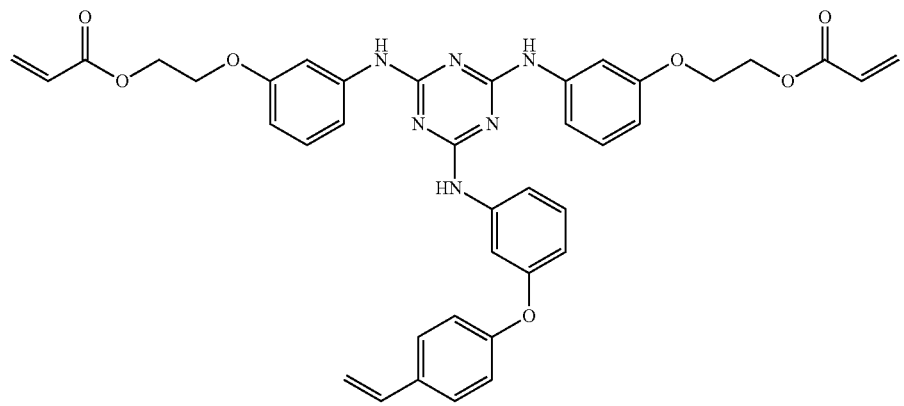
[Compound 94]
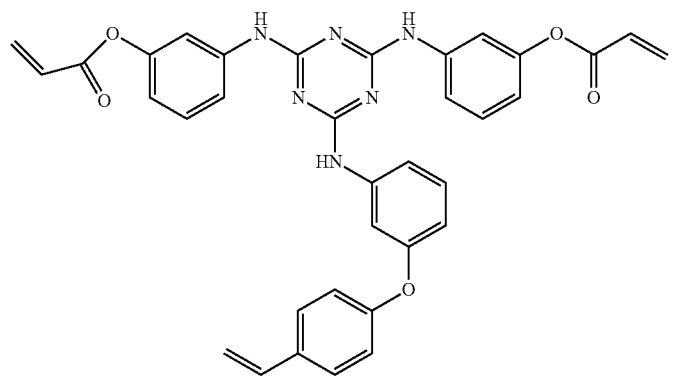
[Compound 95]
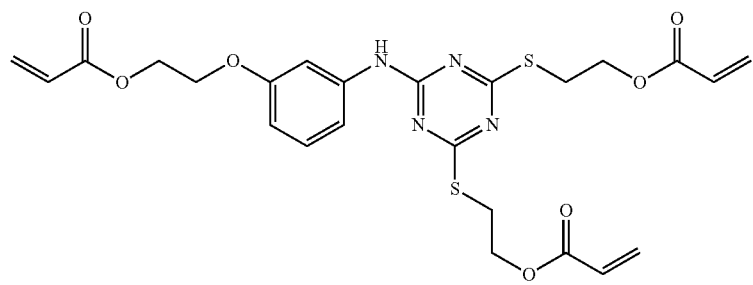
[Compound 96]
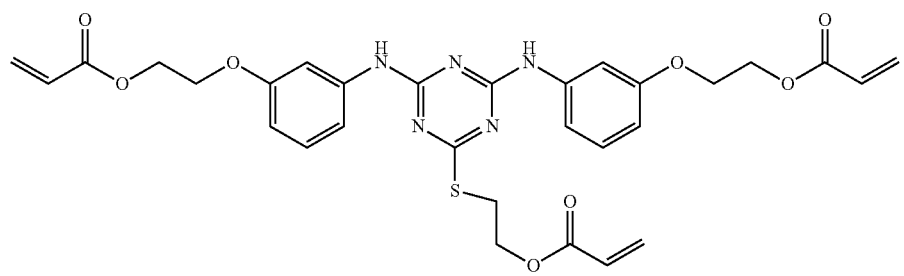
[Compound 97]
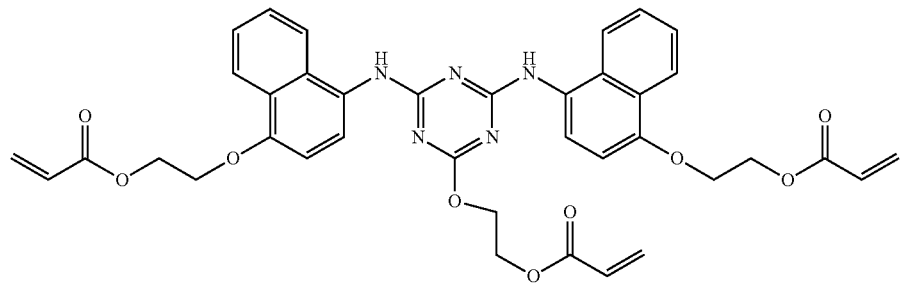

[Compound 98]
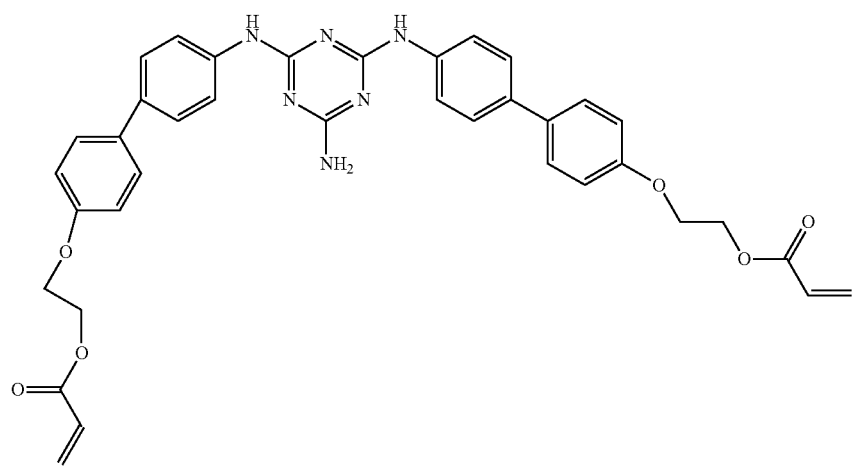
[Compound 99]
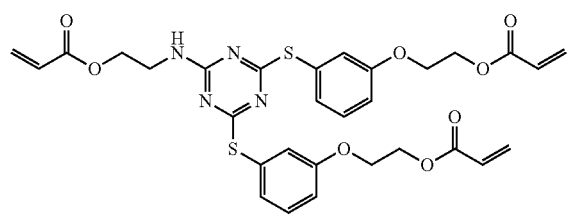
[Compound 100]
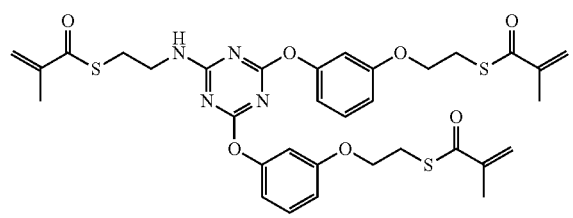
[Compound 101]
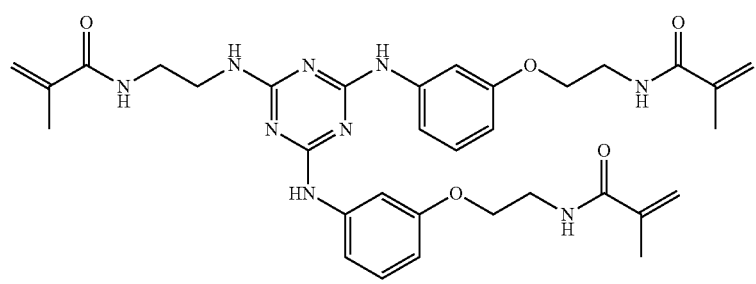
[Compound 102]
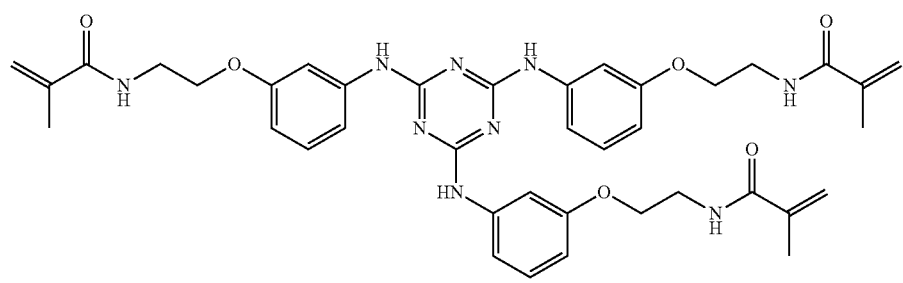

[Compound 103]
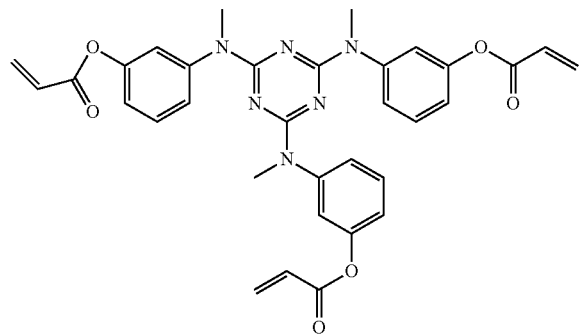
[Compound 104]
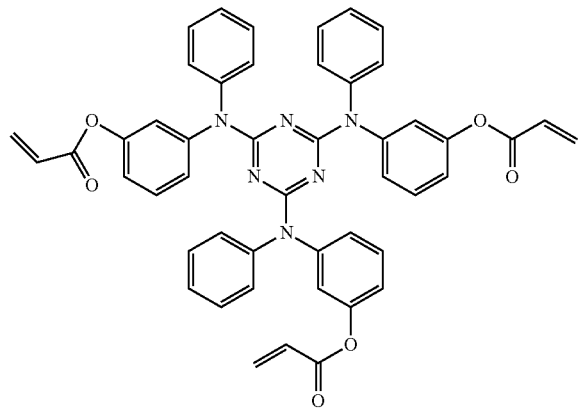
[Compound 105]
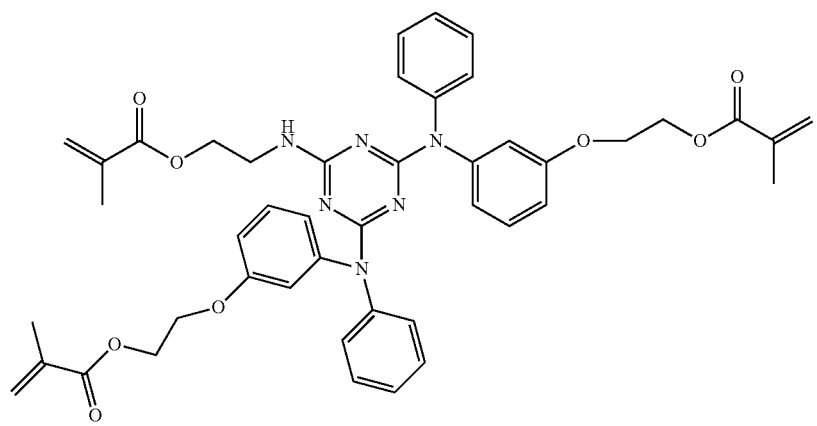
[Compound 106]
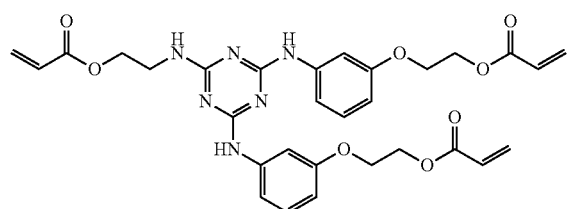
[Compound 107]
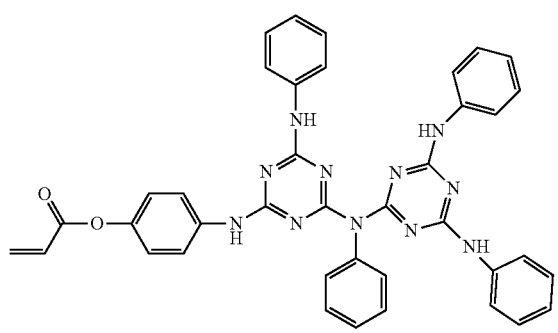
[Compound 108]
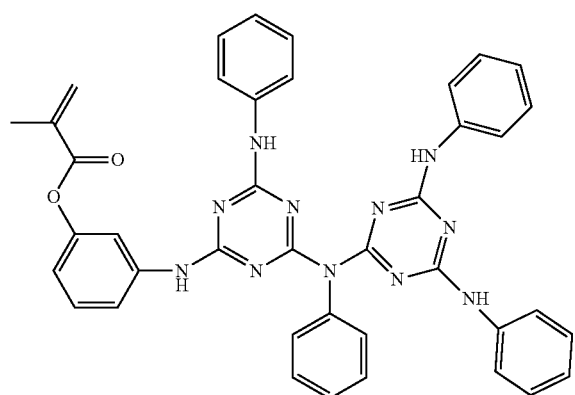

[Compound 109]
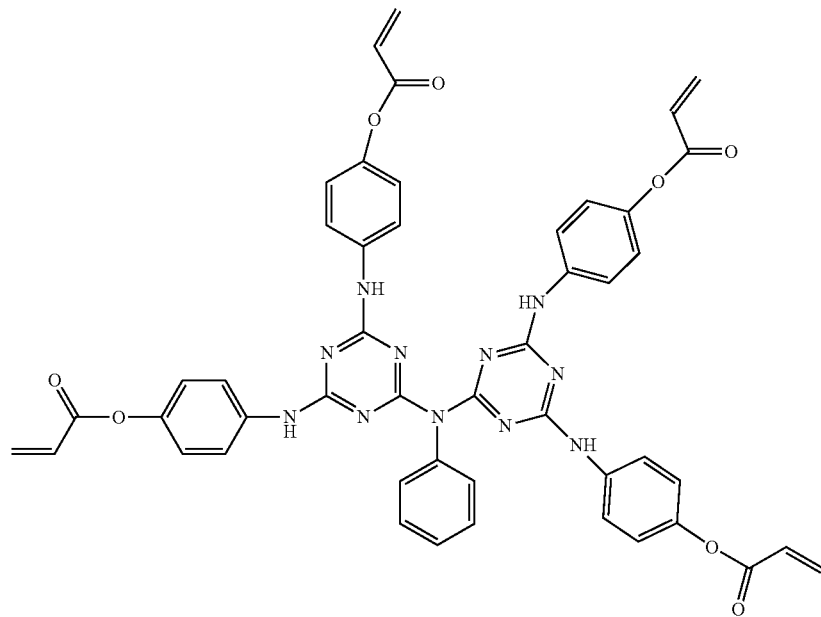
[Compound 110]
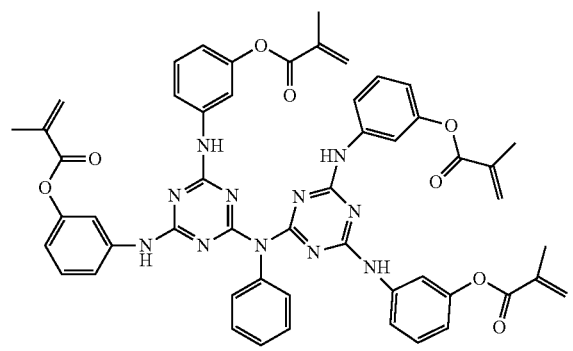
[Compound 111]
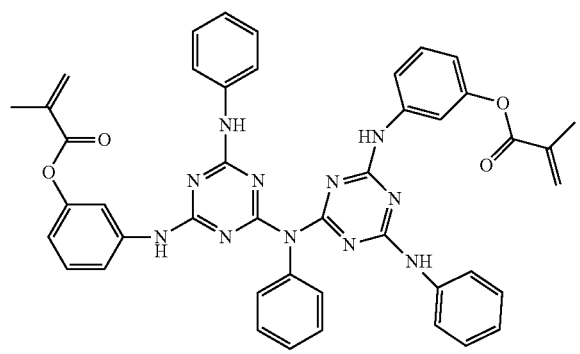
[Compound 112]
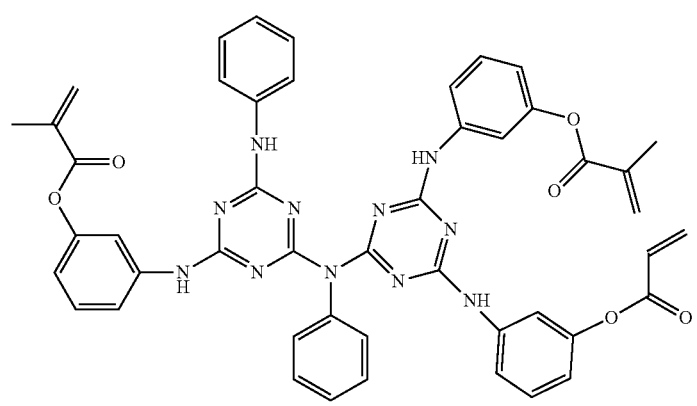

-continued
[Compound 113]
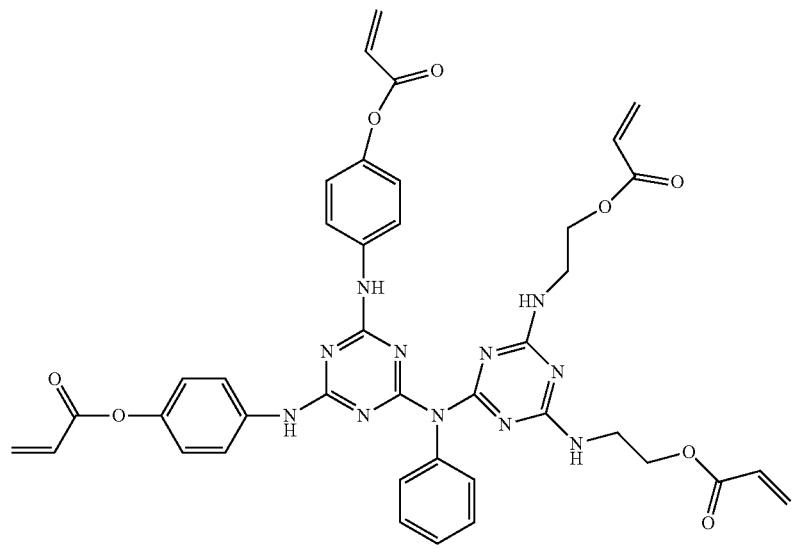
[Compound 114]
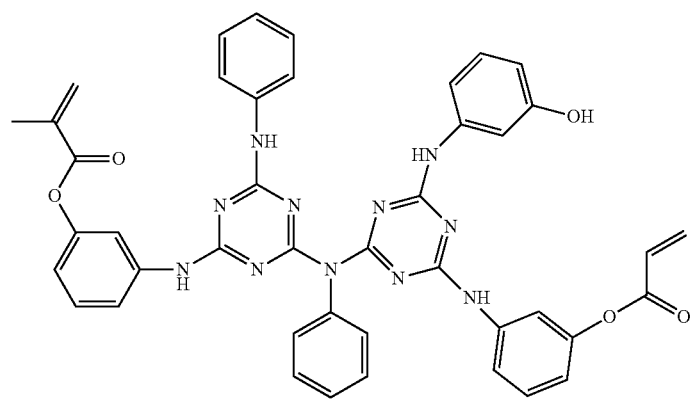
[Compound 115]
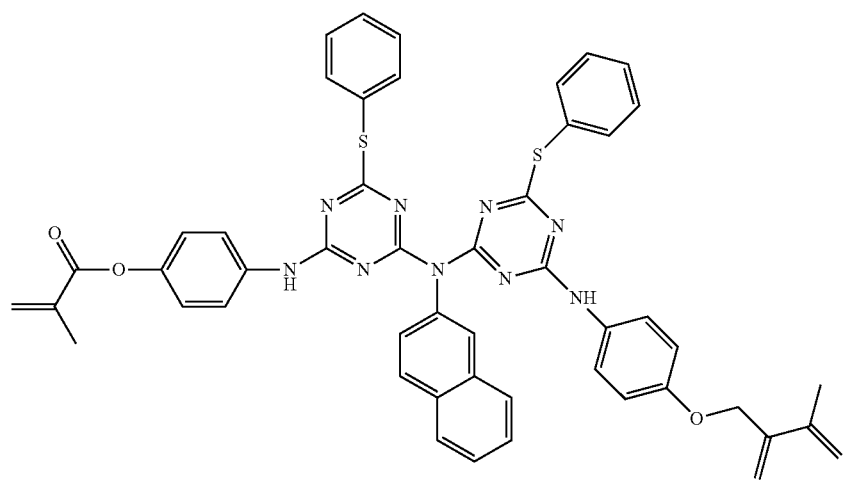

[Compound 116]
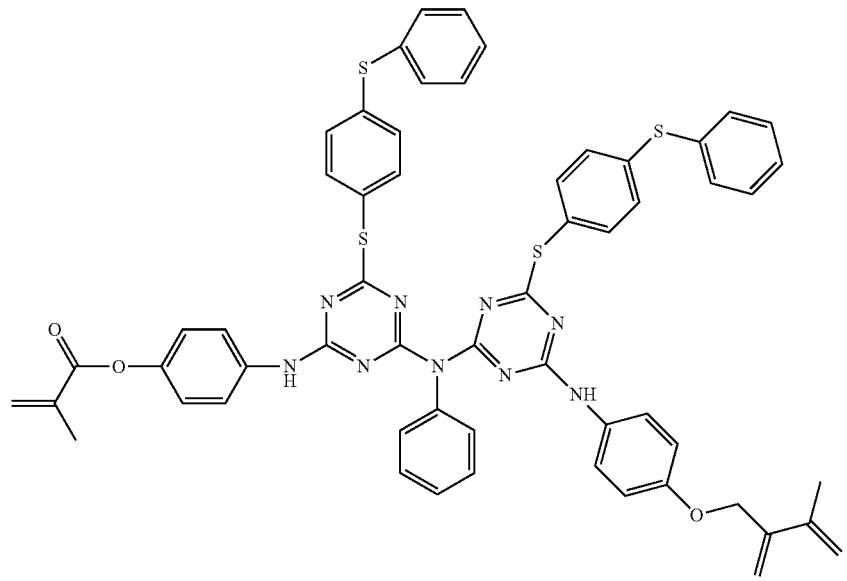
[Compound 117]
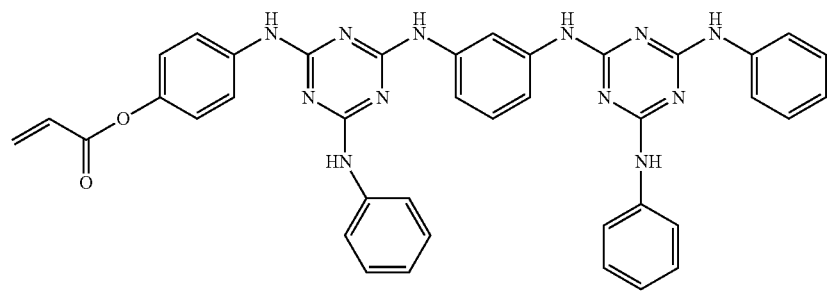
[Compound 118]
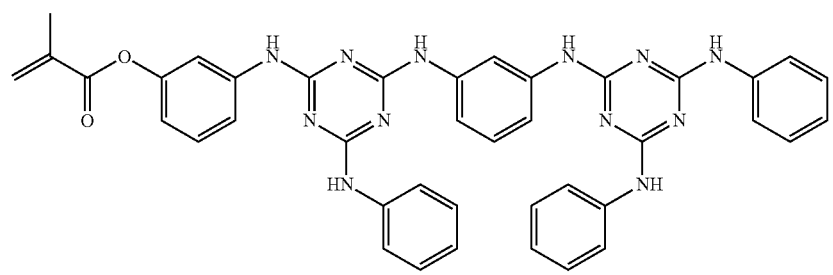
[Compound 119]
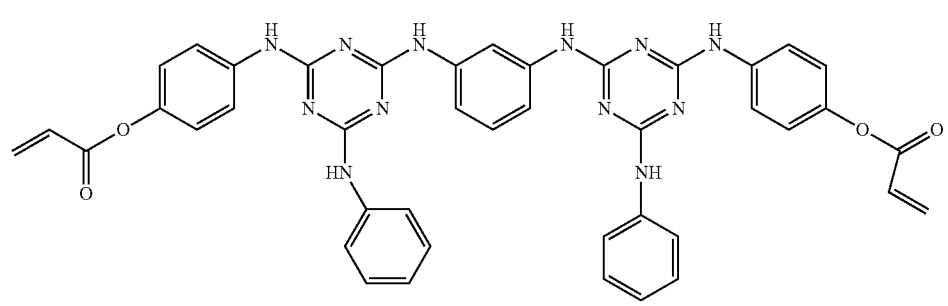

[Compound 120]
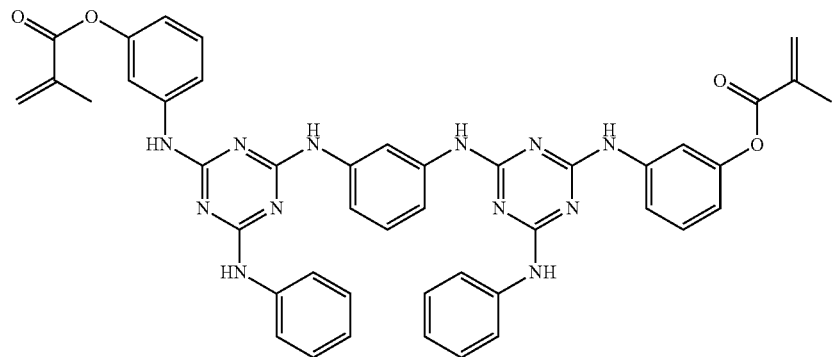
[Compund 121]
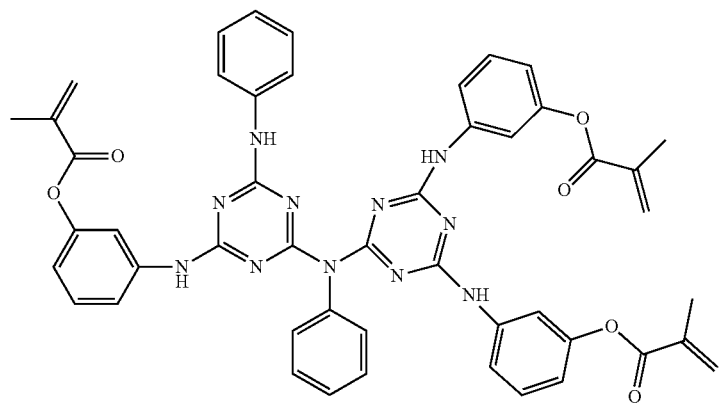
[Compound 122]
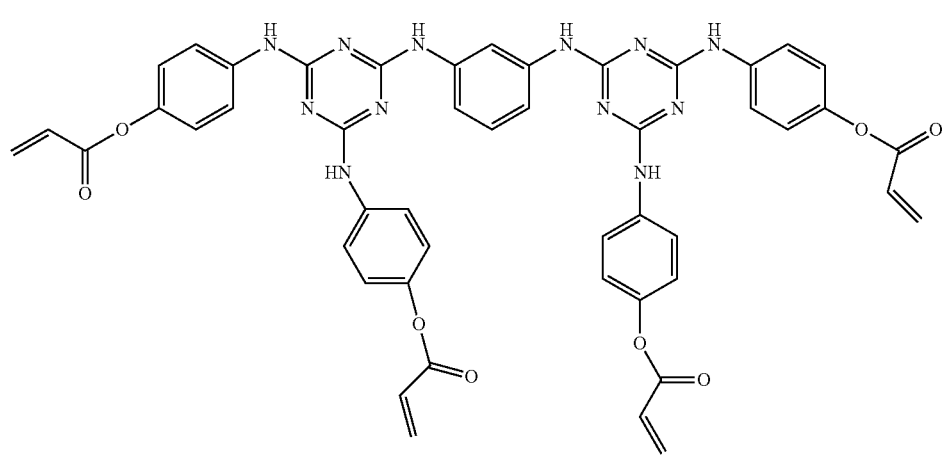

-continued
[Compound 123]
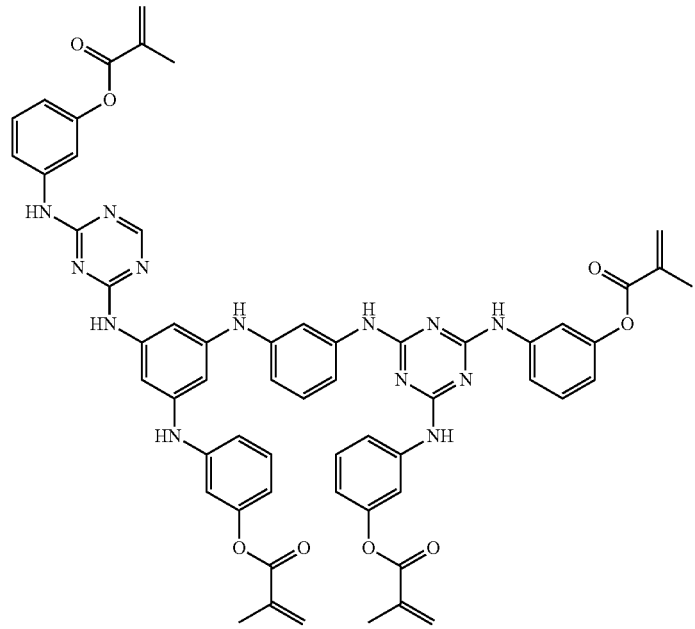
[Compound 124]
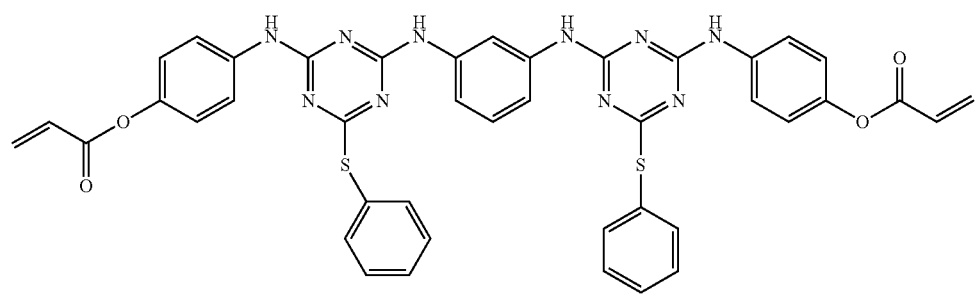
[Compound 125]
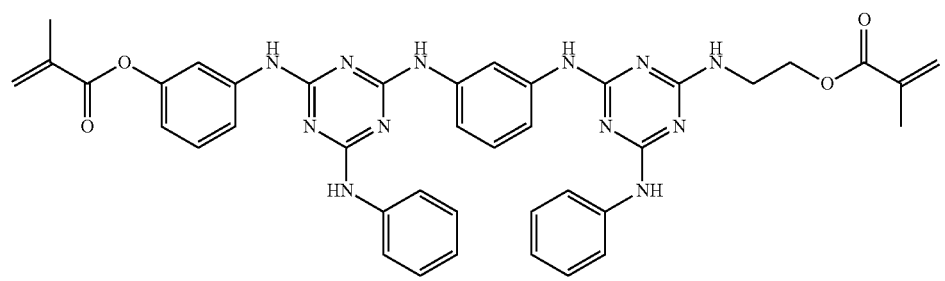
[Compound 126]
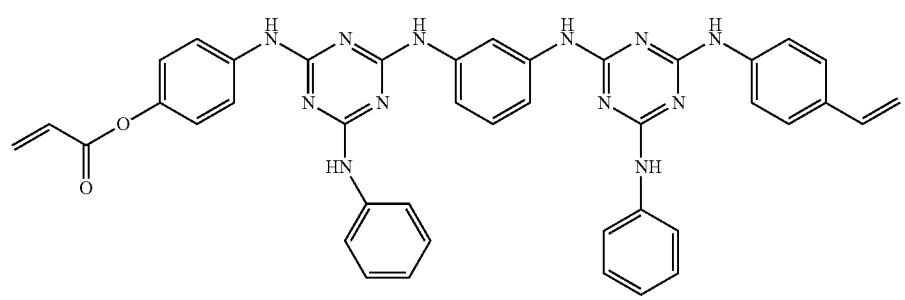

-continued
[Compound 127]
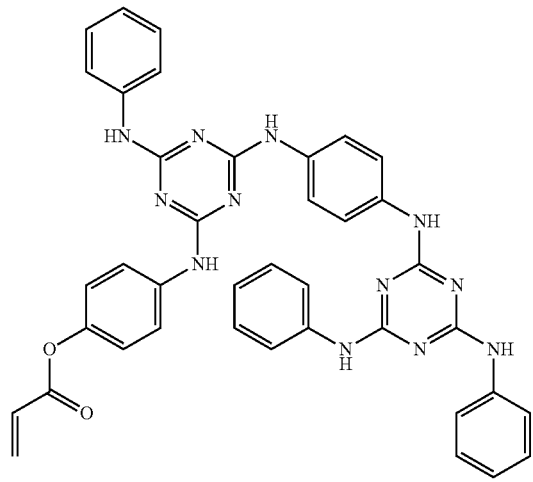
[Compound 128]
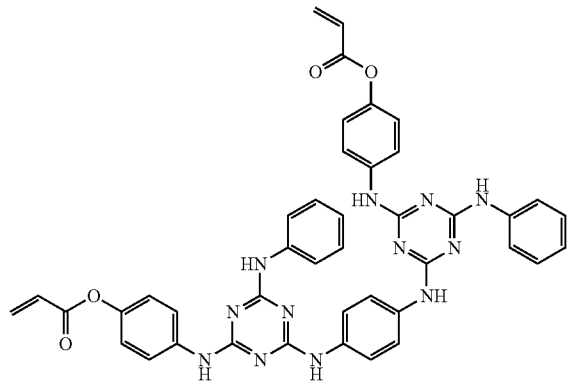
[Compound 129]
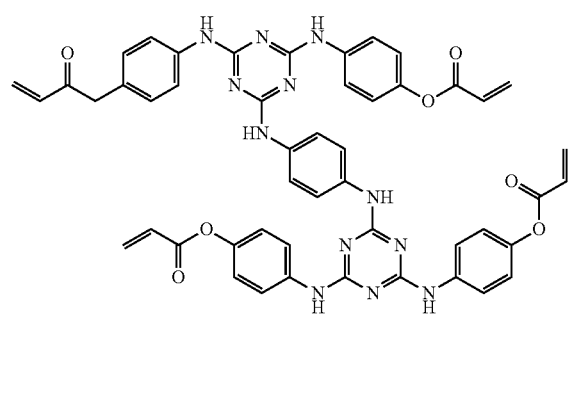
[Compound 130]
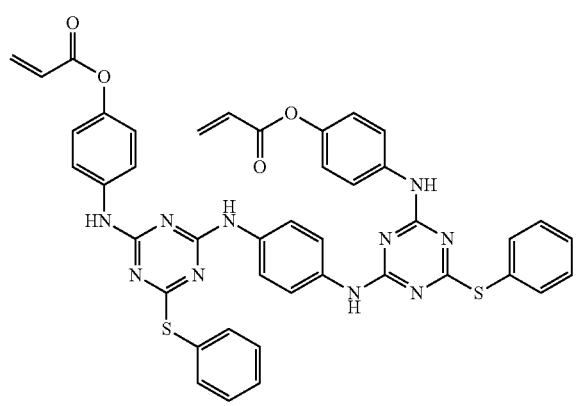
[Compound 131]
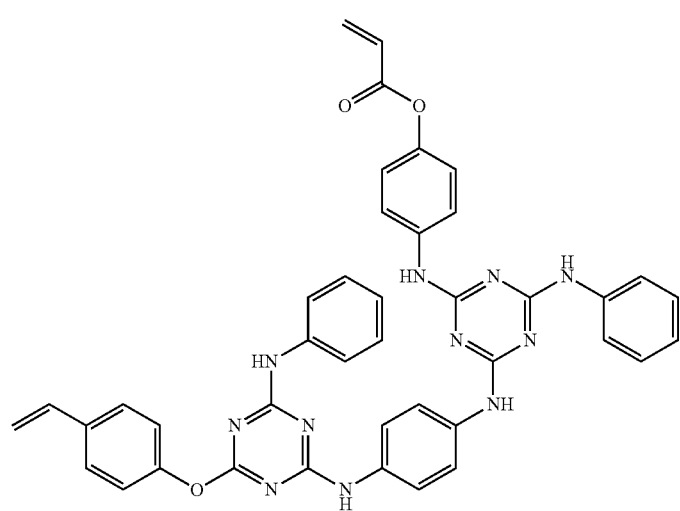

[Compound 132]

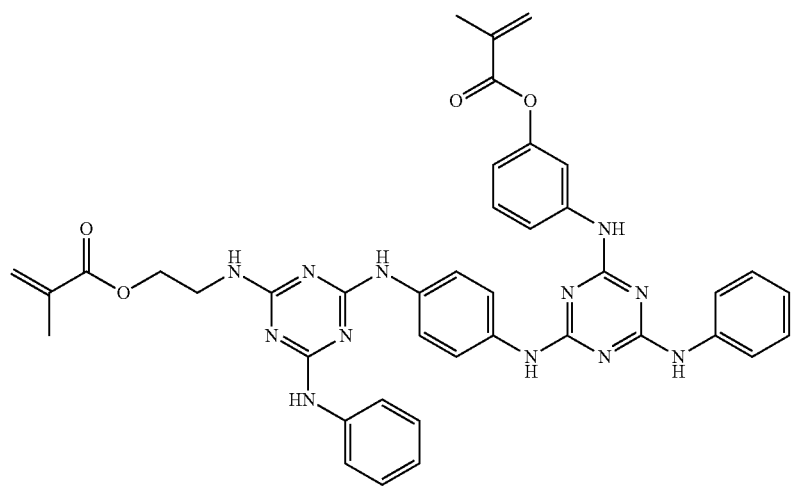

[Compound 133]

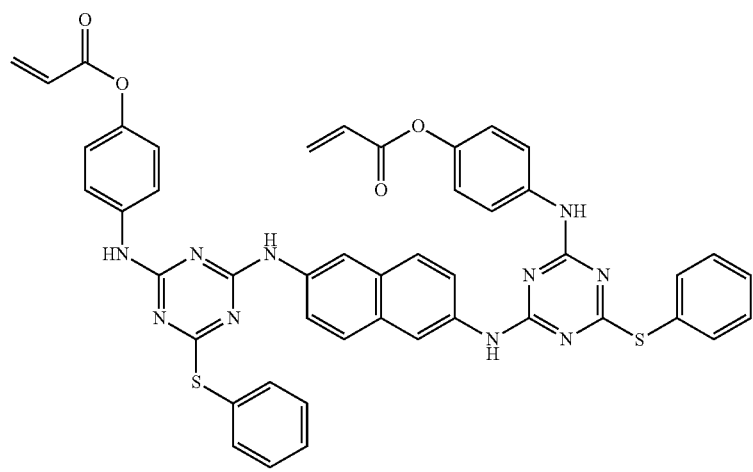

[Compound 134]

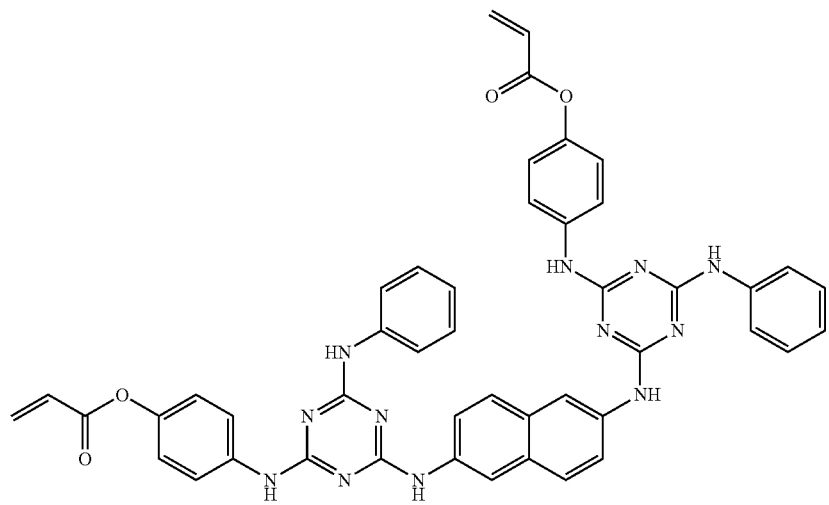

In addition, the present disclosure provides a photosensitive composition comprising a compound represented by any one of [Chemical Formula A] to [Chemical Formula C].

That is, the compound represented by any one of [Chemical Formula A] to [Chemical Formula C] according to the present disclosure may be contained as a photopolymerizable monomer in a photosensitive composition which can be prepared into a thin film or prism by light such as UV light. When used in compositions for display devices or electronic materials, the compound is highly compatible with solvents or acryl monomers.

Being also superior in terms of refractive index, transmittance, and anti-yellowing properties, the compound represented by any one of [Chemical Formula A] to [Chemical Formula C] can enhance the luminance and performance of TFT-LCD and OLED when used as a high refractive index monomer therein.

Meanwhile, the photosensitive composition may further comprise a photoinitiator or a photopolymerizable monomer and other materials known to be used in a photosensitive composition, without limitations.

Furthermore, the present disclosure provides an optical product article obtained by polymerizing the photosensitive composition.

In an embodiment of the present disclosure, the photosensitive composition may comprise 1 to 95 parts by weight of the compound represented by any one of [Chemical Formula A] to [Chemical Formula C], 0 to 90 parts by weight of a photopolymerizable compound, and 0.1 to 20 parts by weight of a photoinitiator.

Here, the photopolymerizable compound is a compound bearing one or more acryl, methacryl, or vinyl groups that is crosslinked by a reactive species that the photoinitiator creates when exposed to radiation such as UV. The photopolymerizable compound may be an alkyl acrylate, such as hexyl (meth)acrylate, cyclohexyl (meth)acrylate, tetradecyl (meth)acrylate, and hexadecy (meth)acrylate; or at least one selected from the group consisting of alkyl methacrylate, ethylene glycoldi(meth)acrylate, pentaerythritoltri(meth) acrylate, pentaerythritoltetra(meth)acrylate, pentaerythritolpenta(meth)acrylate, dipentaerythritolhexa(meth)acrylate, trimethylolpropanedi(meth)acrylate, trimethylolpropanetri (meth)acrylate, acrylic acid, methacrylic acid, glycidyl acrylate, and styrene.

Available as the photoinitiator are ketones, ketoacetals, thioxanthones, phosphine oxides, anthraquinones, trichloromethyl triazines, and oxime esters. Concrete examples of the photoinitiator include phenyl biphenyl ketone, thioxanthone, isopropyl thioxanthone, diethyl thioxanthone, benzophenone, 1-benzyl-1-dimethylamino-1-(4-morpholino-benzoyl)propane, 1-hydroxy-1-benzoyl cyclohexane, 2-morpholyl-2-(4-methylmercapto)benzoyl propane, ethyl anthraquinone, 4-benzoyl-4-methyldiphenyl sulfide, benzoin butyl ether, 2-hydroxy-2-benzoylpropane, 2-hydroxy-2-(4-isopropyl)benzoyl propane, 4-butylbenzoyl trichloromethane, 4-phenoxybenzoyl dichloromethane, diphenyl-2,4,6-trimethylbenzoyl phosphine oxide, benzoylformic acid methyl, 1,7-bis(9-acrydinyl)heptane, 2-methyl-4,6-bis (trichloromethyl)-s-triazine, 2-phenyl-4,6-bis(trichloromethyl)-s-triazine, 2-naphthyl-4,6-bis (trichloromethyl)-s-triazine, 1-[9-ethyl-6-(2-methylbenzoyl)-9H-carbazol-3-yl]-ethanone-1-(O-acetyl oxime), 1-(o-acetyl oxime)-1-[9-ethyl-6-(2-methylbenzoyl)-9H-carbazol-3-yl]ethanone, and 2-(o-benzoyl oxime)-1-[4-(phenylthio)phenyl]-1,2-octane-dione.

The photoinitiator may be used in an amount of 0.1 to 20 parts by weight and preferably in an amount of 0.1 to 10 parts by weight, based on 100 parts by weight of the photosensitive composition.

In addition, an organic solvent may be selectively used to dissolve the photosensitive composition, with the aim of adjusting viscosity and improving coating properties.

The organic solvent may be preferably at least one selected from ethyl acetate, butyl acetate, diethylene glycol dimethylether, diethylene glycol dimethylethylether, methyl methoxypropionate, ethyl ethoxypropionate (EEP), ethyl lactate, propylene glycol methylether acetate (PGMEA), propylene glycol methylether, propylene glycol propylether, methyl cellosolve acetate, ethyl cellosolve acetate, diethylene glycol methyl acetate, diethylene glycol ethyl acetate, acetone, methyl isobutyl ketone, cyclohexanone, dimethyl formamide (DMF), N,N-dimethyl acetamide (DMAc), N-methyl-2-pyrrolidone (NMP), γ-butyrolactone, diethyl ether, ethylene glycol dimethyl ether, diglyme, tetrahydrofuran (THF), methanol, ethanol, propanol, iso-propanol, methyl cellosolve, ethyl cellosolve, diethylene glycol methyl ether, diethylene glycol ethyl ether, dipropylene glycol methyl ether, toluene, xylene, hexane, heptane, and octane. The content of the solvent may preferably range from 0 to 90 parts by weight, based on 100 parts by weight of the photosensitive composition.

In addition, the photosensitive composition according to the present disclosure may be used to manufacture prism sheets, microlenses, coating materials for LCDs, DBEF films, coating materials for OLEDs, optical lenses, or multifocal lenses.

Hereinafter, the present disclosure will be described in more detail with reference to Examples. These examples are only for illustrating the present invention, it will be apparent to those skilled in the art that the scope of the present disclosure is not limited by these examples.

The compound with an acrylic group, represented by any one of [Chemical Formula A], [Chemical Formula B], and [Chemical Formula C] can be synthesized as illustrated in the following representative Reaction Scheme 1.

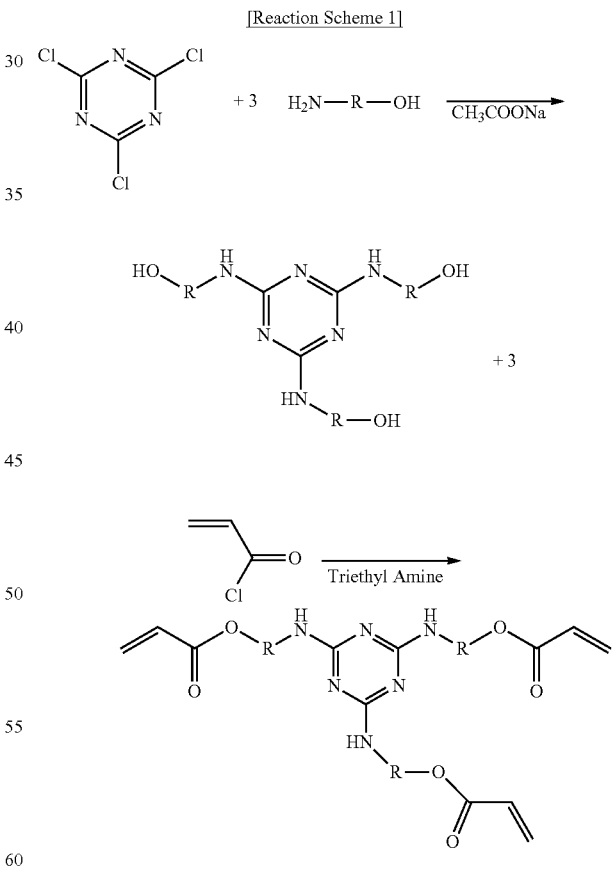

Reaction Scheme 1 accounts for a synthesis mechanism for a part of the compound having an acrylic group. With the suitable modification of the substituents, various compounds having an acryl group, represented by [Chemical Formula A], [Chemical Formula B], and [Chemical Formula C], can be synthesized.

Synthesis Example 1 Synthesis of Compound 2

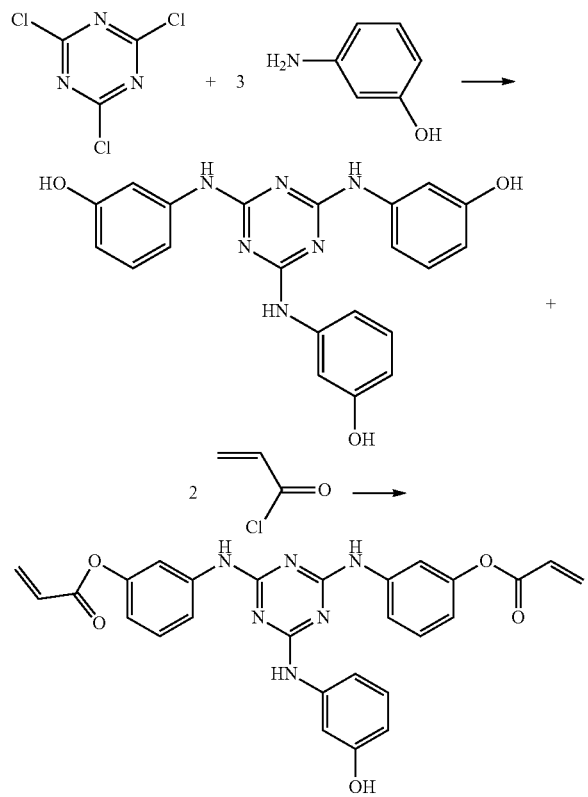

Synthesis Example 1-1: Synthesis of 3,3',3''-((1,3,5-triazine-2,4,6-triyl)tris(azanediyl)) triphenol In a 1-L reactor was placed THF (300 ml), followed by adding 2,4,6-trichloro-1,3,5-triazine (20.0 g, 108.5 mmol) under a nitrogen atmosphere. After the reactor was cooled to 0° C., 3-aminophenol (35.5 g, 325.4 mmol) was slowly added over 30 min while stirring. Sodium acetate (Molecular Weight: 82.03, 20.0 g, 244.0 mmol) was added to the reactor which was then heated to 80° C. at which stirring was continued for 10 hours. After completion of the reaction, distilled water (300 ml) was added and stirred to afford 3,3',3''-((1,3,5-triazine-2,4,6-triyl)tris(azanediyl))triphenol as a white solid (40.1 g, yield 92%).

Synthesis Example 1-2: Synthesis of Compound 2

To a 250-ml reactor were sequentially added THF (100 mL), triethylamine (30 ml), and 3,3',3''-((1,3,5-triazine-2,4,6-triyl)tris(azanediyl))triphenol (10.0 g, 24.9 mmol) which were then cooled to 0° C. under a nitrogen atmosphere. Acryloyl chloride (4.5 g, 49.7 mmol) was slowly added over 30 min to the reactor and stirred at room temperature for 5 hours. After completion of the reaction, extraction was conducted with distilled water and ethyl acetate. The organic layer thus formed was dried over MgSO$_4$. Concentration in a vacuum was followed by filtration using column chromatography with ethyl acetate:hexane=1:3 to afford [Compound 2] (11.5 g, yield 91%).

Synthesis Example 2: Synthesis of Compound 4

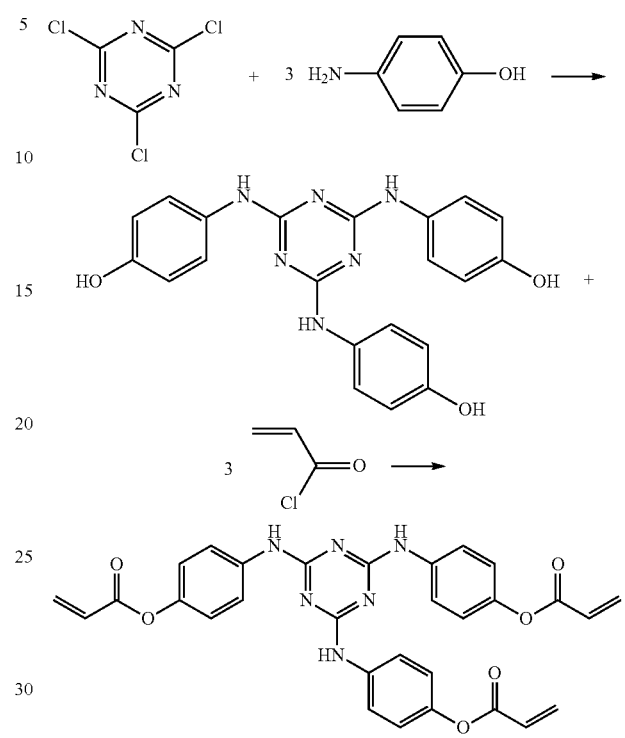

Synthesis Example 2-1: Synthesis of 4,4',4''-((1,3,5-triazine-2,4,6-triyl)tris(azanediyl)) triphenol In a 1-L reactor was placed THF (250 ml), followed by adding 2,4,6-trichloro-1,3,5-triazine (15.0 g, 81.3 mmol) under a nitrogen atmosphere. After the reactor was cooled to 0° C., 4-aminophenol (26.6 g, 244.0 mmol) was slowly added over 30 min while stirring. Sodium acetate (20.0 g, 244.0 mmol) was added to the reactor which was then heated to 80° C. at which stirring was continued for 10 hours. After completion of the reaction, distilled water (250 ml) was added and stirred to afford 4,4',4'''-((1,3,5-triazine-2,4,6-triyl)tris(azanediyl))triphenol as a white solid (30.8 g, yield 94%).

Synthesis Example 2-2: Synthesis of Compound 4

To a 250-ml reactor were sequentially added THF (100 mL), triethylamine (30 ml), and 4,4',4'-((1,3,5-triazine-2,4,6-triyl)tris(azanediyl))triphenol (10.0 g, 24.9 mmol) which were then cooled to 0° C. under a nitrogen atmosphere. Acryloyl chloride (7.4 g, 82.2 mmol) was slowly added over 30 min to the reactor and stirred at room temperature for 5 hours. After completion of the reaction, extraction was conducted with distilled water and ethyl acetate. The organic layer thus formed was dried over MgSO$_4$. Concentration in a vacuum was followed by filtration using column chromatography with ethyl acetate:hexane=1:3 to afford [Compound 4] (12.5 g, yield 89%).

Synthesis Example 3: Synthesis of Compound 12

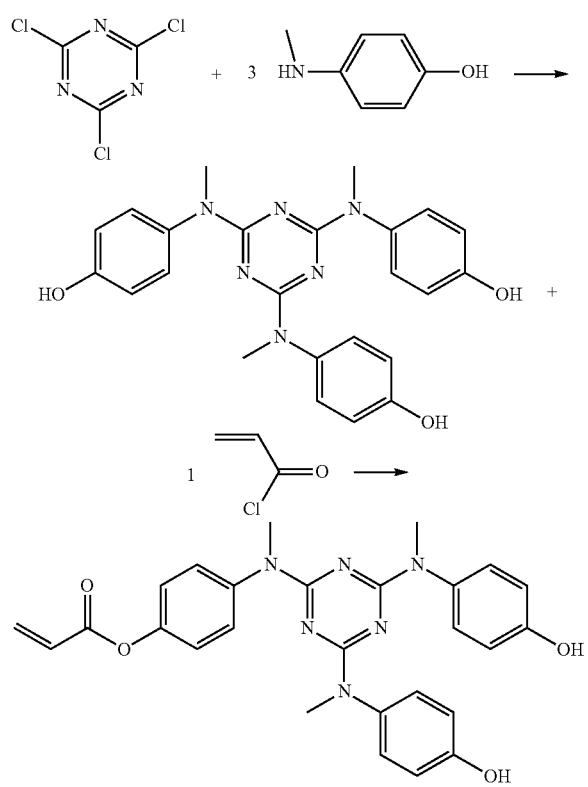

Synthesis Example 3-1: Synthesis of 4,4',4"-((1,3,5-triazine-2,4,6-triyl)tris(methylazanediyl)) triphenol In a 500-mL reactor was placed THF (150 ml), followed by adding 2,4,6-trichloro-1,3,5-triazine (10.0 g, 54.2 mmol) under a nitrogen atmosphere. After the reactor was cooled to 0° C., 4-(methylamino)phenol (20.0 g, 162.6 mmol) was slowly added over 30 min while stirring. Sodium acetate (13.3 g, 244.0 mmol) was added to the reactor which was then heated to 80° C. at which stirring was continued for 10 hours. After completion of the reaction, distilled water (150 ml) was added and stirred to afford 4,4',4"-((1,3,5-triazine-2,4,6-triyl)tris(methylazanediyl))triphenol as a white solid (21.7 g, yield 90%).

Synthesis Example 3-2: Synthesis of Compound 12

To a 250-ml reactor were sequentially added THF (120 mL), triethylamine (20 ml), and 4,4',4"-((1,3,5-triazine-2,4,6-triyl)tris(methylazanediyl))triphenol (12.0 g, 27.0 mmol) which were then cooled to 0° C. under a nitrogen atmosphere. Acryloyl chloride (2.4 g, 27.0 mmol) was slowly added over 30 min to the reactor and stirred at room temperature for 5 hours. After completion of the reaction, extraction was conducted with distilled water and ethyl acetate. The organic layer thus formed was dried over MgSO₄. Concentration in a vacuum was followed by filtration using column chromatography with ethyl acetate:hexane=1:3 to afford [Compound 12] (10.4 g, yield 93%).

Synthesis Example 4: Synthesis of Compound 25

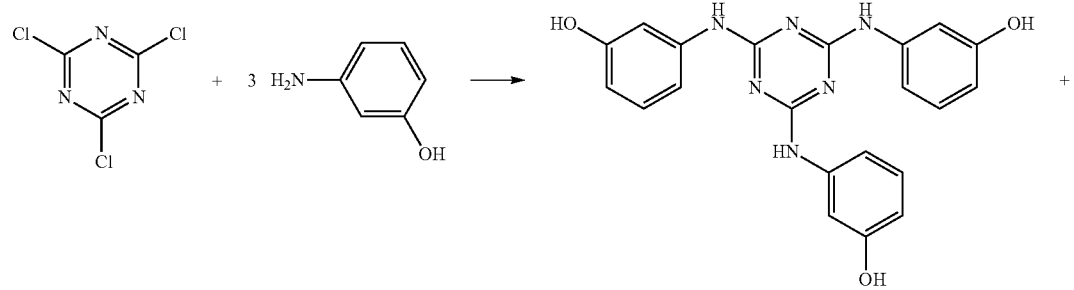

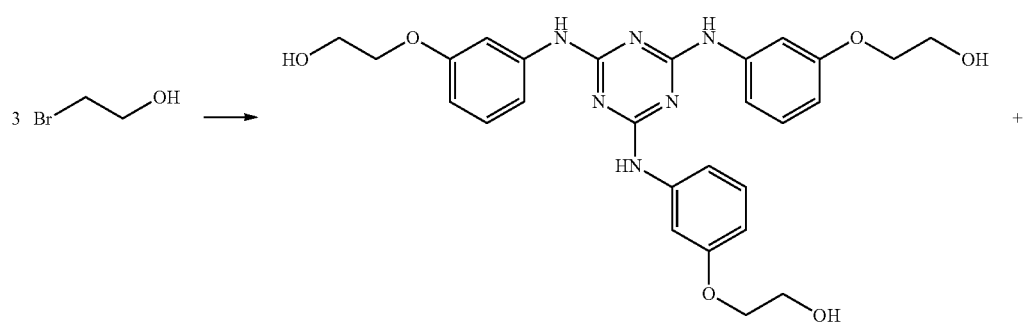

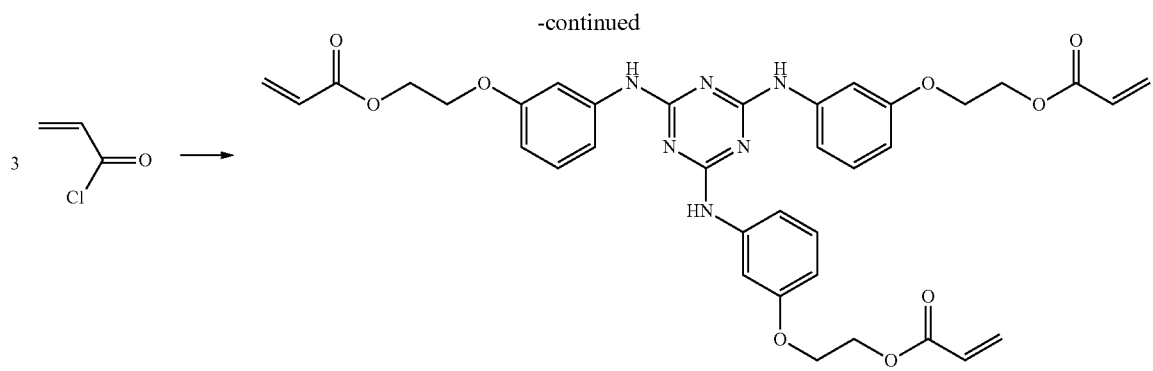

Synthesis Example 4-1: Synthesis of 3,3',3"-((1,3,5-triazine-2,4,6-triyl)tris(azanediyl)) triphenol The title compound was synthesized in the same manner as in Synthesis Example 1-1.

Synthesis Example 4-2: Synthesis of 2,2',2'-((((1,3,5-triazine-2,4,6-triyl)tris(azanediyl)) tris(benzene-3,1-diyl))tris(oxy))triethanol In a 250-mL reactor, 3,3',3' '-((1,3,5-triazine-2,4,6-triyl)tris(azanediyl))triphenol (10 g, 24.9 mmol) and $K_2CO_3$ (10.3 g, 74.7 mmol) were added to DMF (100 ml) under a nitrogen atmosphere. To the reactor was slowly added 2-bromoethanol (11.2 g, 89.5 mmol) over 30 min which was stirred at 80° C. for 10 hours. After completion of the reaction, extraction was conducted with distilled water and ethyl acetate. The organic layer thus formed was washed twice with distilled water. The organic layer was dehydrated with $MgSO_4$ and concentrated in a vacuum to afford 2,2',2"-((((1,3,5-triazine-2,4,6-triyl)tris(azanediyl))tris(benzene-3,1-diyl))tris (oxy)) triethanol as a white solid (12.8 g, yield 96%).

Synthesis Example 4-3: Synthesis of Compound 25

To a 500-ml reactor were sequentially added THF (200 mL), triethylamine (20 ml), and 2,2',2"-((((1,3,5-triazine-2,4,6-triyl)tris (azanediyl))tris(benzene-3,1-diyl))tris(oxy)) triethanol (20.0 g, 37.4 mmol) which were then cooled to 0° C. under a nitrogen atmosphere. Acryloyl chloride (10.2 g, 112.2 mmol) was slowly added over 30 min to the reactor and stirred at room temperature for 15 hours. After completion of the reaction, extraction was conducted with distilled water and ethyl acetate. The organic layer thus formed was dried over $MgSO_4$. Concentration in a vacuum was followed by filtration using column chromatography with ethyl acetate:hexane=1:4 to afford [Compound 25] (22.2 g, yield 85%).

Synthesis Example 5: Synthesis of Compound 40

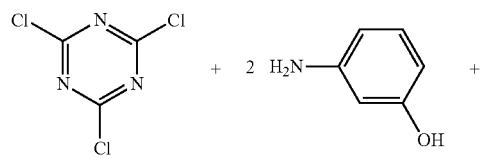

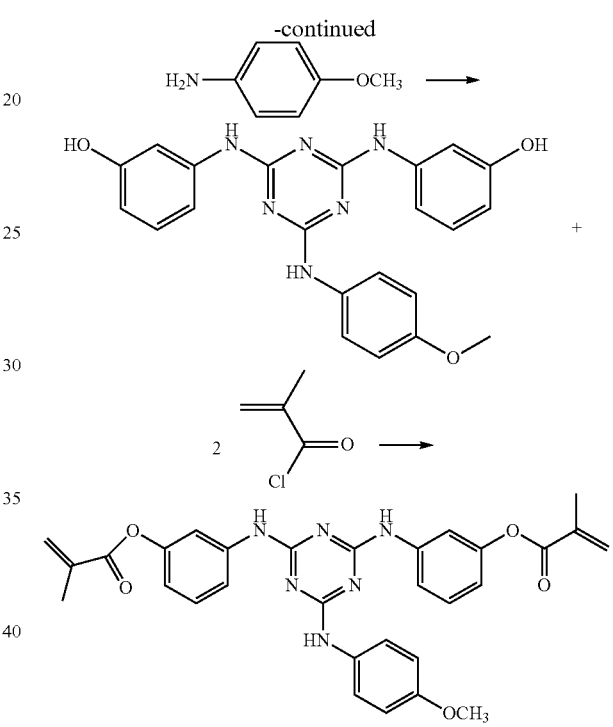

Synthesis Example 5-1: Synthesis of 3,3'-((6-(phenylamino)-1,3,5-triazine-2,4-diyl)bis (azanediyl)) diphenol In a 500-mL reactor, 2,4,6-trichloro-1,3,5-triazine (12.0 g, 65.1 mmol) was added to THF (120 ml) under a nitrogen atmosphere. To the reactor that was cooled to 0° C., 3-aminophenol (14.2 g, 130.2 mmol) and 4-methoxyaniline (8.0 g, 65.1 mmol) were each slowly added over 30 min in the order while stirring, followed by sodium acetate (16.0 g, 195.3 mmol). The reactor was heated to 80° C. before 10 hours of stirring. After completion of the reaction, distilled water (120 ml) was added. Stirring formed a white solid of 3,3'-((6-((4-methoxyphenyl)amino)-1,3,5-triazine-2,4-diyl) bis(azanediyl))diphenol (22.8 g, yield 84%).

Synthesis Example 5-2: Synthesis of Compound 40

To a 250-ml reactor were sequentially added THF (100 mL), triethylamine (20 ml), and 3,3'-((6-((4-methoxyphenyl)amino)-1,3,5-triazine-2,4-diyl)bis(azanediyl))diphenol (8.0 g, 19.2 mmol) which were then cooled to 0° C. under a nitrogen atmosphere. Methacryloyl chloride (4.0 g, 38.4 mmol) was slowly added over 30 min to the reactor and stirred at room temperature for 5 hours. After completion of the reaction, extraction was conducted with distilled water and ethyl acetate. The organic layer thus formed was dried over MgSO₄. Concentration in a vacuum was followed by filtration using column chromatography with ethyl acetate:hexane=1:5 to afford [Compound 40] (10.4 g, yield 90%).

Synthesis Example 6: Synthesis of Compound 81

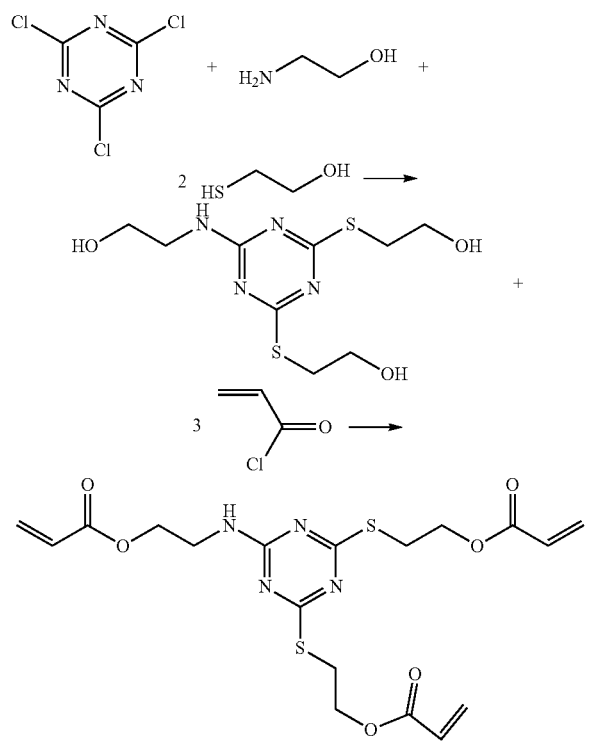

Synthesis Example 6-1: Synthesis of 2,2'-((6-((2-hydroxyethyl)amino)-1,3,5-triazine-2,4-diyl)bis (sulfanediyl)) diethanol In a 500-mL reactor, 2,4,6-trichloro-1,3,5-triazine (15.0 g, 81.3 mmol) was added to THF (150 ml) under a nitrogen atmosphere. To the reactor that was cooled to 0° C., 2-aminoethanol (5.0 g, 81.3 mmol) and 2-mercaptoethanol (12.7 g, 162.6 mmol) were each slowly added over 30 min in the order while stirring, followed by sodium acetate (20.0 g, 243.9 mmol). The reactor was heated to 80° C. before 15 hours of stirring. After completion of the reaction, extraction was conducted with distilled water and ethyl acetate. The organic layer was washed with distilled water and then dehydrated with MgSO₄. After evaporation of the solvent, column chromatography using EA and hexane at the ratio of 1:3 gave 2,2'-((6-((2-hydroxyethyl)amino)-1,3,5-triazine-2,4-diyl)bis(sulfanediyl)) diethanol (18.6 g, yield 78%).

Synthesis Example 6-2: Synthesis of Compound 81

To a 250-ml reactor were sequentially added THF (120 mL), triethylamine (30 ml), and 2,2'-((6-((2-hydroxyethyl) amino)-1,3,5-triazine-2,4-diyl)bis(sulfanediyl))diethanol (12.0 g, 41.0 mmol) which were then cooled to 0° C. under a nitrogen atmosphere. Acryloyl chloride (11.1 g, 123.1 mmol) was slowly added over 30 min to the reactor and stirred at room temperature for 10 hours. After completion of the reaction, extraction was conducted with distilled water and ethyl acetate. The organic layer thus formed was dried over MgSO₄. Concentration in a vacuum was followed by filtration using column chromatography with ethyl acetate:hexane=1:5 to afford [Compound 81] (17.2 g, yield 92%).

Synthesis Example 7: Synthesis of Compound 83

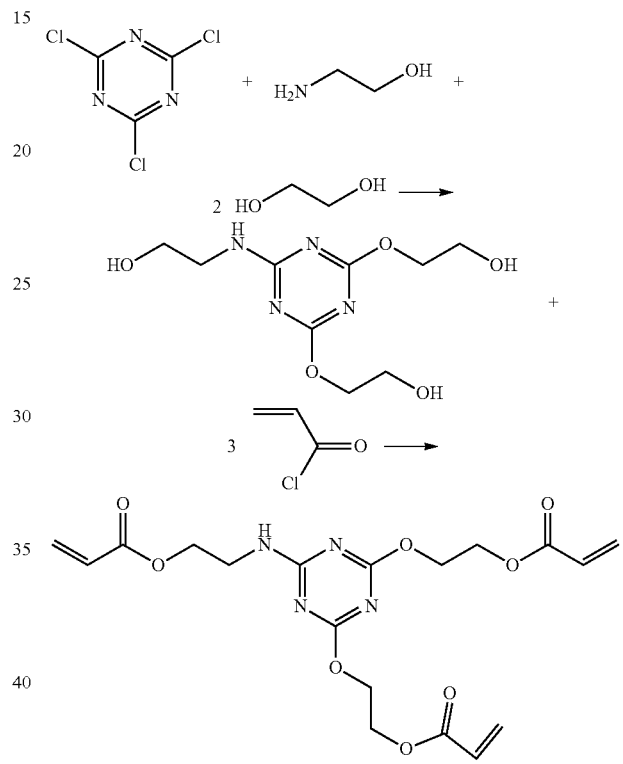

Synthesis Example 7-1: Synthesis of 2,2'-((6-((2-hydroxyethyl)amino)-1,3,5-triazine-2,4-diyl)bis (oxy))diethanol In a 500-mL reactor, 2,4,6-trichloro-1,3,5-triazine (15.0 g, 81.3 mmol) was added to THF (150 ml) under a nitrogen atmosphere. To the reactor that was cooled to 0° C., 2-aminoethanol (5.0 g, 81.3 mmol) and ethane-1,2-diol (10.0 g, 162.6 mmol) were each slowly added over 30 min in the order while stirring, followed by sodium acetate (20.0 g, 244 mmol). The reactor was heated to 80° C. before 15 hours of stirring. After completion of the reaction, extraction was conducted with distilled water and ethyl acetate. The organic layer was washed with distilled water and then dehydrated with MgSO₄. After evaporation of the solvent, column chromatography using EA and hexane at the ratio of 1:3 gave 2,2'-((6-((2-hydroxyethyl)amino)-1,3,5-triazine-2,4-diyl)bis(oxy))diethanol (16 g, yield 76%).

Synthesis Example 7-2: Synthesis of Compound 83

To a 250-ml reactor were sequentially added THF (100 mL), triethylamine (30 ml), and 2,2'-((6-((2-hydroxyethyl)

amino)-1,3,5-triazine-2,4-diyl)bis(oxy))diethanol (10.0 g, 38.4 mmol) which were then cooled to 0° C. under a nitrogen atmosphere. Acryloyl chloride (10.4 g, 115.2 mmol) was slowly added over 30 min to the reactor and stirred at room temperature for 10 hours. After completion of the reaction, extraction was conducted with distilled water and ethyl acetate. The organic layer thus formed was dried over MgSO$_4$. Concentration in a vacuum was followed by filtration using column chromatography with ethyl acetate:hexane=1:5 to afford [Compound 83] (15.2 g, yield 94%).

Synthesis Example 8: Synthesis of Compound 85

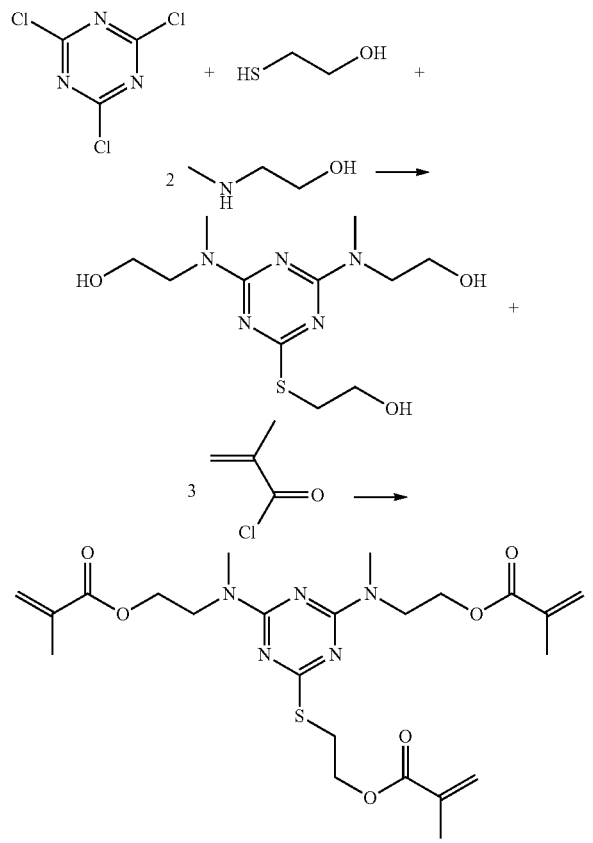

Synthesis Example 8-1: Synthesis of 2,2'-((6-((2-hydroxyethyl)thio)-1,3,5-triazine-2,4-diyl)bis(methylazanediyl))diethanol In a 500-mL reactor, 2,4,6-trichloro-1,3,5-triazine (15.0 g, 81.3 mmol) was added to THF (150 ml) under a nitrogen atmosphere. To the reactor that was cooled to 0° C., 2-mercaptoethanol (6.3 g, 81.3 mmol) and 2-(methylamino)ethanol (12.2 g, 162.6 mmol) were each slowly added over 30 min in the order while stirring, followed by sodium acetate (20.0 g, 244 mmol). The reactor was heated to 80° C. before 15 hours of stirring. After completion of the reaction, extraction was conducted with distilled water and ethyl acetate. The organic layer was washed with distilled water and then dehydrated with MgSO$_4$. After evaporation of the solvent, column chromatography using EA and hexane at the ratio of 1:3 gave 2,2'-((6-((2-hydroxyethyl)thio)-1,3,5-triazine-2,4-diyl)bis(methylazanediyl))diethanol (19.0 g, yield 77%).

Synthesis Example 8-2: Synthesis of Compound 85

To a 250-ml reactor were sequentially added THF (100 mL), triethylamine (20 ml), and 2,2'-((6-((2-hydroxyethyl)thio)-1,3,5-triazine-2,4-diyl)bis(methylazanediyl))diethanol (10.0 g, 32.9 mmol) which were then cooled to 0° C. under a nitrogen atmosphere. Methacryloyl chloride (10.3 g, 98.8 mmol) was slowly added over 30 min to the reactor and stirred at room temperature for 10 hours. After completion of the reaction, extraction was conducted with distilled water and ethyl acetate. The organic layer thus formed was dried over MgSO$_4$. Concentration in a vacuum was followed by filtration using column chromatography with ethyl acetate:hexane=1:5 to afford [Compound 85] (15.0 g, yield 90%).

Synthesis Example 9: Synthesis of Compound 99

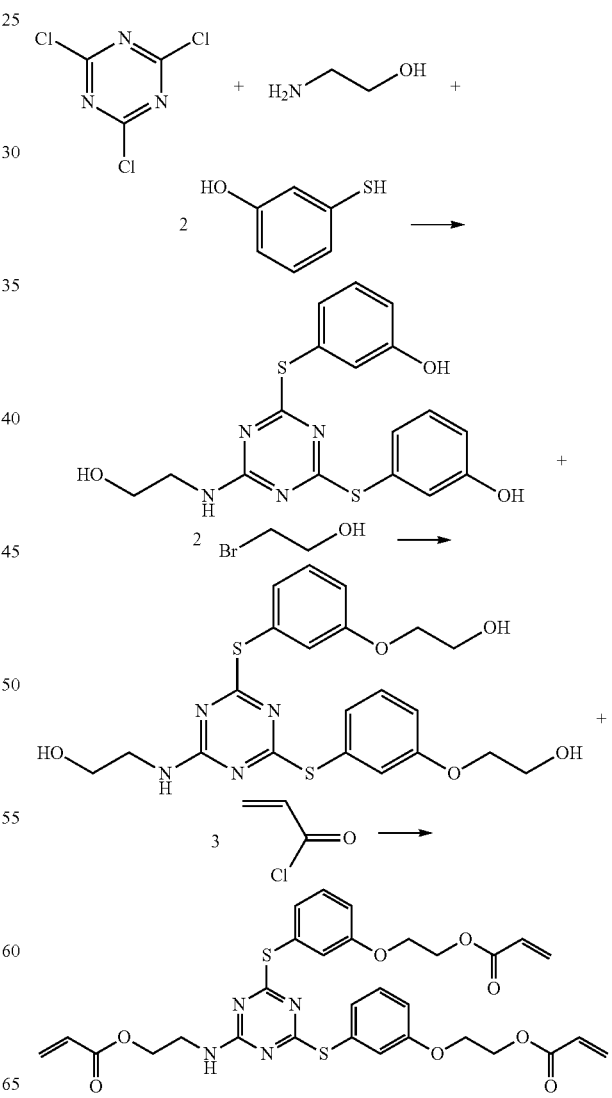

Synthesis Example 9-1: Synthesis of 3,3'-((6-((2-hydroxyethyl)amino)-1,3,5-triazine-2,4-diyl)bis(sulfanediyl))diphenol In a 500-mL reactor, 2,4,6-trichloro-1,3,5-triazine (15.0 g, 81.3 mmol) was added to THF (150 ml) under a nitrogen atmosphere. To the reactor that was cooled to 0° C., 2-aminoethanol (4.9 g, 81.3 mmol) and 3-mercaptophenol (20.5 g, 162.6 mmol) were each slowly added over 30 min in the order while stirring, followed by sodium acetate (20.0 g, 244.0 mmol). The reactor was heated to 80° C. before 15 hours of stirring. After completion of the reaction, extraction was conducted with distilled water and ethyl acetate. The organic layer was washed with distilled water and then dehydrated with MgSO$_4$. After evaporation of the solvent, column chromatography using EA and hexane at the ratio of 1:3 gave 3,3'-((6-((2-hydroxyethyl)amino)-1,3,5-triazine-2,4-diyl)bis(sulfanediyl))diphenol (23.0 g, yield 73%).

Synthesis Example 9-2: Synthesis of 2,2'-((((6-((2-hydroxyethyl)amino)-1,3,5-triazine-2,4-diyl)bis(sulfanediyl))bis(3,1-phenylene))bis(oxy))diethanol In a 250-mL reactor, 3,3'-((6-((2-hydroxyethyl)amino)-1,3,5-triazine-2,4-diyl)bis(sulfanediyl))diphenol (10.0 g, 25.7 mmol) and K$_2$CO$_3$ (7.1 g, 51.4 mmol) were added to DMF (100 ml) under a nitrogen atmosphere. To the reactor was slowly added 2-bromoethanol (6.4 g, 51.4 mmol) over 30 min which was stirred at 80° C. for 10 hours. After completion of the reaction, extraction was conducted with distilled water and ethyl acetate. The organic layer thus formed was washed twice with distilled water. The organic layer was dehydrated with MgSO$_4$ and concentrated in a vacuum to afford 2,2'-((((6-((2-hydroxyethyl)amino)-1,3,5-triazine-2,4-diyl)bis(sulfanediyl))bis(3,1-phenylene))bis(oxy))diethanol as a white solid (11.3 g, yield 92%).

Synthesis Example 9-3: Synthesis of Compound 99

To a 250-ml reactor were sequentially added THF (100 mL), triethylamine (20 ml), and 2,2'-((((6-((2-hydroxyethyl)amino)-1,3,5-triazine-2,4-diyl)bis(sulfanediyl))bis(3,1-phenylene))bis(oxy))diethanol (10.0 g, 20.9 mmol) which were then cooled to 0° C. under a nitrogen atmosphere. Acryloyl chloride (5.7 g, 62.9 mmol) was slowly added over 30 min to the reactor and stirred at room temperature for 10 hours. After completion of the reaction, extraction was conducted with distilled water and ethyl acetate. The organic layer thus formed was dried over MgSO$_4$. Concentration in a vacuum was followed by filtration using column chromatography with ethyl acetate:hexane=1:4 to afford [Compound 99] (12.6 g, yield 94%).

Synthesis Example 10: Synthesis of Compound 109

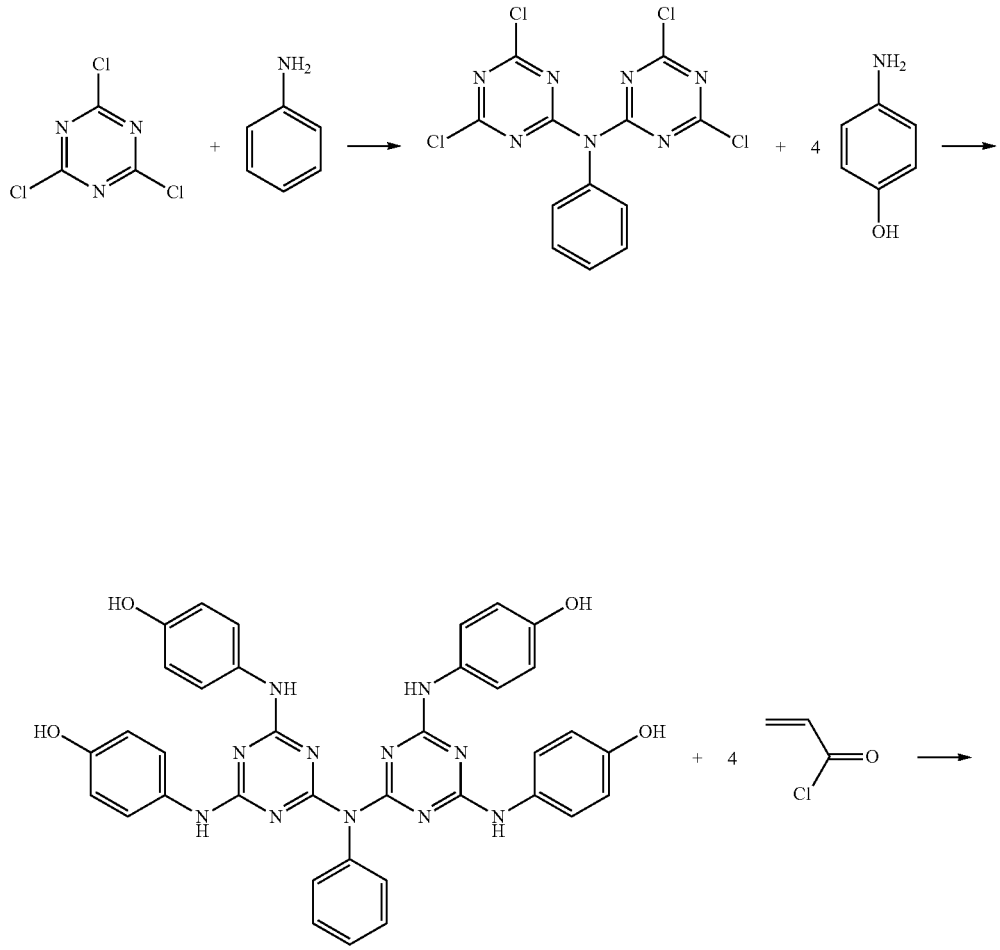

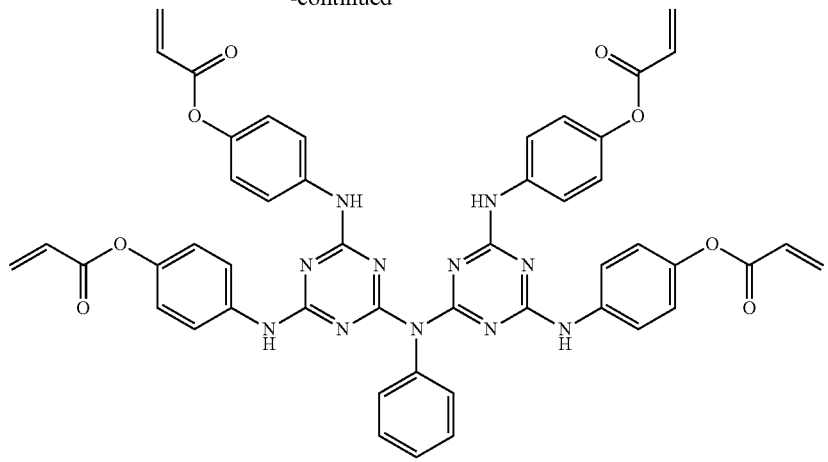

Synthesis Example 10-1: Synthesis of 4,6-dichloro-N-(4,6-dichloro-1,3,5-triazin-2-yl)-N-phenyl-1,3,5-triazin-2-amine In a 500-mL reactor was placed THF (200 ml), followed by adding 2,4,6-trichloro-1,3,5-triazine (20.0 g, 108.5 mmol) under a nitrogen atmosphere. After the reactor was cooled to 0° C., aniline (5.0 g, 54.2 mmol) was slowly added over 30 min while stirring. Sodium acetate (17.8 g, 216.9 mmol) was added to the reactor which was then heated to room temperature at which stirring was continued for 10 hours. After completion of the reaction, distilled water (150 ml) was added and stirred to afford 4,6-dichloro-N-(4,6-dichloro-1,3,5-triazin-2-yl)-N-phenyl-1,3,5-triazin-2-amine as a white solid (17.5 g, yield 83%).

Synthesis Example 10-2: Synthesis of 4,4',4'',4'''-((6,6'-(phenylazanediyl)bis(1,3,5-triazine-6,4,2-triyl))tetrakis(azanediyl))tetraphenol In a 500-mL reactor was placed THF (200 ml), followed by adding 4,6-dichloro-N-(4,6-dichloro-1,3,5-triazin-2-yl)-N-phenyl-1,3,5-triazin-2-amine (17.5 g, 45.0 mmol) under a nitrogen atmosphere. After the reactor was cooled to 0° C., 4-aminophenol (19.7 g, 180.0 mmol) was slowly added over 30 min while stirring. Sodium acetate (14.8 g, 180.0 mmol) was added to the reactor which was then heated to 80° C. at which stirring was continued for 10 hours. After completion of the reaction, distilled water (150 ml) was added and stirred to afford 4,4',4'',4'''-((6,6'-(phenylazanediyl)bis(1,3,5-triazine-6,4,2-triyl))tetrakis(azanediyl))tetraphenol as a white solid (27.8 g, yield 91%).

Synthesis Example 10-3: Synthesis of Compound 109

To a 500-ml reactor were sequentially added THF (200 mL) and 4,4',4'',4'''-((6,6'-(phenylazanediyl)bis(1,3,5-triazine-6,4,2-triyl))tetrakis(azanediyl))tetraphenol (27.8 g, 41.0 mmol) which were then cooled to 0° C. under a nitrogen atmosphere. Acryloyl chloride (14.8 g, 163.8 mmol) was slowly added over 30 min to the reactor and stirred at room temperature for 5 hours. After completion of the reaction, extraction was conducted with distilled water and ethyl acetate. The organic layer thus formed was dried over $MgSO_4$. Concentration in a vacuum was followed by filtration using column chromatography with ethyl acetate:hexane=1:3 to afford [Compound 109] (30.8 g, yield 84%).

Synthesis Example 11: Synthesis of Compound 110

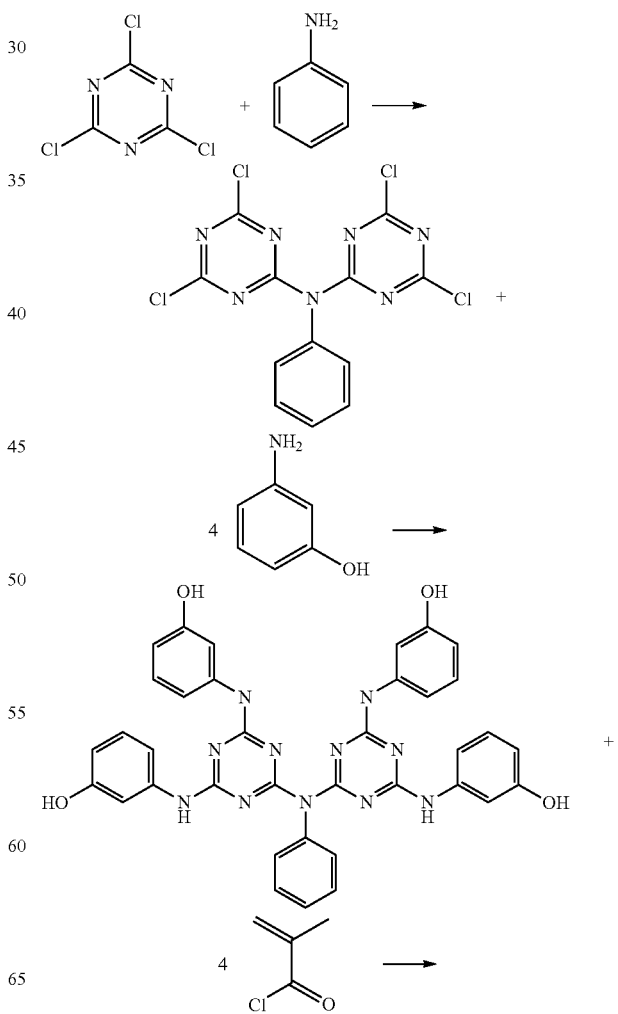

-continued

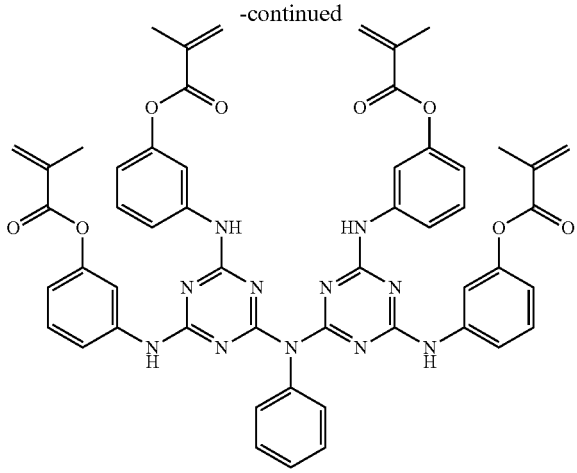

Synthesis Example 11-1: Synthesis of 4,6-dichloro-N-(4,6-dichloro-1,3,5-triazin-2-yl)-N-phenyl-1,3,5-triazin-2-amine In a 500-mL reactor was placed THF (200 ml), followed by adding 2,4,6-trichloro-1,3,5-triazine (20.0 g, 108.5 mmol) under a nitrogen atmosphere. After the reactor was cooled to 0° C., aniline (5.0 g, 54.2 mmol) was slowly added over 30 min while stirring. Sodium acetate (17.8 g, 216.9 mmol) was added to the reactor which was then heated to room temperature at which stirring was continued for 10 hours. After completion of the reaction, distilled water (150 ml) was added and stirred to afford 4,6-dichloro-N-(4,6-dichloro-1,3,5-triazin-2-yl)-N-phenyl-1,3,5-triazin-2-amine as a white solid (17.1 g, yield 81%).

Synthesis Example 11-2: Synthesis of 3,3',3",3'''-((6,6'-(phenylazanediyl)bis(1,3,5-triazine-6,4,2-triyl))tetrakis(azanediyl))tetraphenol In a 500-mL reactor was placed THF (200 ml), followed by adding 4,6-dichloro-N-(4,6-dichloro-1,3,5-triazin-2-yl)-N-phenyl-1,3,5-triazin-2-amine (17.1 g, 43.9 mmol) under a nitrogen atmosphere. After the reactor was cooled to 0° C., 3-aminophenol (19.2 g, 175.7 mmol) was slowly added over 30 min while stirring. Sodium acetate (14.4 g, 175.7 mmol) was added to the reactor which was then heated to 80° C. at which stirring was continued for 10 hours. After completion of the reaction, distilled water (150 ml) was added and stirred to afford 3,3',3",3'''-((6,6'-(phenylazanediyl)bis(1,3,5-triazine-6,4,2-triyl))tetrakis(azanediyl))tetraphenol as a white solid (26.9 g, yield 90%).

Synthesis Example 11-3: Synthesis of Compound 110

To a 500-ml reactor were sequentially added THF (200 mL) and 3,3',3",3'''-((6,6'-(phenylazanediyl)bis(1,3,5-triazine-6,4,2-triyl))tetrakis(azanediyl))tetraphenol (26.9 g, 39.5 mmol) which were then cooled to 0° C. under a nitrogen atmosphere. Methacryloyl chloride (16.5 g, 158.13 mmol) was slowly added over 30 min to the reactor and stirred at room temperature for 5 hours. After completion of the reaction, extraction was conducted with distilled water and ethyl acetate. The organic layer thus formed was dried over MgSO$_4$. Concentration in a vacuum was followed by filtration using column chromatography with ethyl acetate:hexane=1:3 to afford [Compound 110] (30.9 g, yield 82%).

Synthesis Example 12: Synthesis of Compound 122

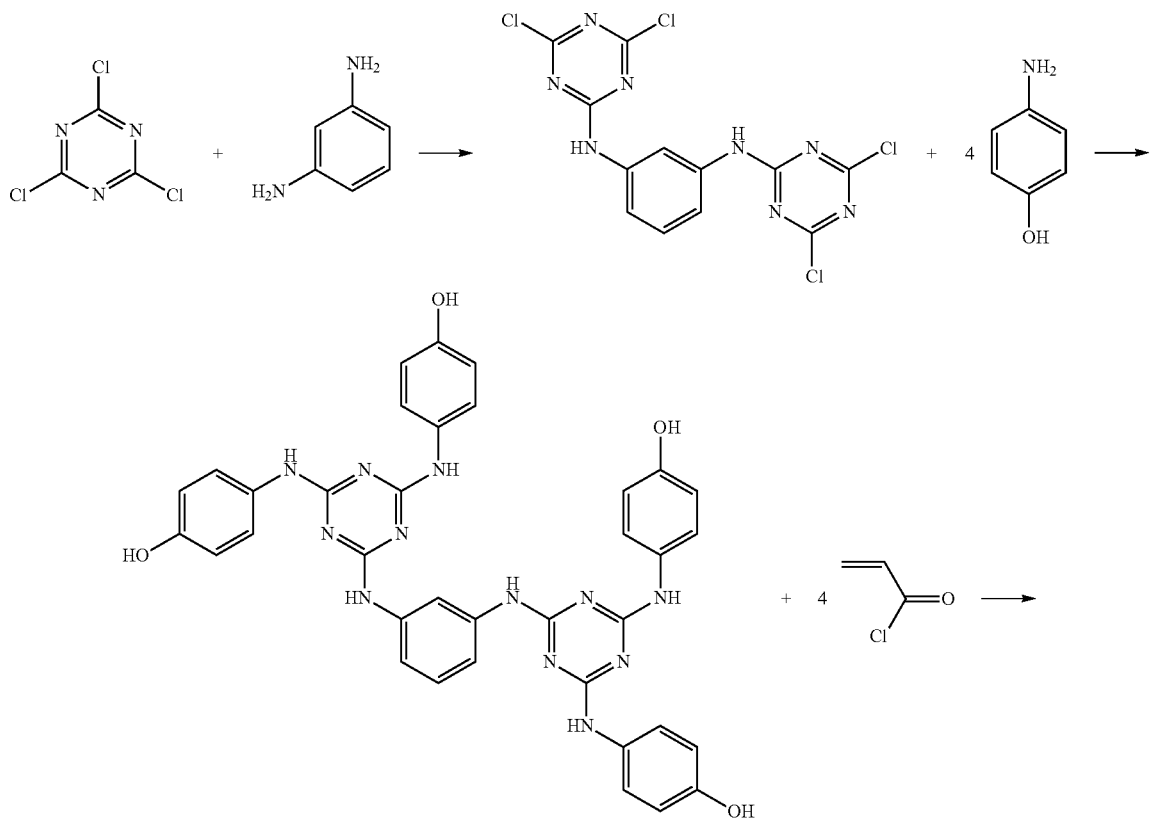

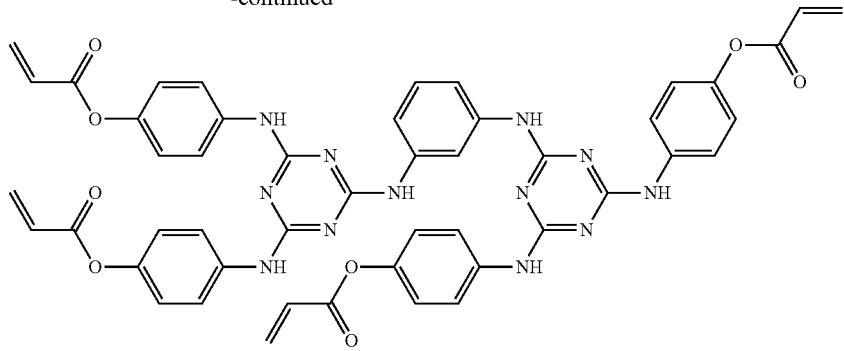

Synthesis Example 12-1: Synthesis of N1,N3-bis (4,6-dichloro-1,3,5-triazin-2-yl)benzene-1,3-diamine In a 500-mL reactor was placed THF (200 ml), followed by adding 2,4,6-trichloro-1,3,5-triazine (20.0 g, 108.5 mmol) under a nitrogen atmosphere. After the reactor was cooled to 0° C., benzene-1,3-diamine (5.9 g, 54.2 mmol) was slowly added over 30 min while stirring. Sodium acetate (17.8 g, 216.9 mmol) was added to the reactor which was then heated to room temperature at which stirring was continued for 10 hours. After completion of the reaction, distilled water (150 ml) was added and stirred to afford N1,N3-bis(4,6-dichloro-1,3,5-triazin-2-yl)benzene-1,3-diamine as a white solid (15.5 g, yield 71%).

Synthesis Example 12-2: Synthesis of 4,4',4'',4'''-((6,6'-(1,3-phenylenebis(azanediyl))bis(1,3,5-triazine-6,4,2-triyl))tetrakis(azanediyl))tetraphenol In a 500-mL reactor was placed THF (200 ml), followed by adding N1,N3-bis(4,6-dichloro-1,3,5-triazin-2-yl)benzene-1,3-diamine (15.5 g, 38.5 mmol) under a nitrogen atmosphere. After the reactor was cooled to 0° C., benzene-1,3-diamine (5.9 g, 54.2 mmol) was slowly added over 30 min while stirring. Sodium acetate (17.8 g, 216.9 mmol) was added to the reactor which was then heated to 80° C. at which stirring was continued for 10 hours. After completion of the reaction, distilled water (150 ml) was added and stirred to afford 4,4',4'',4'''-((6,6'-(1,3-phenylenebis(azanediyl))bis(1,3,5-triazine-6,4,2-triyl))tetrakis(azanediyl))tetraphenol (23.8 g, yield 89%).

Synthesis Example 12-3: Synthesis of Compound 122

To a 500-ml reactor were sequentially added THF (200 mL) and 4,4',4'',4'''-((6,6'-(1,3-phenylenebis(azanediyl))bis(1,3,5-triazine-6,4,2-triyl))tetrakis(azanediyl))tetraphenol (23.8 g, 34.3 mmol) which were then cooled to 0° C. under a nitrogen atmosphere. Acryloyl chloride (12.4 g, 137.0 mmol) was slowly added over 30 min to the reactor and stirred at room temperature for 5 hours. After completion of the reaction, extraction was conducted with distilled water and ethyl acetate. The organic layer thus formed was dried over MgSO$_4$. Concentration in a vacuum was followed by filtration using column chromatography with ethyl acetate: hexane=1:3 to afford [Compound 122] (26.5 g, yield 85%).

Synthesis Example 13: Synthesis of Compound 123

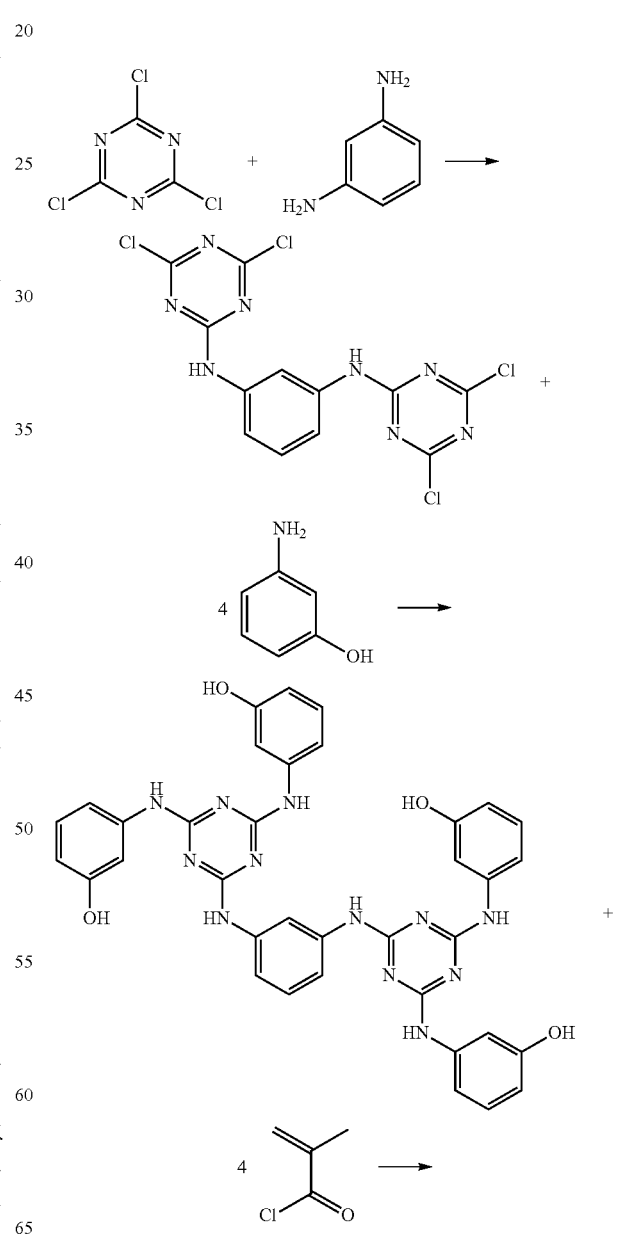

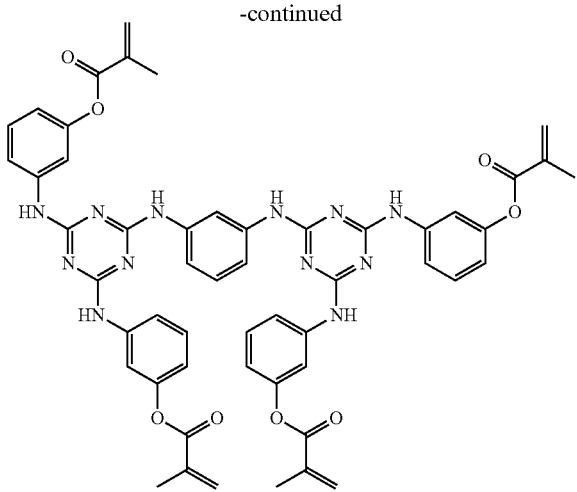

Synthesis Example 13-1: Synthesis of N1,N3-bis(4, 6-dichloro-1,3,5-triazin-2-yl)benzene-1,3-diamine In a 500-mL reactor was placed THF (200 ml), followed by adding 2,4,6-trichloro-1,3,5-triazine (20.0 g, 108.5 mmol) under a nitrogen atmosphere. After the reactor was cooled to 0° C., benzene-1,3-diamine (5.9 g, 54.2 mmol) was slowly added over 30 min while stirring. Sodium acetate (17.8 g, 216.9 mmol) was added to the reactor which was then heated to room temperature at which stirring was continued for 10 hours. After completion of the reaction, distilled water (150 ml) was added and stirred to afford N1,N3-bis(4,6-dichloro-1,3,5-triazin-2-yl)benzene-1,3-diamine as a white solid (16.4 g, yield 75%).

Synthesis Example 13-2: Synthesis of 3,3',3'',3'''-((6,6'-(1,3-phenylenebis(azanediyl))bis(1,3,5-triazine-6,4,2-triyl))tetrakis(azanediyl))tetraphenol In a 500-mL reactor was placed THF (200 ml), followed by adding N1,N3-bis(4,6-dichloro-1,3,5-triazin-2-yl)benzene-1,3-diamine (16.4 g, 40.7 mmol) under a nitrogen atmosphere. After the reactor was cooled to 0° C., 3-aminophenol (17.8 g, 162.7 mmol) was slowly added over 30 min while stirring. Sodium acetate (13.3 g, 162.7 mmol) was added to the reactor which was then heated to 80° C. at which stirring was continued for 10 hours. After completion of the reaction, distilled water (150 ml) was added and stirred to afford 3,3',3'',3'''-((6,6'-(1,3-phenylenebis(azanediyl))bis(1,3,5-triazine-6,4,2-triyl))tetrakis(azanediyl))tetraphenol (25.4 g, yield 90%).

Synthesis Example 13-3: Synthesis of Compound 123

To a 500-ml reactor were sequentially added THF (200 mL) and 3,3',3'',3'''-((6,6'-(1,3-phenylenebis(azanediyl))bis(1,3,5-triazine-6,4,2-triyl))tetrakis(azanediyl))tetraphenol (25.4 g, 36.6 mmol) which were then cooled to 0° C. under a nitrogen atmosphere. Methacryloyl chloride (15.3 g, 146.4 mmol) was slowly added over 30 min to the reactor and stirred at room temperature for 5 hours. After completion of the reaction, extraction was conducted with distilled water and ethyl acetate. The organic layer thus formed was dried over MgSO$_4$. Concentration in a vacuum was followed by filtration using column chromatography with ethyl acetate: hexane=1:3 to afford [Compound 123] (30.1 g, yield 85%).

Examples 1 to 16

As indicated in Table 2, below, (A) vinylphenyloxy monomers, (B) photopolymerizable monomers, (C) photoinitiators, (D) a releasing agent, and (E) a UV stabilizer were stirred for hours in a brown reactor to prepare photosensitive compositions.

In Examples 1 to 16 and Comparative Examples 1 and 2, the following components were used:

(A) Acryl Group-Bearing Monomers
Compound 2 (M2): ((6-((3-hydroxyphenyl)amino)-1,3,5-triazine-2,4-diyl)bis(azanediyl))bis(3,1-phenylene)diacrylate
Compound 4 (M4): ((1,3,5-triazine-2,4,6-triyl)tris(azanediyl))tris(benzene-4,1-diyl)triacrylate
Compound 12 (M12): 35 4-((4,6-bis((4-hydroxyphenyl)(methyl)amino)-1,3,5-triazine-2-yl) (methyl)amino) phenylacrylate
Compound 25 (M25): ((((1,3,5-triazine-2,4,6-triyl)tris(azanediyl))tris(benzene-3,1-diyl))tris(oxy))tris(ethane-2,1-diyl)triacrylate
Compound 40 (M40): ((6-((4-methoxyphenyl)amino)-1,3,5-triazine-2,4-diyl)bis(azanediyl))bis(3,1-phenylene)bis(2-methylacrylate)
Compound 81 (M81): ((6-((2-(acryloyloxy)ethyl)amino)-1,3,5-triazine-2,4-diyl)bis(sulfanediyl))bis(ethane-2,1-diyl) diacrylate
Compound 83 (M83): ((6-((2-(acryloyloxy)ethyl)amino)-1,3,5-triazine-2,4-diyl)bis(oxy))bis(ethane-2,1-diyl)diacrylate
Compound 85 (M85): ((6-((2-(methacryloxy)ethyl)thio)-1,3,5-triazine-2,4-diyl)bis(methylazanediyl))bis(ethane-2,1-diyl)bis(2-methylacrylate)
Compound 99 (M99): (((((6-((2-(acryloxy)ethyl)amino)-1,3,5-triazine-2,4-diyl)bis(sulfanediyl))bis (3,1-phenylene))bis(oxy))bis(ethane-2,1-diyl) diacrylate
Compound 109 (M109): ((6,6'-(phenylazanediyl)bis(1,3,5-triazine-6,4,2-triyl))tetrakis(azanediyl))tetrakis(benzene-4,1-diyl)tetraacrylate
Compound 110 (M110): ((6,6'-(phenylazanediyl)bis(1,3,5-triazine-6,4,2-triyl))tetrakis(azanediyl))tetrakis(benzene-3,1-diyl)tetrakis(2-methylacrylate)
Compound 122 (M122): ((6,6'-(1,3-phenylenebis(azanediyl))bis(1,3,5-triazine-6,4,2-triyl))tetrakis(azanediyl))tetrakis(benzene-4,1-diyl)tetraacrylate
Compound 123 (M123): ((6,6'-(1,3-phenylenebis(azanediyl))bis(1,3,5-triazine-6,4,2-triyl))tetrakis(azanediyl))tetrakis(benzene-3,1-diyl)tetrakis(2-methylacrylate)

(B) Photopolymerizable Compounds:
B1: 2-([1,1'-bphenyl]-2-yloxy)ethylacrylate
B2: dipentaerythritolpentaacrylate (C) Photopolymerization initiator:
C$_1$: diphenyl-2,4,6-trimethylbenzoylphosphine oxide
C$_2$: (1-hydroxycyclohexyl) (phenyl)methanone (D) Releasing agent
D1: silicone-base releasing agent (E) UV stabilizer
E1: amine-based UV stabilizer Comparative Examples 1 to 2

The same procedure as in Examples 1 and 2 was carried out with the exception that the following R1 (((9H-fluorene- 9,9-diyl)bis(4,1-phenylene))bis(oxy))bis(ethan-2,1-diyl)diacrylate, instead of Compound 2 or Compound 4, was used as a high refractive index monomer.

R1)

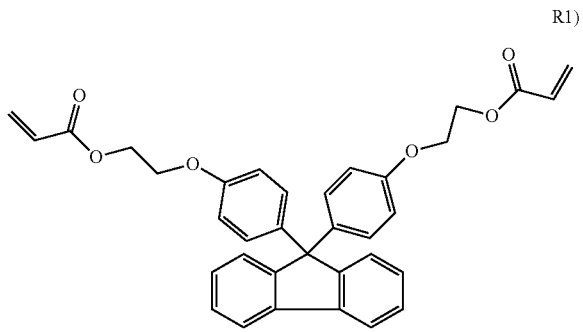 [SMILES: C=CC(=O)OCCOc1ccc(C2(c3ccc(OCCOC(=O)C=C)cc3)c3ccccc3-c3ccccc32)cc1]

TABLE 2

| Ex. No. | High Refractive Index Acryl Monomer | Photo-polymerizable compound | Photo-initiator | Releasing Agent | UV Stabilizer |
|---|---|---|---|---|---|
| | | Composition (wt. part) | | | |
| 1 | M2(30) | B1(40), B2(27) | C1(1), C2(1) | D1(0.5), | E1(0.5) |
| 2 | M2(40) | B1(40), B2(17) | C1(1), C2(1) | D1(0.5) | E1(0.5) |
| 3 | M4(30) | B1(40), B2(27) | C1(1), C2(1) | D1(0.5) | E1(0.5) |
| 4 | M4(40) | B1(40), B2(17) | C1(1), C2(1) | D1(0.5) | E1(0.5) |
| 5 | M12(40) | B1(40), B2(17) | C1(1), C2(1) | D1(0.5), | E1(0.5) |
| 6 | M25(40) | B1(40), B2(17) | C1(1), C2(1) | D1(0.5) | E1(0.5) |
| 7 | M40(40) | B1(40), B2(17) | C1(1), C2(1) | D1(0.5), | E1(0.5) |
| 8 | M81(40), | B1(40), B2(17) | C1(1), C2(1) | D1(0.5) | E1(0.5) |
| 9 | M83(40), | B1(40), B2(17) | C1(1), C2(1) | D1(0.5) | E1(0.5) |
| 10 | M85(40), | B1(40), B2(17) | C1(1), C2(1) | D1(0.5) | E1(0.5) |
| 11 | M99(40), | B1(40), B2(17) | C1(1), C2(1) | D1(0.5) | E1(0.5) |
| 12 | M2(20), M99(20) | B1(40), B2(17) | C1(1), C2(1) | D1(0.5) | E1(0.5) |
| 13 | M109(40), | B1(40), B2(17) | C1(1), C2(1) | D1(0.5) | E1(0.5) |
| 14 | M110(40), | B1(40), B2(17) | C1(1), C2(1) | D1(0.5) | E1(0.5) |
| 15 | M122(40), | B1(40), B2(17) | C1(1), C2(1) | D1(0.5) | E1(0.5) |
| 16 | M123(40), | B1(40), B2(17) | C1(1), C2(1) | D1(0.5) | E1(0.5) |
| C. 1 | R1(30) | B1(40), B2(27) | C1(1), C2(1) | D1(0.5), | E1(0.5) |
| C. 2 | R1(40) | B1(40), B2(17) | C1(1), C2(1) | D1(0.5) | E1(0.5) |

Test Example 1: Refractive Index Evaluation

The high refractive index monomers synthesized were each dissolved in 2-([1,1'-biphenyl]-2-yloxy)ethylacrylate at an equivalent weight ratio and then measured for refractive index at 25° C. using an Abbe refractometer.

Test Example 2: Viscosity Evaluation

The high refractive index monomers were each dissolved in 2-([1,1'-biphenyl]-2-yloxy)ethylacrylate at an equivalent weight ratio and then measured for viscosity 25° C. using a Brookfield viscometer.

Test Example 3: Transmittance Evaluation

The photosensitive compositions obtained in the Examples were exposed to UV at a dose of 500 mJ/cm$^2$ on an optical PET substrate to prepare crosslinked prism sheet specimens. The crosslinked prism sheets were measured for UV transmittance at 400 using UV-vis.

Test Example 4: Yellowing Index (ΔYI) Evaluation

The crosslinked prism sheets were each exposed to a UVA lamp at a dose of 1 J for 8 hours under the condition of 95% RH in the QUV Accelerated Weathering Tester. The exposure was carried out for a total of 120 hours before measuring ΔYI, which accounts for a change relative to an initial yellow index value.

Evaluation results are summarized in Table 3, below.

TABLE 3

| Ex. No. | Refractive Index (%) | Viscosity (cPs) | Transmittance (%) | Yellowing Index (ΔYI) |
|---|---|---|---|---|
| 1 | 1.604 | 1500 | 97 | 11 |
| 2 | 1.608 | 1800 | 96 | 13 |
| 3 | 1.604 | 1600 | 97 | 12 |
| 4 | 1.609 | 1900 | 96 | 13 |
| 5 | 1.611 | 1800 | 96 | 12 |
| 6 | 1.608 | 1800 | 97 | 11 |
| 7 | 1.609 | 1900 | 96 | 12 |
| 8 | 1.603 | 1800 | 95 | 13 |
| 9 | 1.602 | 1700 | 96 | 14 |
| 10 | 1.602 | 1900 | 96 | 14 |
| 11 | 1.607 | 1700 | 98 | 12 |
| 12 | 1.610 | 1700 | 97 | 12 |
| 13 | 1.617 | 1800 | 97 | 10 |
| 14 | 1.615 | 1800 | 97 | 11 |
| 15 | 1.619 | 1900 | 98 | 11 |
| 16 | 1.618 | 1900 | 98 | 10 |
| C. 1 | 1.588 | 1800 | 93 | 15 |
| C. 2 | 1.593 | 2000 | 93 | 17 |

As shown in Table 3, the photosensitive compositions of Examples 1 to 16 exhibited remarkably high refractive indices and similar viscosities, compared to those of Comparative Examples 1 to 2. When tested with prism sheets, the compositions of Examples 1 to 6 were measured to be superior to those of Comparative Examples 1 and 2 in terms of light transmittance and yellowing index after reliability test.

INDUSTRIAL APPLICABILITY

The triazine derivative compound according to the present disclosure is used in a photosensitive composition and allows the photosensitive composition to exhibit a high refractive index following a photocrosslinking process and to overcome the problem with conventional techniques that optical sheets undergo discoloration due to yellowing. Therefore, the present disclosure provides a photosensitive composition having high transmittance and excellent anti-yellowing properties and can find applications in fabricating prism sheets, microlenses, coating materials for LCDs, dual brightness enhancement films (DBEF), coating materials for

The invention claimed is:

1. A compound, represented by any one of the following [Chemical Formula A] to [Chemical Formula C]:

[Chemical Formula A]

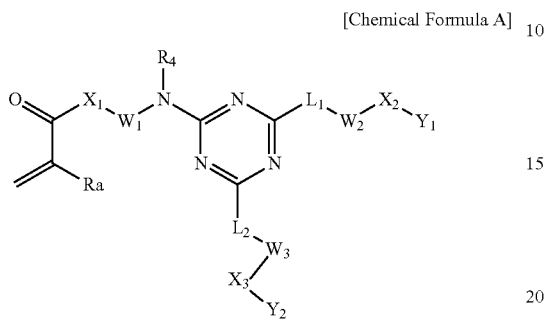

wherein,

Ra is a substituent selected from a hydrogen atom, a deuterium atom, a substituted or unsubstituted alkyl of $C_1$-$C_6$, $L_1$ is any one selected from a single bond, O, S, and —N(—$R_5$)—, $L_2$ is any one selected from a single bond, O, S, and —N(—$R_6$)—, $X_2$ and $X_3$, which are the same or different, are each independently any one selected from a single bond, O, S, —N(—$R_7$)—, and —O(($CH_2$)$_m$O)$_n$— wherein m and n, which are the same or different, are each independently an integer of 1 to 4, $X_1$ is any one selected from a single bond, O, S, and —O(($CH_2$)$_m$O)$_n$— wherein m and n, which are the same or different, are each independently an integer of 1 to 4, wherein when at least two of $X_1$ to $X_3$ are each —N(—$R_7$)— or —O(($CH_2$)$_m$O)$_n$—, the individual —N(—$R_7$)— moieties or the individual —O(($CH_2$)$_m$O)$_n$— are same or different, $R_4$ to $R_7$, which are the same or different, are each independently any one selected from a hydrogen atom, a deuterium atom, a substituted or unsubstituted alkyl of $C_1$-$C_{30}$, a substituted or unsubstituted aryl of $C_6$-$C_{50}$, a substituted or unsubstituted cycloalkyl of $C_3$-$C_{30}$, and a substituted or unsubstituted arylalkyl of $C_7$-$C_{24}$, $W_1$ is any one selected from a substituted or unsubstituted arylene of $C_6$-$C_{30}$, $W_2$ and $W_3$, which are the same or different, are each independently any one selected from a single bond, a substituted or unsubstituted alkylene of $C_1$-$C_{30}$, a substituted or unsubstituted arylene of $C_6$-$C_{30}$, a substituted or unsubstituted cycloalkylene of $C_3$-$C_{30}$, and a substituted or unsubstituted heteroarylene of $C_2$-$C_{50}$, $Y_1$ and $Y_2$, which are the same or different, are each independently any one selected from a hydrogen atom, a deuterium atom a substituted or unsubstituted alkyl of $C_1$-$C_{30}$, a substituted or unsubstituted aryl of $C_6$-$C_{30}$, a substituted or unsubstituted alkenyl of $C_2$-$C_{30}$, a substituted or unsubstituted alkynyl of $C_2$-$C_{20}$, a substituted or unsubstituted cycloalkyl of $C_3$-$C_{30}$, a substituted or unsubstituted cycloalkenyl of $C_5$-$C_{30}$, a substituted or unsubstituted heteroaryl of heteroaryl of $C_2$-$C_{50}$, a substituted or unsubstituted heterocycloalkyl of heterocycloalkyl of $C_2$-$C_{30}$, a substituted or unsubstituted alkylsilyl of $C_1$-$C_{30}$, a substituted or unsubstituted arylsilyl of $C_6$-$C_{30}$, and a substituent represented by the following Structural Formula 1 or 2:

[Structural Formula 1]

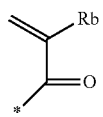

[Structural Formula 2]

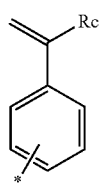

wherein,

Rb and Rc, which are the same or different, are each independently any one selected from a hydrogen atom, a deuterium atom, and a substituted or unsubstituted alkyl of $C_1$-$C_6$, and -"*" means a bonding site at which the substituent represented by Structural Formula 1 or Structural Formula 2 is bonded to $X_2$ or $X_3$ in Chemical Formula A; and

[Chemical Formula B]

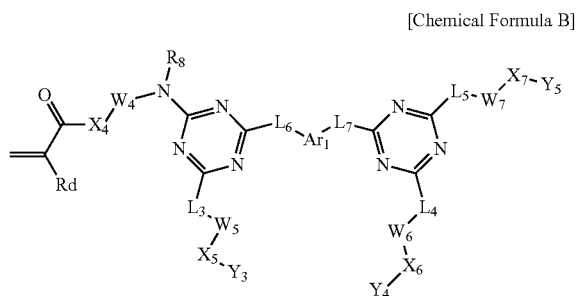

[Chemical Formula C]

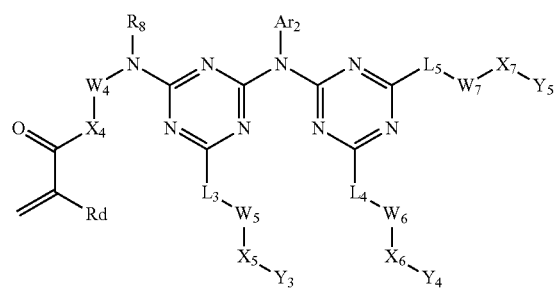

wherein, $Ar_1$ is any one selected from a substituted or unsubstituted arylene of $C_6$-$C_{30}$, a substituted or unsubstituted heteroarylene of $C_2$-$C_{30}$, a substituted or unsubstituted alkylene of $C_1$-$C_{30}$, a substituted or unsubstituted alkenylene of $C_2$-$C_{30}$, a substituted or unsubstituted cycloalkylene of $C_3$-$C_{30}$, and a substituted or unsubstituted cycloalkenylene of $C_5$-$C_{30}$, $L_6$ is any one selected from a single bond, O, S, and —N(—$R_{11}$)—, and $L_7$ is any one selected from a single bond, O, S, and —N(—$R_{12}$)—; and

81

Ar₂ is any one selected from a hydrogen atom, a deuterium atom, a substituted or unsubstituted aryl of $C_6$-$C_{30}$, a substituted or unsubstituted heteroaryl of heteroaryl of $C_2$-$C_{30}$, a substituted or unsubstituted alkyl of $C_1$-$C_{30}$, a substituted or unsubstituted cycloalkyl of $C_3$-$C_{30}$, a substituted or unsubstituted alkenyl of $C_2$-$C_{30}$, and a substituted or unsubstituted cycloalkenyl of $C_5$-$C_{30}$, Rd is a substituent selected from a hydrogen atom, a deuterium atom, and a substituted or unsubstituted alkyl of $C_1$-$C_6$, $L_3$ to $L_5$, which are the same or different, are each independently any one selected from a single bond, O, S, and —N(—$R_9$)—, wherein when at least two of $L_3$ to $L_5$ are each —N(—$R_9$)—, the individual —N(—$R_9$) moieties are same or different, $X_4$ to $X_7$, which are the same or different, are each independently any one selected from a single bond, O, S, —N(—$R_{10}$)—, and —O((CH₂)$_m$O)$_n$— wherein m and n, which are the same or different, are each independently an integer of 1 to 4, wherein when at least two of $X_4$ to $X_7$ are each —N(—$R_{10}$)— or —O((CH₂)$_m$O)$_n$—, the individual —N(—$R_{10}$)— moieties or the individual —O((CH₂)$_m$O)$_n$— moieties are same or different, $R_8$ to $R_{12}$, which are the same or different, are each independently any one selected from a hydrogen atom, a deuterium atom, a substituted or unsubstituted alkyl of $C_1$-$C_{30}$, a substituted or unsubstituted aryl of $C_6$-$C_{30}$, a substituted or unsubstituted cycloalkyl of $C_3$-$C_{30}$, and a substituted or unsubstituted arylalkyl of $C_7$-$C_{24}$, $W_4$ is any one selected from a single bond, a substituted or unsubstituted arylene of $C_6$-$C_{30}$, and a substituted or unsubstituted alkylene of $C_1$-$C_{12}$, $W_5$ to $W_7$, which are the same or different, are each independently any one selected from a single bond, a substituted or unsubstituted alkylene of $C_1$-$C_{30}$, a substituted or unsubstituted arylene of $C_6$-$C_{30}$, a substituted or unsubstituted alkenylene of $C_2$-$C_{30}$, a substituted or unsubstituted cycloalkylene of $C_3$-$C_{30}$, a substituted or unsubstituted cycloalkenylene of $C_5$-$C_{30}$, a substituted or unsubstituted heteroarylene of $C_2$-$C_{50}$, and a substituted or unsubstituted heterocycloalkylene of $C_2$-$C_{30}$, $Y_3$ to $Y_5$, which are the same or different, are each independently any one selected from a hydrogen atom, a deuterium atom a substituted or unsubstituted alkyl of $C_1$-$C_{30}$, a substituted or unsubstituted aryl of $C_6$-$C_{30}$, a substituted or unsubstituted alkenyl of $C_2$-$C_{30}$, a substituted or unsubstituted alkynyl of $C_2$-$C_{20}$, a substituted or unsubstituted cycloalkyl of $C_3$-$C_{30}$, a substituted or unsubstituted cycloalkenyl of $C_5$-$C_{30}$, a substituted or unsubstituted heteroaryl of $C_2$-$C_{50}$, a substituted or unsubstituted heterocycloalkyl of $C_2$-$C_{30}$, a substituted or unsubstituted alkylsilyl of $C_1$-$C_{30}$, a substituted or unsubstituted arylsilyl of $C_6$-$C_{30}$, and a substituent represented by the [Structural Formula 1] or [Structural Formula 2]:

[Structural Formula 1]

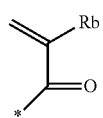

82

-continued

[Structural Formula 2]

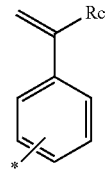

wherein,

Rb and Rc, which are the same or different, are each independently any one selected from a hydrogen atom, a deuterium atom, and a substituted or unsubstituted alkyl of $C_1$-$C_6$, and "-*" means a bonding site at which the substituent represented by Structural Formula 1 or Structural Formula 2 is bonded to $X_5$ to $X_7$ in [Chemical Formula B] or [Chemical Formula C], wherein the term "substituted" in the expression "substituted or unsubstituted" used for [Chemical Formula A] to [Chemical Formula C] means having at least one substituent selected from the group consisting of a deuterium atom, a cyano, a halogen, a hydroxy, a nitro, an alkyl of $C_1$-$C_{24}$, an halogenated alkyl of $C_1$-$C_{24}$, an alkenyl of $C_2$-$C_{24}$, an aryl of $C_6$-$C_{24}$, an arylalkyl of $C_7$-$C_{24}$, an alkoxy of $C_1$-$C_{24}$, an alkylsilyl of $C_1$-$C_{24}$, and an arylsilyl of $C_6$-$C_{24}$.

2. The compound of claim 1, wherein the compound is represented by [Chemical Formula A] and the substituents $R_4$ to $R_6$ in [Chemical Formula A] are same or different and are each independently any one selected from a hydrogen atom, a deuterium atom, a substituted or unsubstituted alkyl of $C_1$-$C_{20}$, and a substituted or unsubstituted aryl of $C_6$-$C_{20}$, and Ra, Rb, and Rc in [Chemical Formula A] are same or different and are each independently any one selected from a hydrogen atom, a deuterium atom, and a methyl.

3. The compound of claim 1, wherein the compound is represented by [Chemical Formula A] and at least one of $Y_1$ and $Y_2$ in [Chemical Formula A] has the structure represented by Structural Formula 1 or Structural Formula 2.

4. The compound of claim 1, wherein the compound is represented by [Chemical Formula A] and $L_1$ is —N(—$R_5$)— or S and $L_2$ is —N(—$R_6$)— or S in [Chemical Formula A].

5. The compound of claim 1, wherein the compound is represented by [Chemical Formula A] and $L_1$ and $L_2$ in [Chemical Formula A] are —N(—$R_5$)— and —N(—$R_6$)—, respectively, $R_5$ and $R_6$, which are same or different, being each independently any one selected from a hydrogen atom, a deuterium atom, an alkyl of $C_1$-$C_{10}$, and an aryl of $C_6$-$C_{20}$.

6. The compound of claim 1, wherein the compound is represented by [Chemical Formula A] and at least two of $W_1$ to $W_3$ in [Chemical Formula A] are a substituted or unsubstituted arylene of $C_6$-$C_{30}$.

7. The compound of claim 1, wherein the compound is represented by [Chemical Formula A] and $W_1$ is a substituted or unsubstituted phenylene and at least one of $W_2$ and $W_3$, which are same or different, is a substituted or unsubstituted arylene of $C_6$-$C_{30}$ in [Chemical Formula A].

8. The compound of claim 1, wherein the compound is represented by [Chemical Formula A] and at least two of $W_1$ to $W_3$, which are the same or different, are a substituted or unsubstituted phenylene in [Chemical Formula A].

9. The compound of claim 1, wherein the compound is represented by [Chemical Formula B] or [Chemical Formula C] and $R_8$ to $R_{12}$, which are same or different, are each independently any one selected from a hydrogen atom, a deuterium atom, a substituted or unsubstituted alkyl of $C_1$-$C_{20}$, and a substituted or unsubstituted aryl of $C_6$-$C_{20}$ and Rb, Rc, and Rd, which are same or different, are each independently any one selected from a hydrogen atom, a deuterium atom, and a methyl.

10. The compound of claim 1, wherein the compound is represented by [Chemical Formula B] or [Chemical Formula C] and at least one of $Y_3$ to $Y_5$ has the structure represented by [Structural Formula 1] or [Structural Formula 2].

11. The compound of claim 1, wherein the compound is represented by [Chemical Formula B] and $L_3$ to $L_7$ are same or different and are each independently a single bond, —N(—$R_9$)—, or S.

12. The compound of claim 1, wherein the compound is represented by [Chemical Formula C] and $L_3$ to $L_5$ are same or different and are each independently a single bond, —N(—$R_9$)—, or S.

13. The compound of claim 1, wherein the compound is represented by [Chemical Formula B] or [Chemical Formula C] and $R_9$, $R_{11}$, and $R_{12}$ are same or different and are each independently any one selected from a hydrogen atom, a deuterium atom, an alkyl of $C_1$-$C_{10}$, and an aryl of $C_6$-$C_{20}$.

14. The compound of claim 1, wherein the compound is represented by [Chemical Formula B] or [Chemical Formula C] and at least two of $W_4$ to $W_7$ are a substituted or unsubstituted arylene of $C_6$-$C_{30}$.

15. The compound of claim 14, wherein the compound is represented by [Chemical Formula B] or [Chemical Formula C] and at least two of $W_4$ to $W_7$ are a substituted or unsubstituted phenylene.

16. The compound of claim 1, wherein the compound is represented by [Chemical Formula B] or [Chemical Formula C] and at least three of $W_4$ to $W_7$ are a substituted or unsubstituted arylene of $C_6$-$C_{30}$.

17. The compound of claim 16, wherein the compound is represented by [Chemical Formula B] or [Chemical Formula C] and at least three of $W_4$ to $W_7$ are a substituted or unsubstituted phenylene.

18. The compound of claim 1, wherein the compound represented by any one of [Chemical Formula A] to [Chemical Formula C] is selected from the compounds represented by the following Compounds 1 to Compound 72, Compound 89 to Compound 98, and Compound 103 to Compound 134:

[Compound 1]

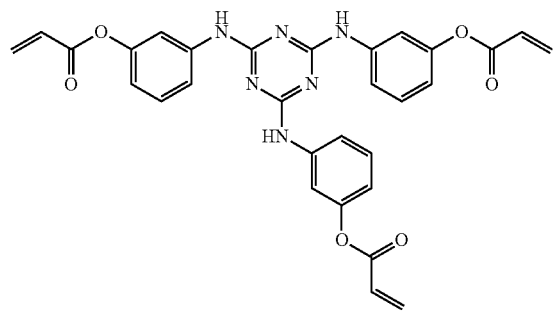

[Compound 2]

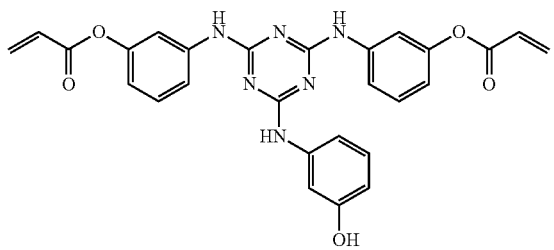

[Compound 3]

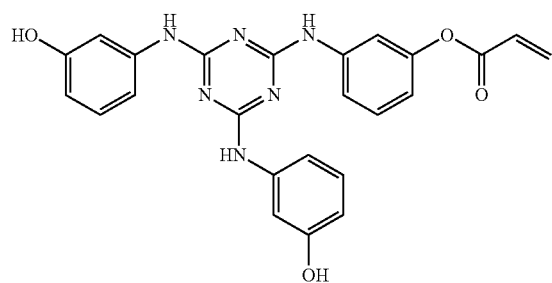

[Compound 4]

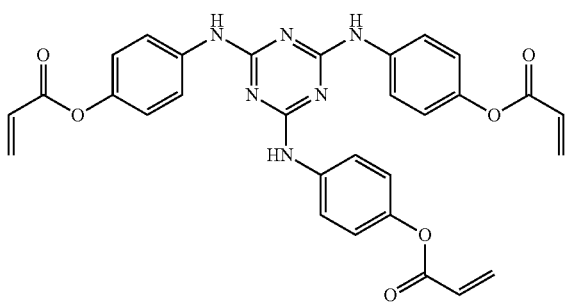

[Compound 5]

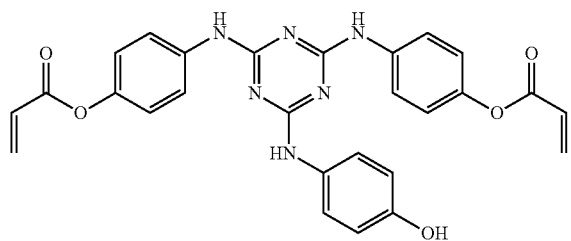

[Compound 6]

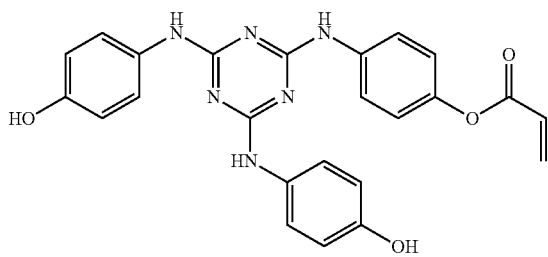

-continued
[Compound 7]
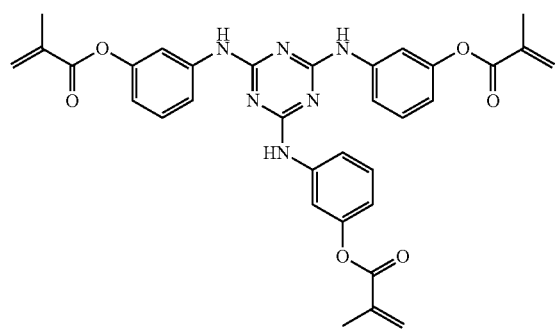
[Compound 8]
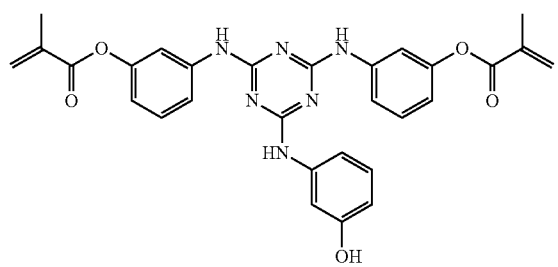
[Compound 9]
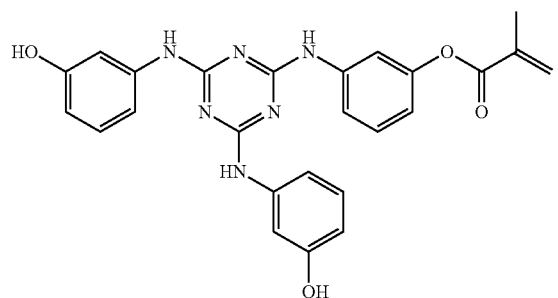
[Compound 10]
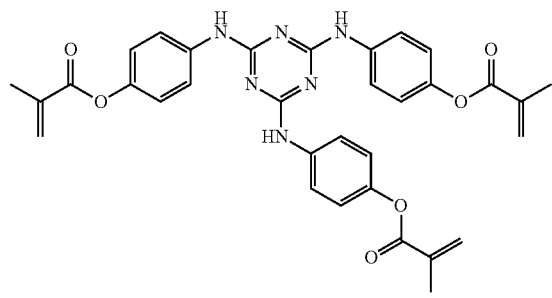
[Compound 11]
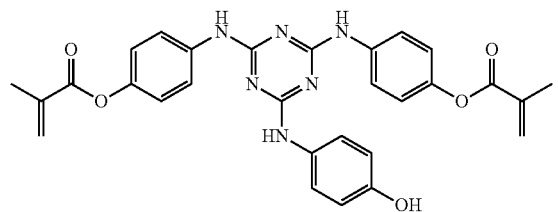
[Compound 12]
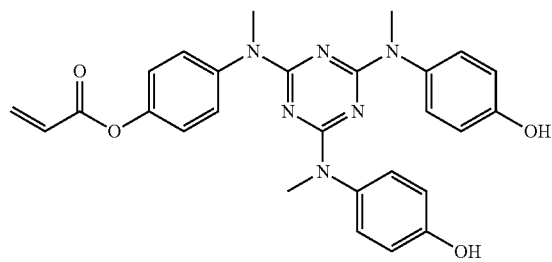
[Compound 13]
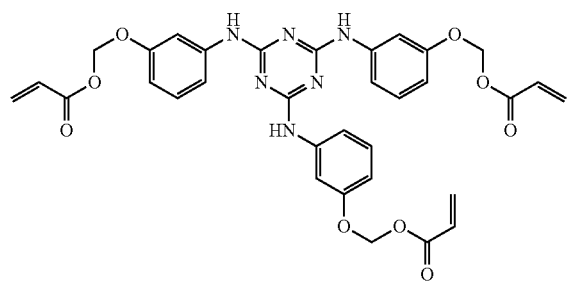
[Compound 14]
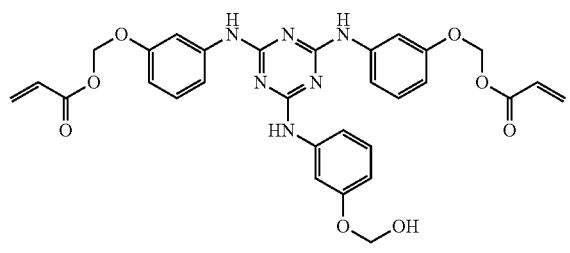
[Compound 15]
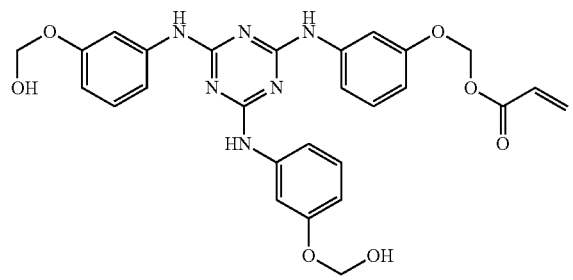
[Compound 16]
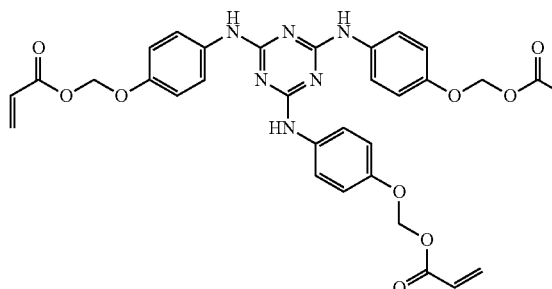

-continued
[Compound 17]
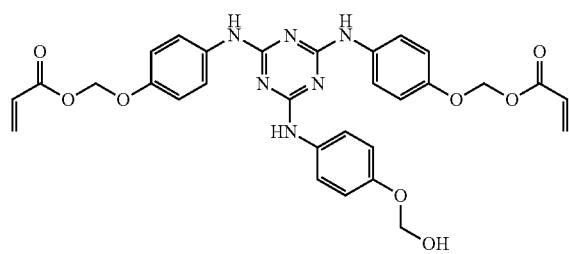
[Compound 18]
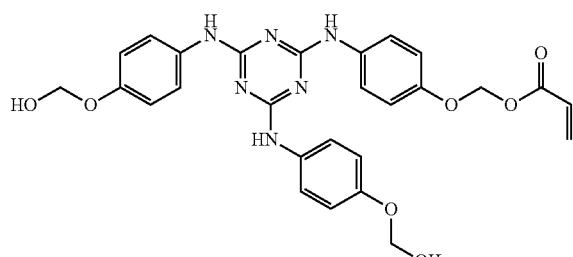
[Compound 19]
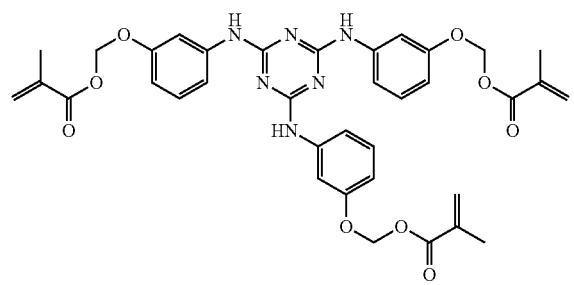
[Compound 20]
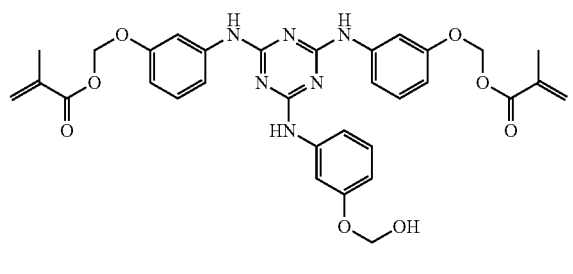
[Compound 21]
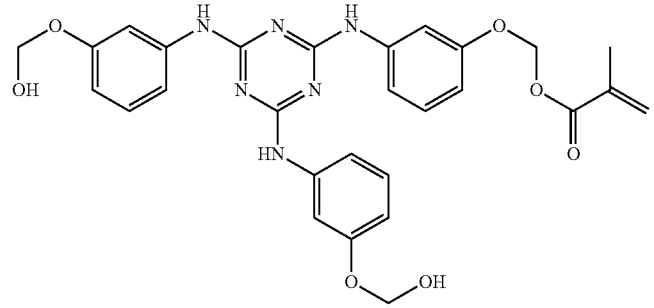
[Compound 22]
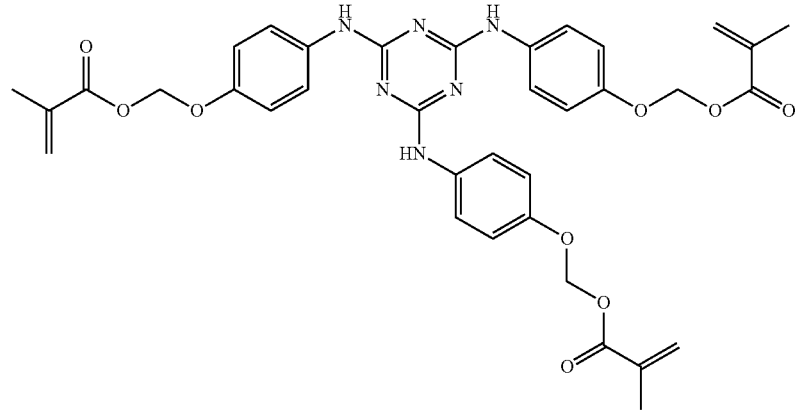
[Compound 23]
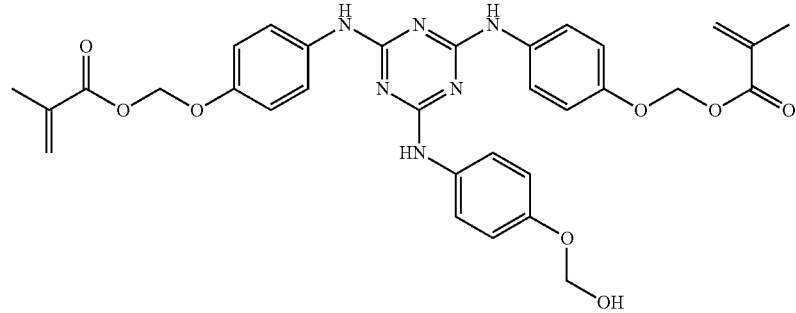

[Compound 24]
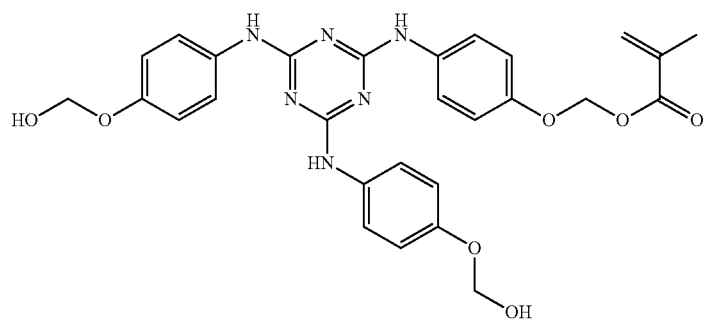
[Compound 25]
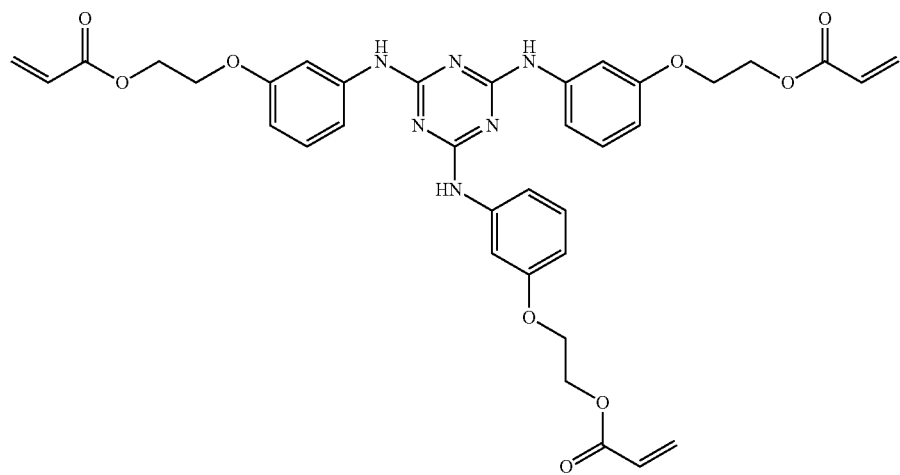
[Compound 26]
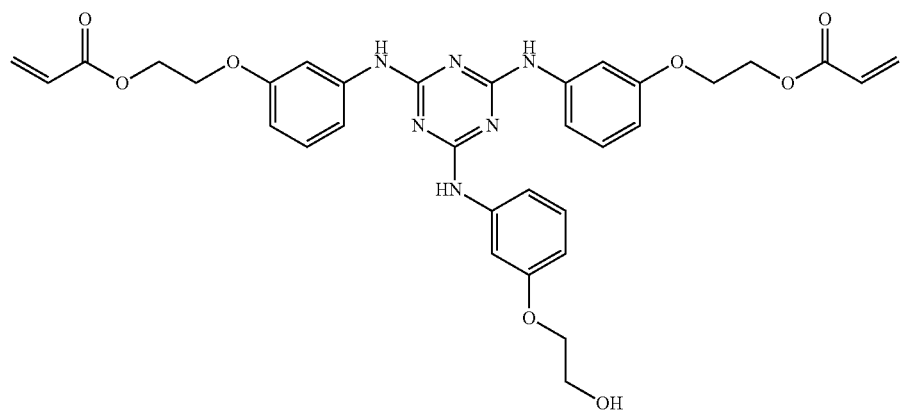
[Compound 27]
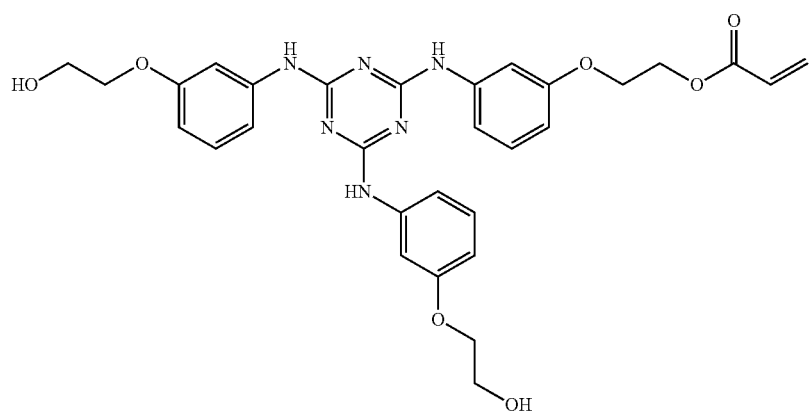

-continued
[Compound 28]
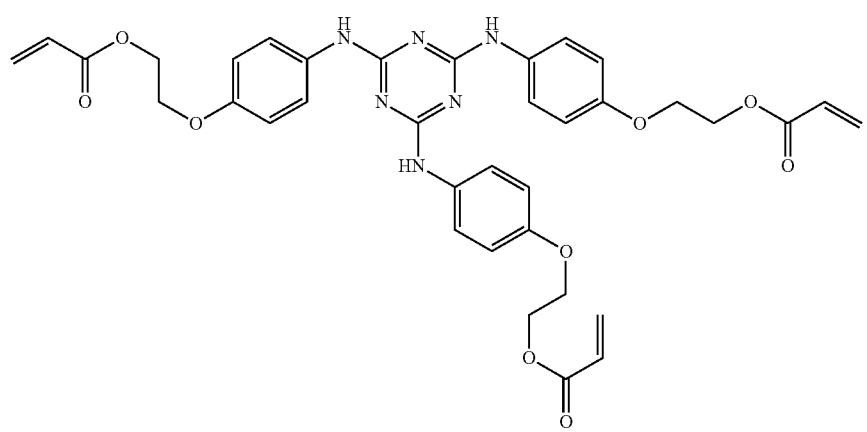
[Compound 29]
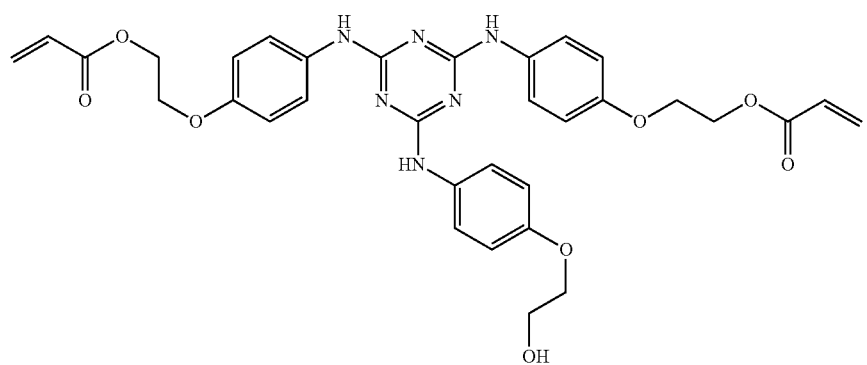
[Compound 30]
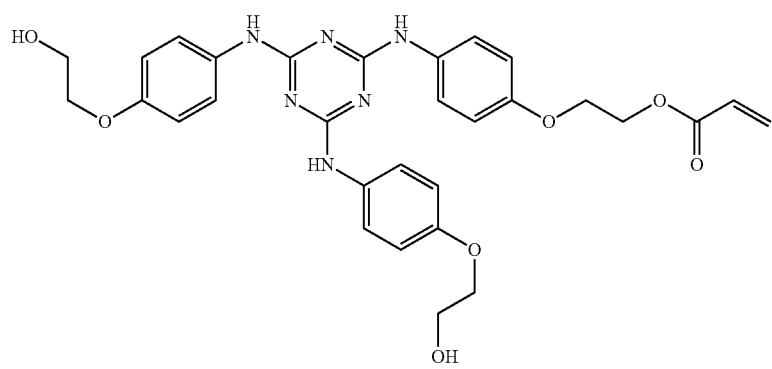
[Compound 31]
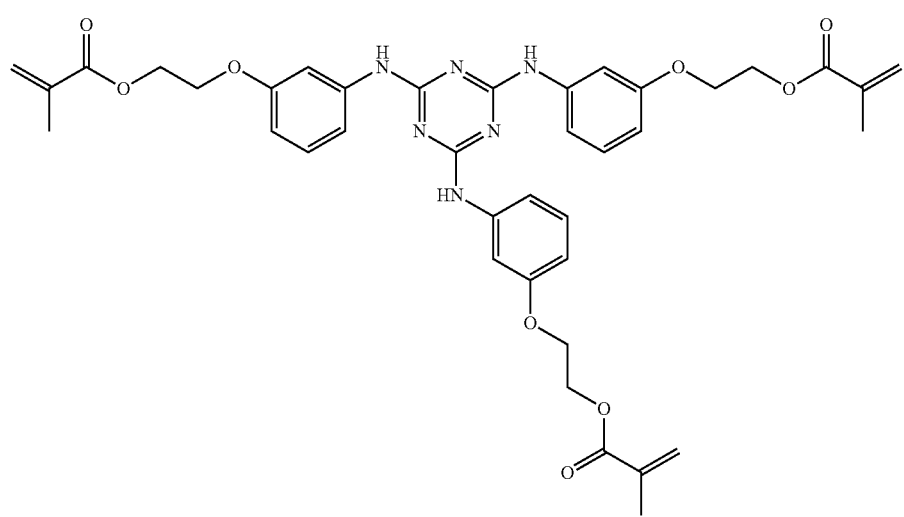

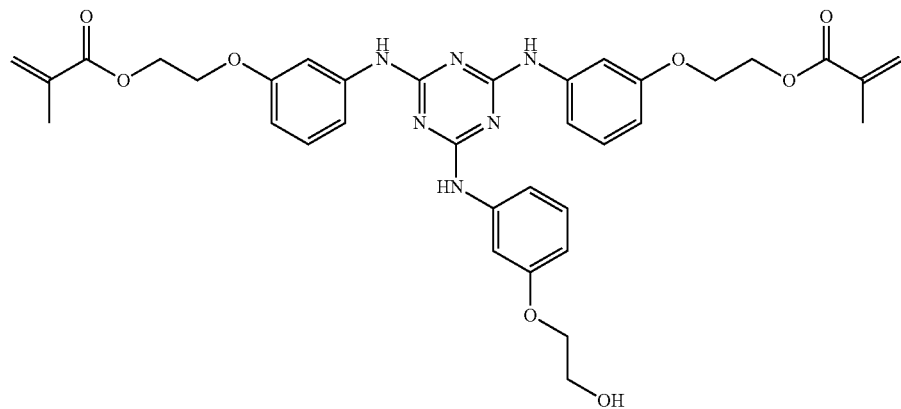
[Compound 32]
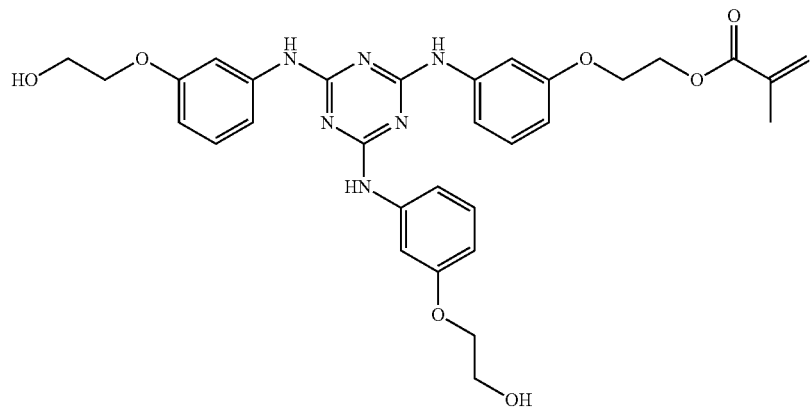
[Compound 33]
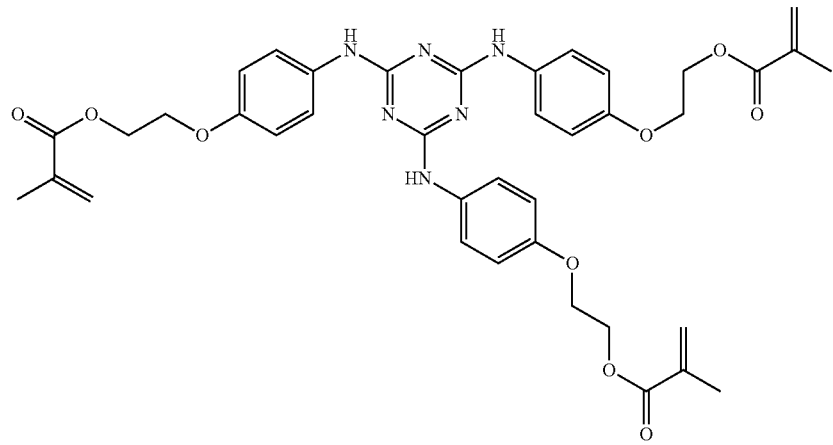
[Compound 34]
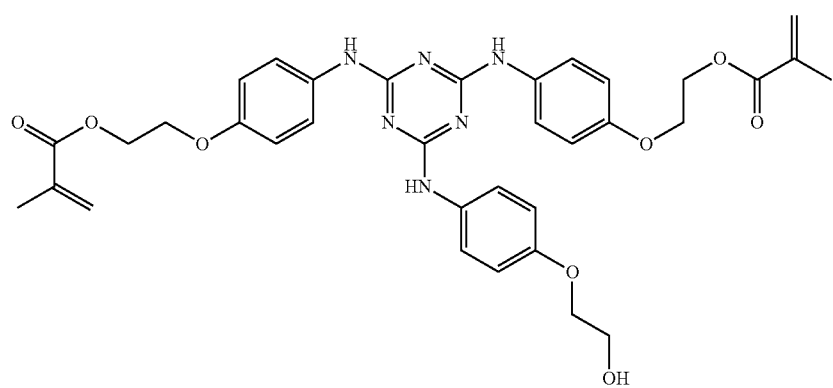
[Compound 35]

[Compound 36]
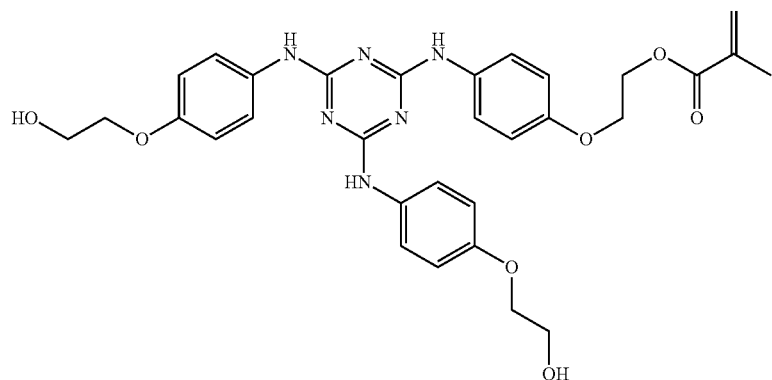
[Compound 37]
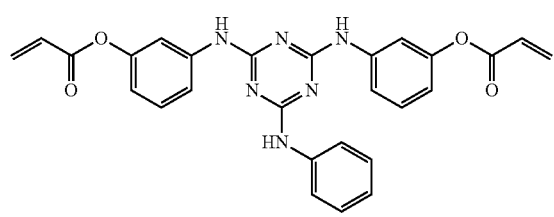
[Compound 38]
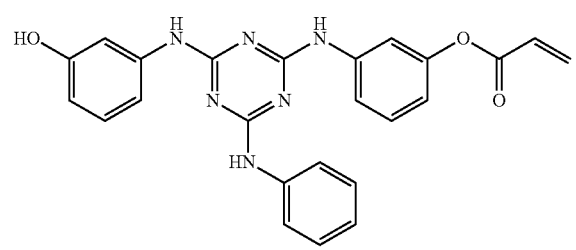
[Compound 39]
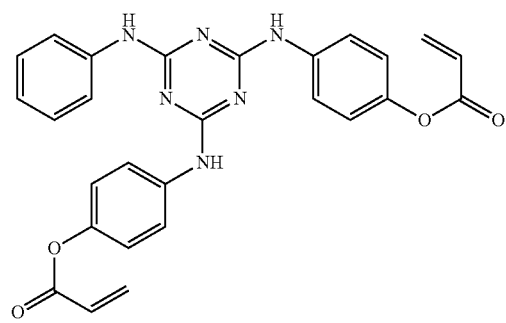
[Compound 40]
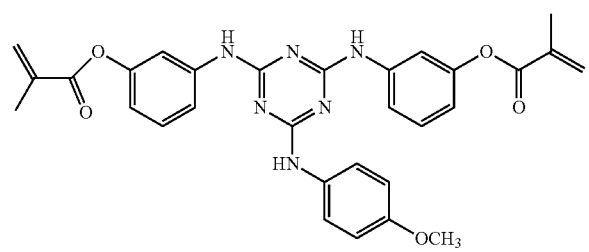
[Compound 41]
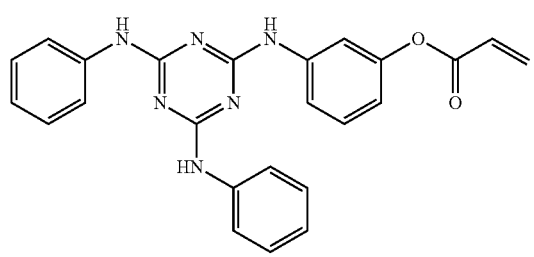
[Compound 42]
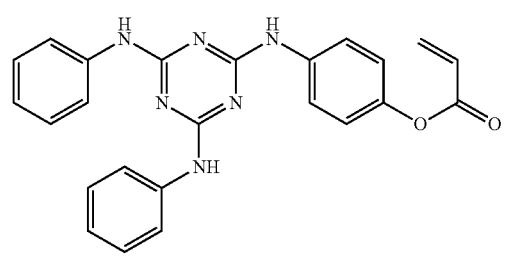
[Compound 43]
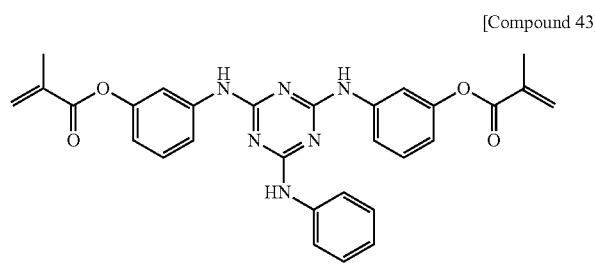
[Compound 44]
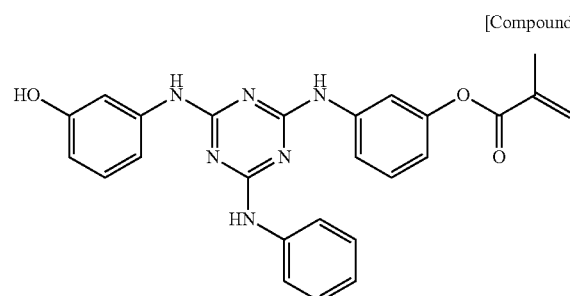

[Compound 45]
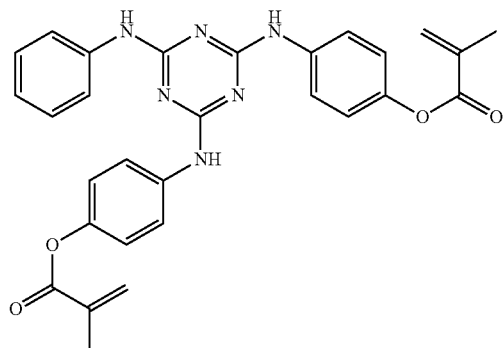
[Compound 46]
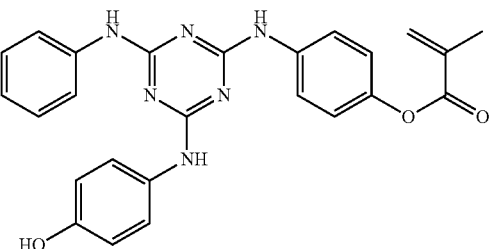
[Compound 47]
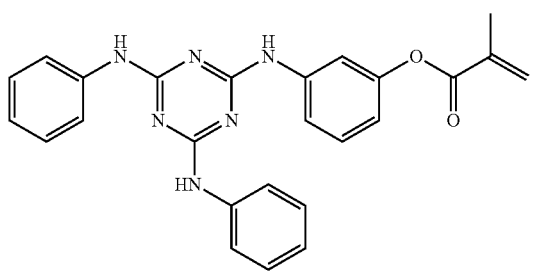
[Compound 48]
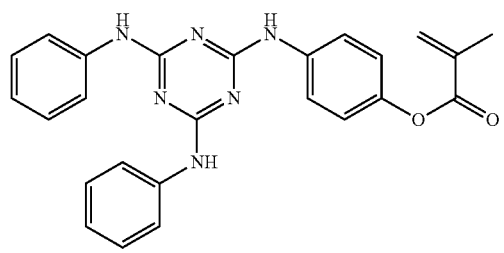
[Compound 49]
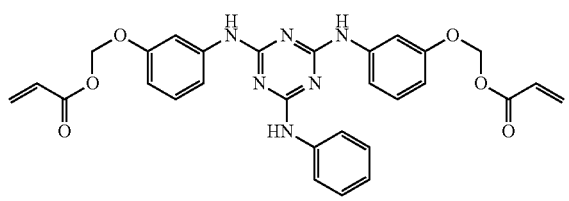
[Compound 50]
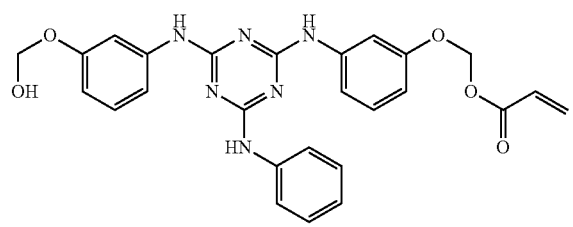
[Compound 51]
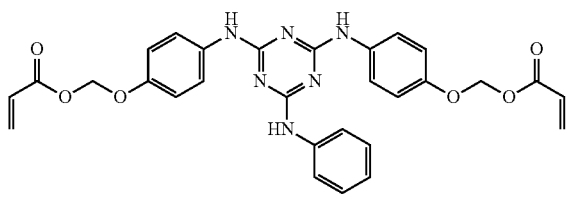
[Compound 52]
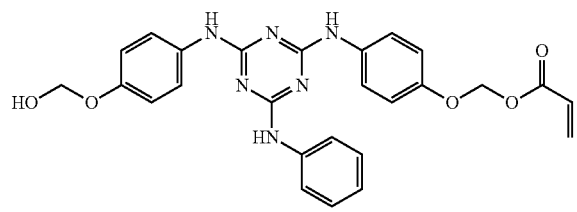
[Compound 53]
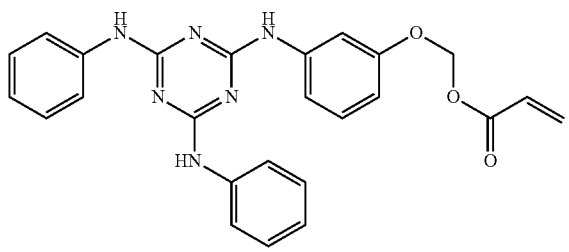
[Compound 54]
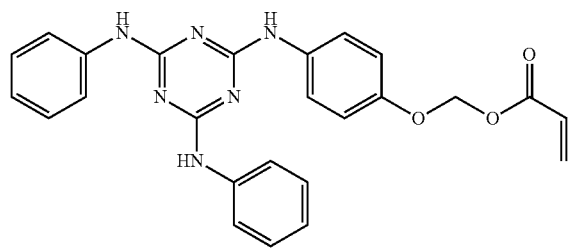

-continued
[Compound 55] [Compound 56]
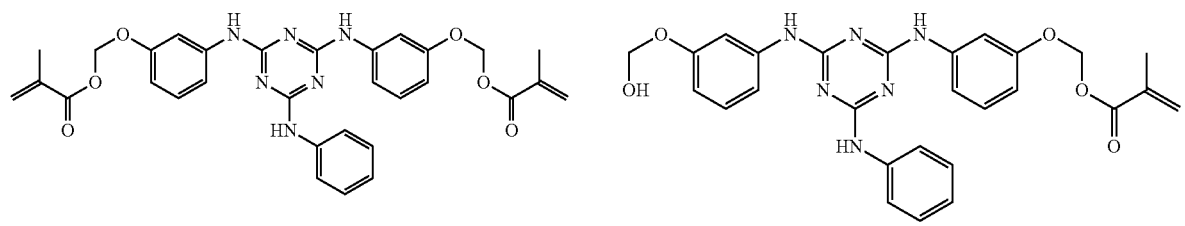
[Compound 57]
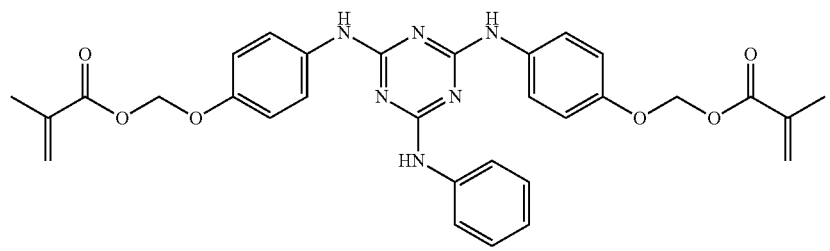
[Compound 58] [Compound 59]
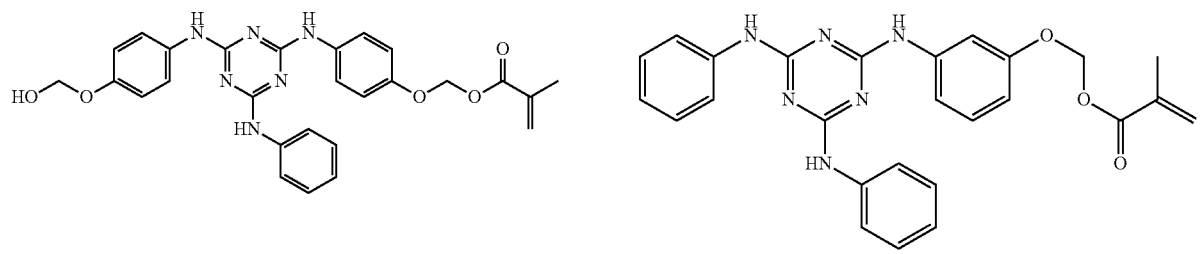
[Compound 60]
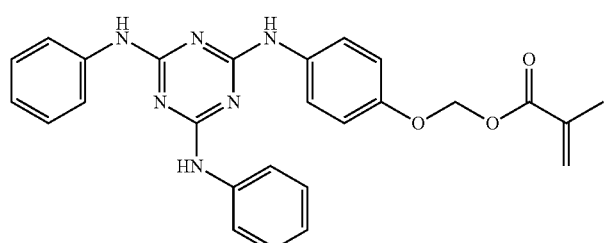
[Compound 61]
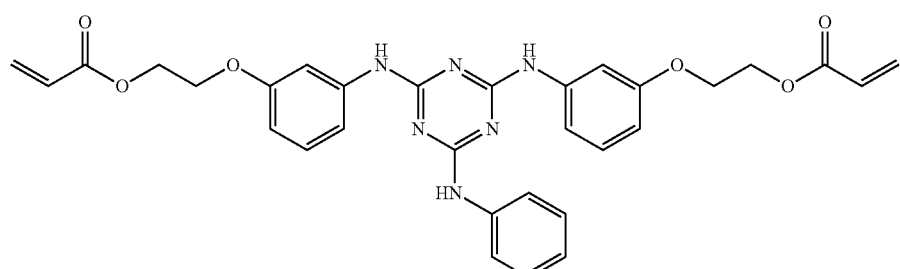
[Compound 62]
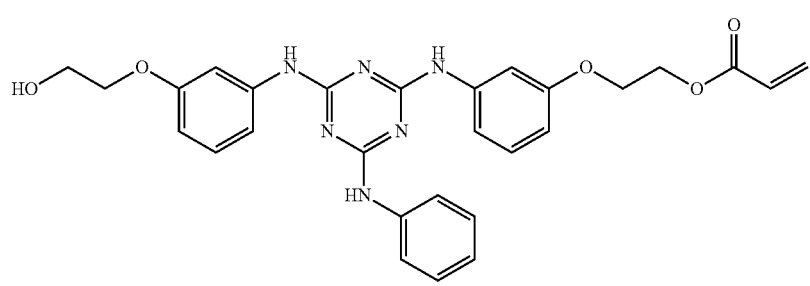

-continued
[Compound 63]
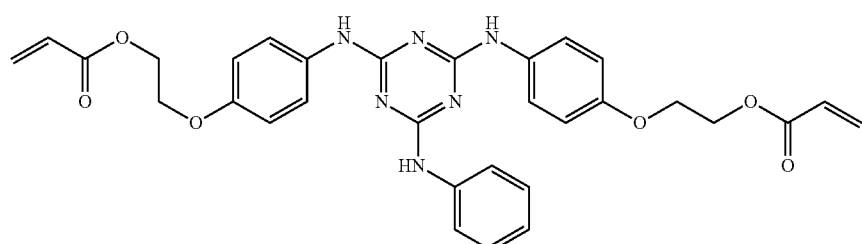
[Compound 64]
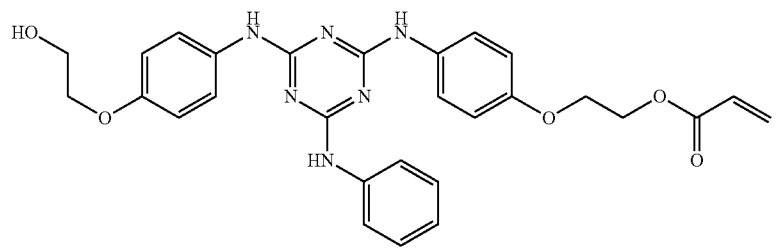
[Compound 65]  [Compound 66]
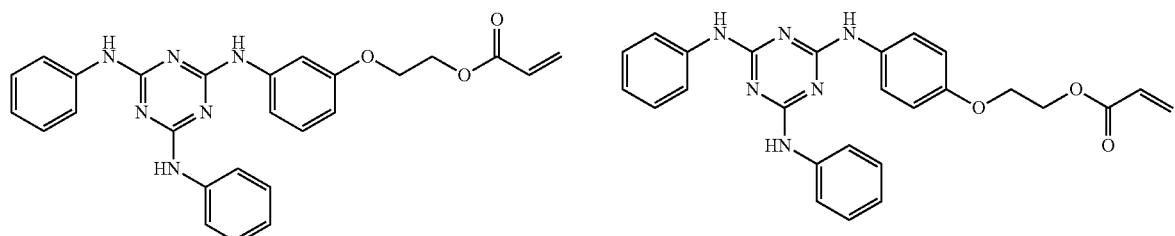
[Compound 67]
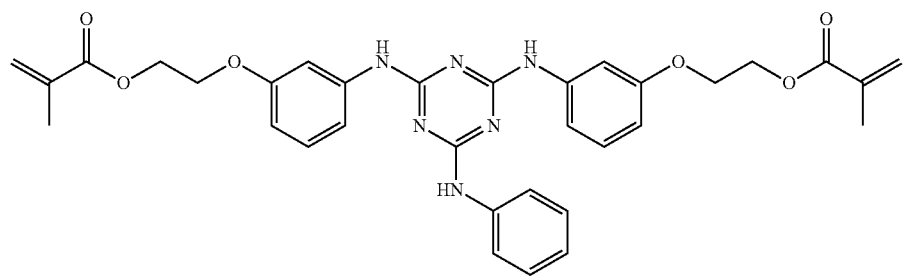
[Compound 68]
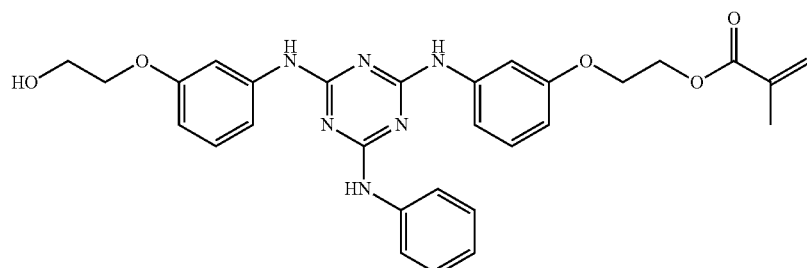
[Compound 69]
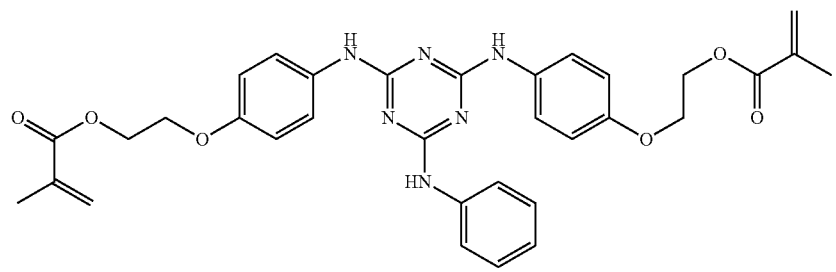

[Compound 70]
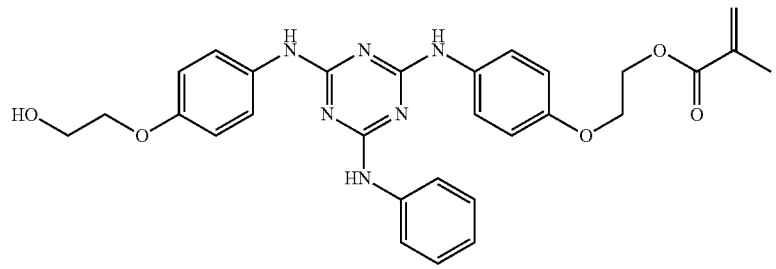
[Compound 71]
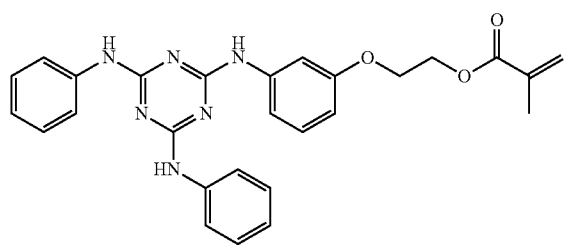
[Compound 72]
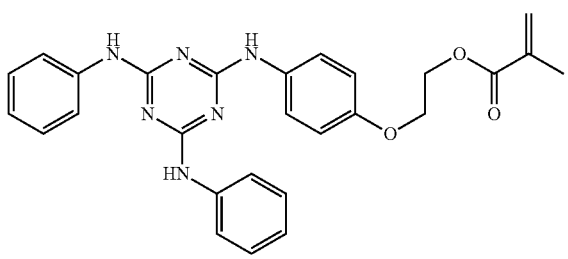
[Compound 89]
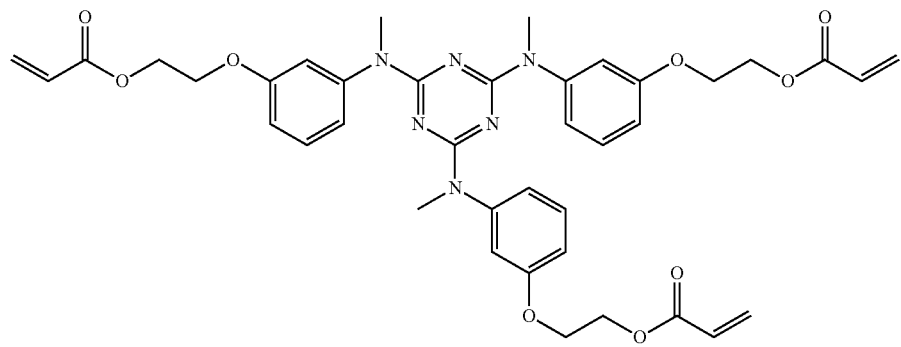
[Compound 90]
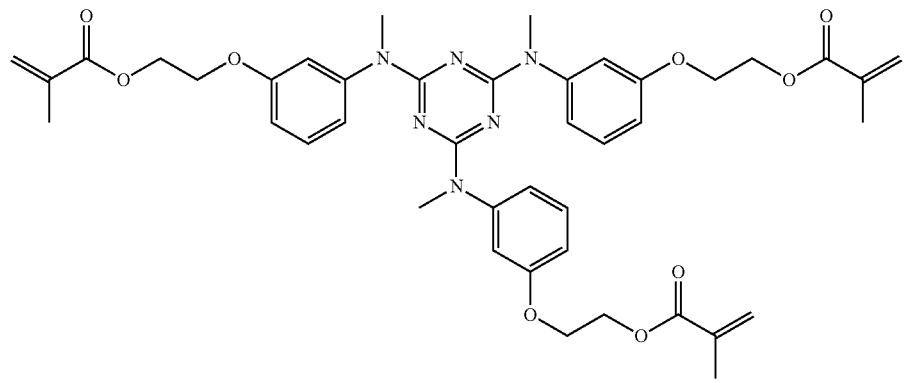

[Compound 91]
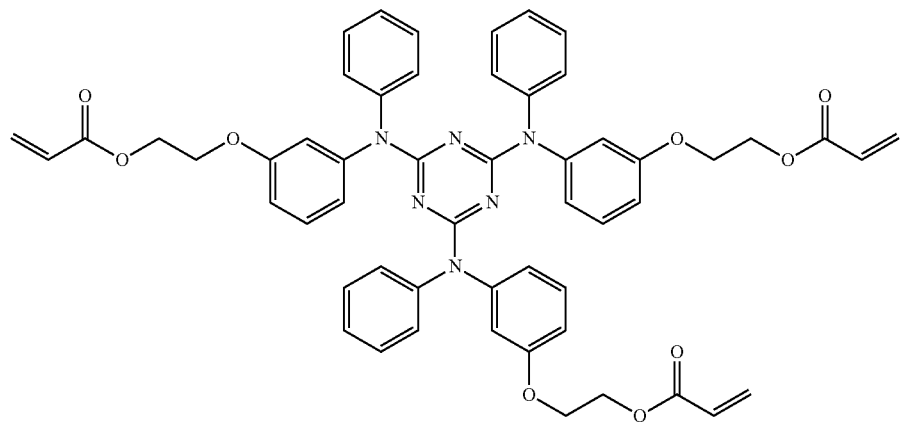
[Compound 92]
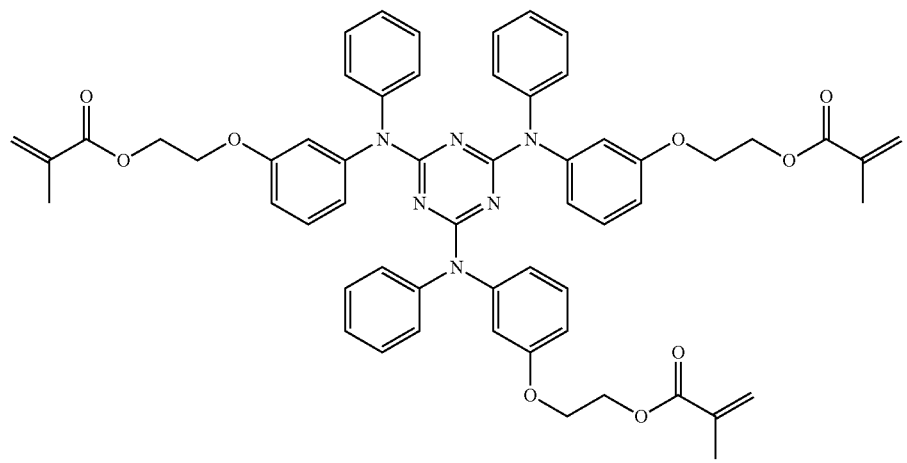
[Compound 93]
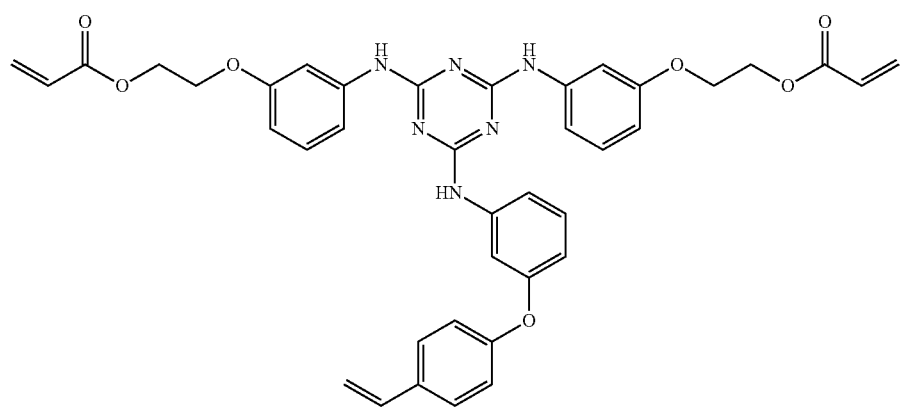
[Compound 94]
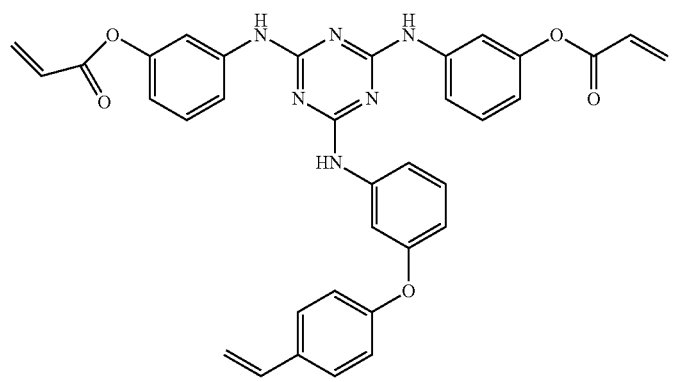

-continued
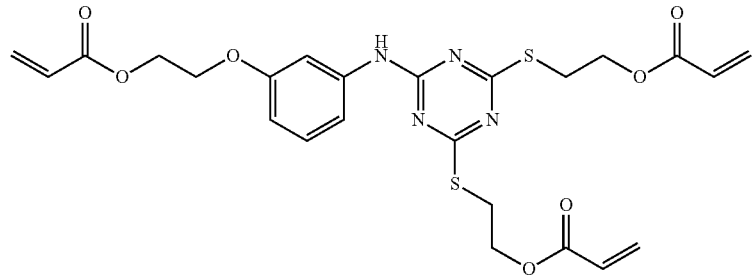
[Compound 95]
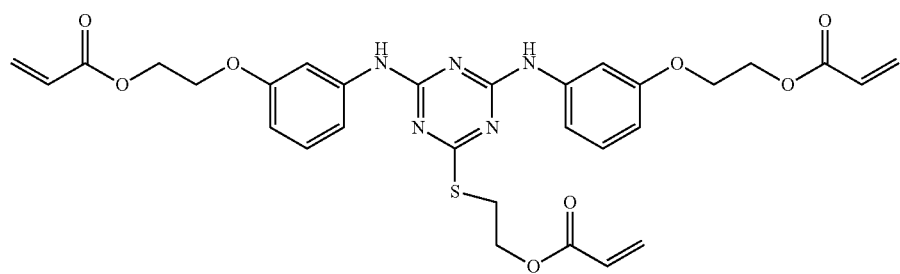
[Compound 96]
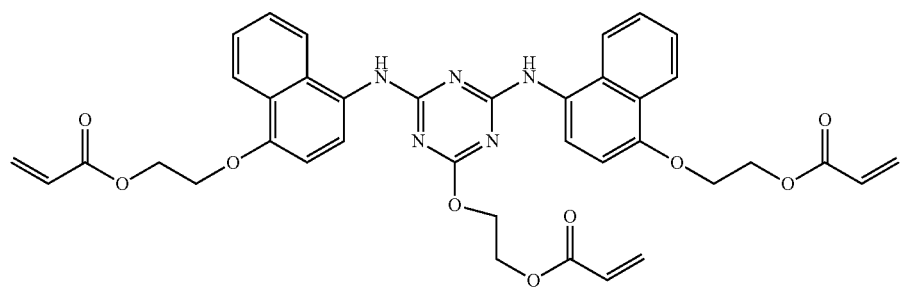
[Compound 97]
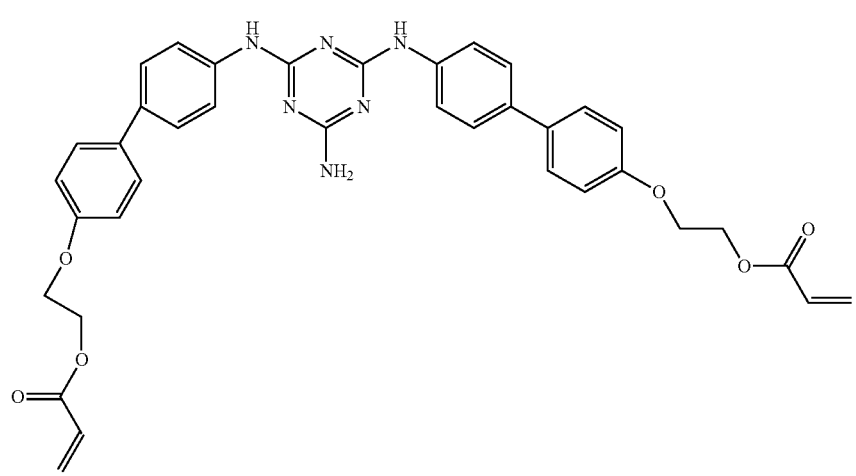
[Compound 98]

[Compound 103]
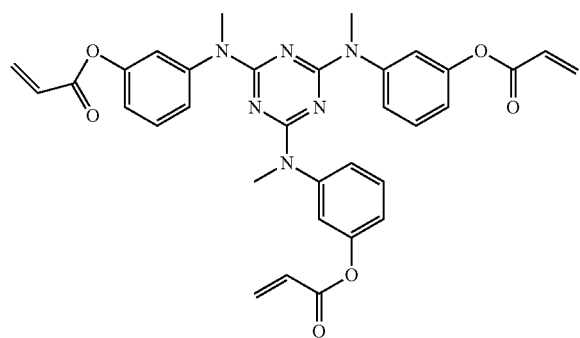
[Compound 104]
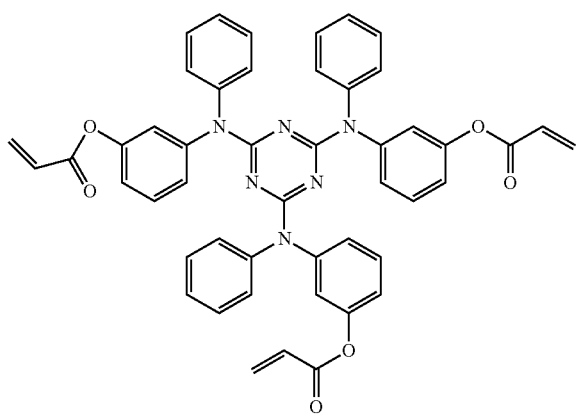
[Compound 105]
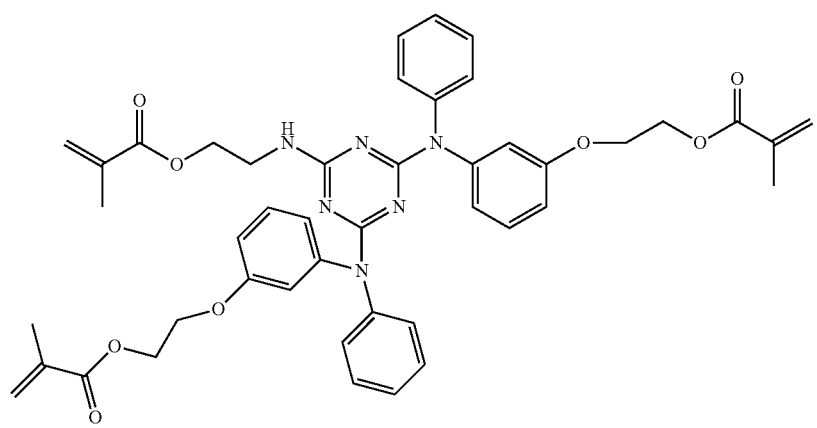
[Compound 106]
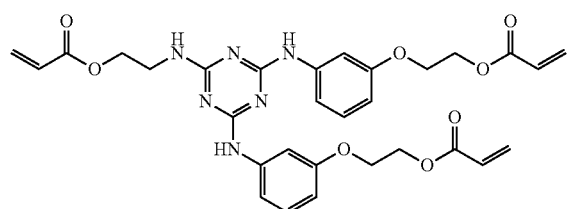
[Compound 107]
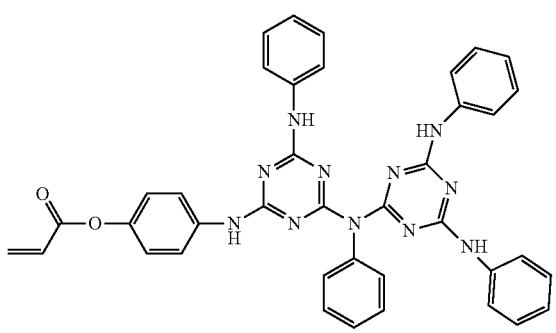
[Compound 108]
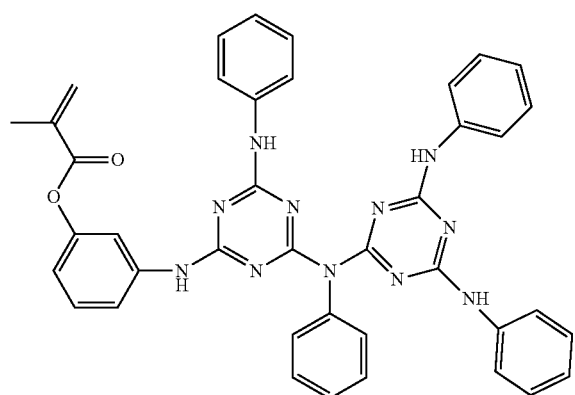

[Compound 109]
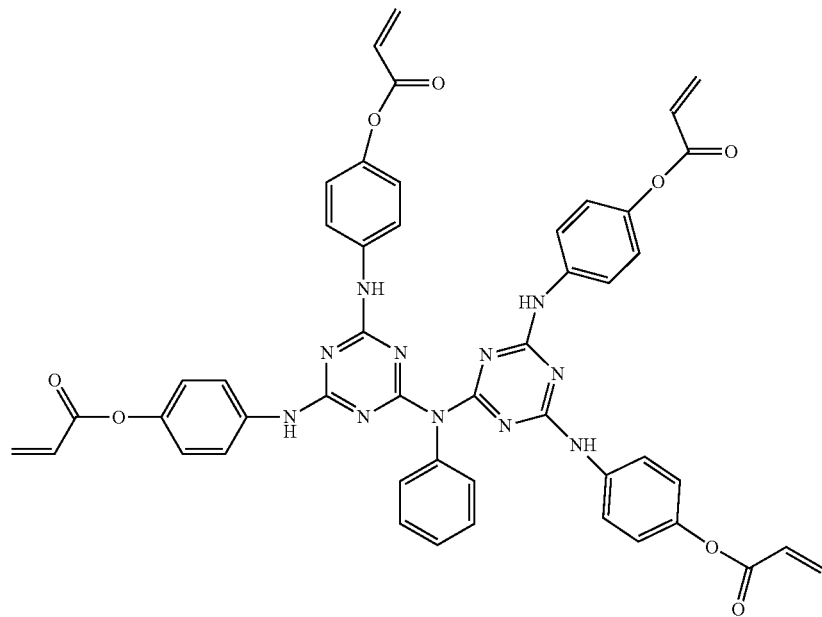
[Compound 110]
[Compound 111]
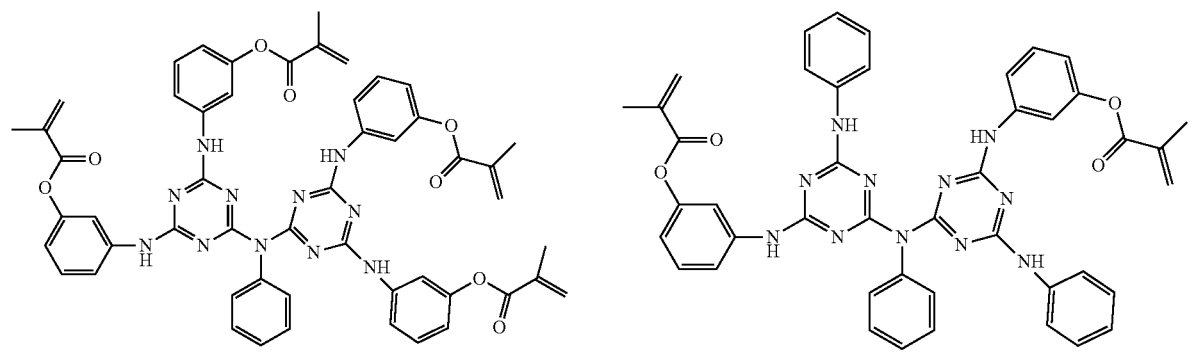
[Compound 112]
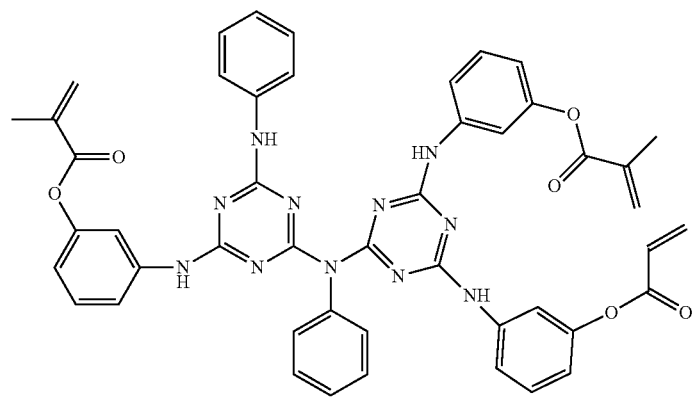

[Compound 113]
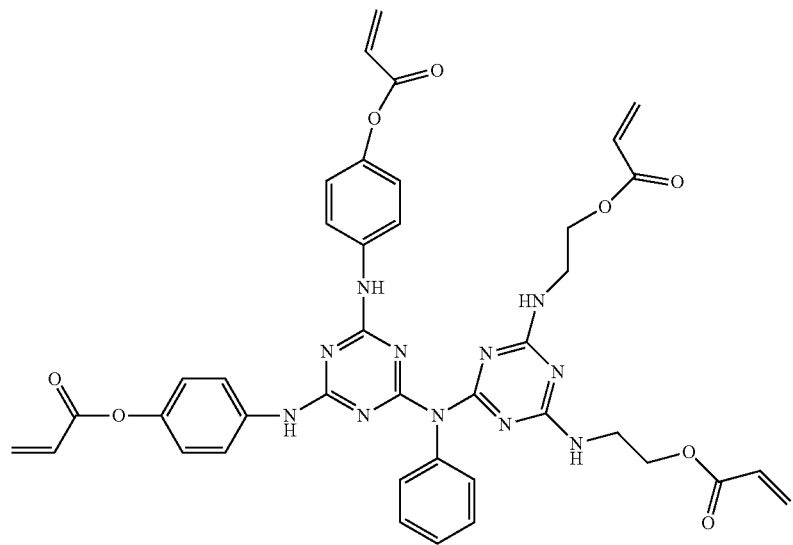
[Compound 114]
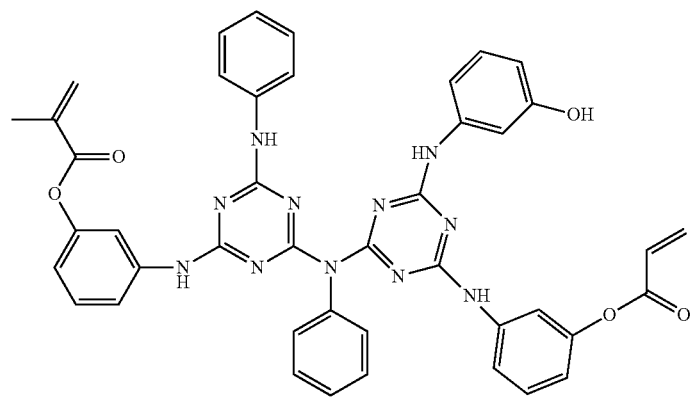
[Compound 115]
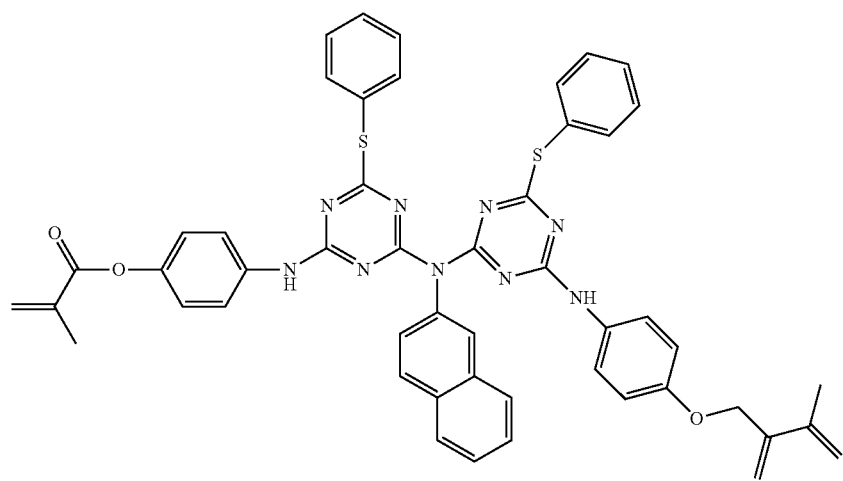

[Compound 116]
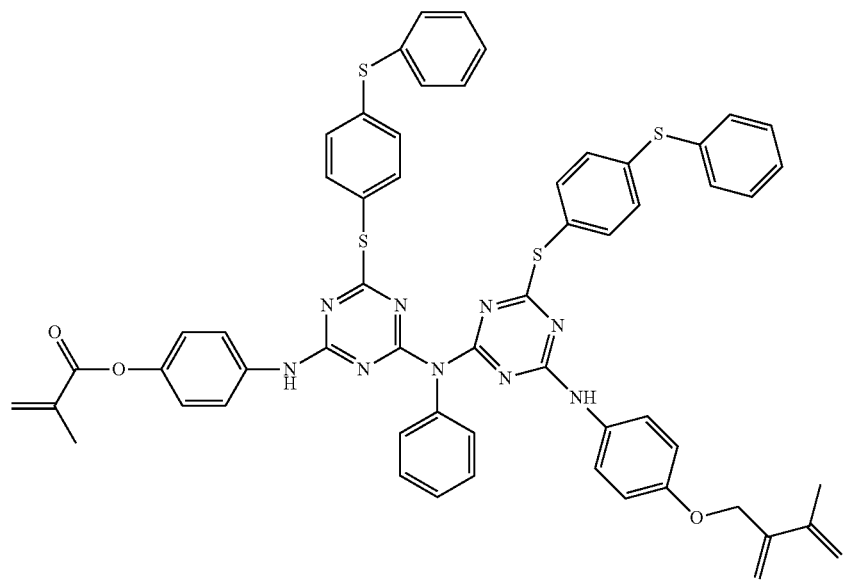
[Compound 117]
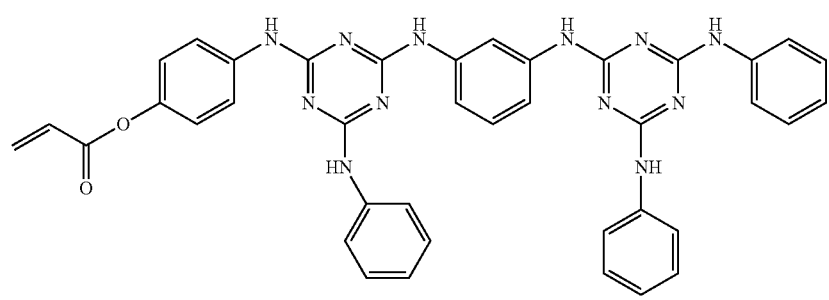
[Compound 118]
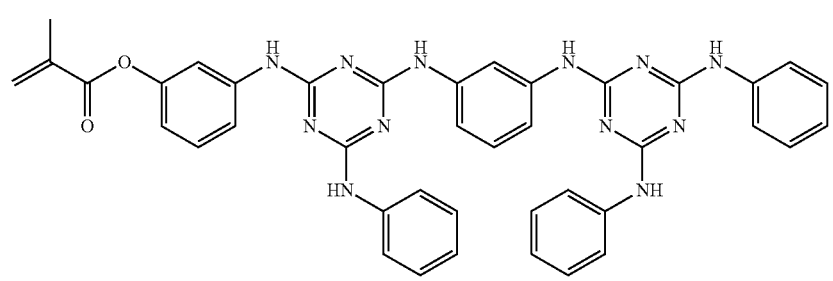
[Compound 119]
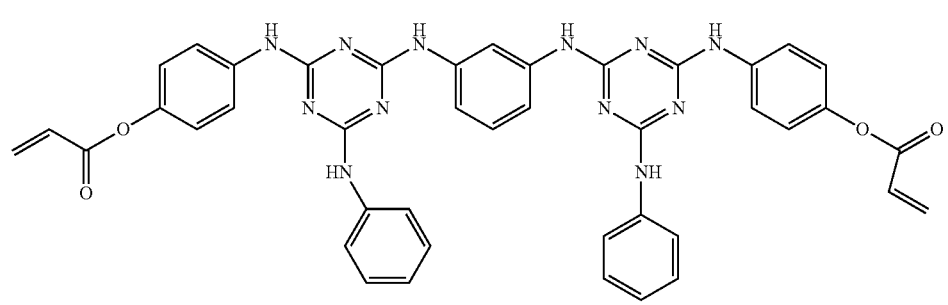

[Compound 120]
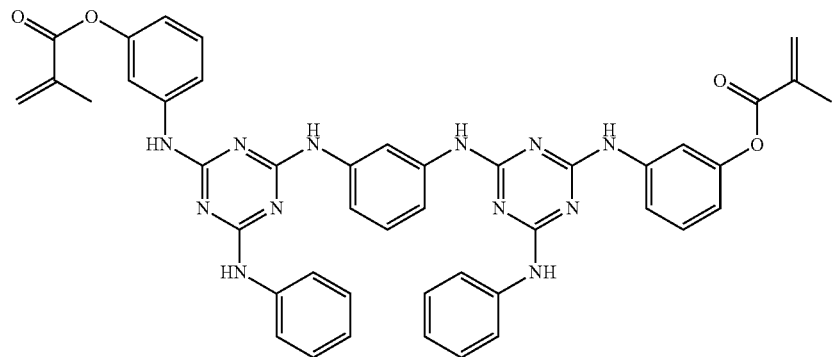
[Compound 121]
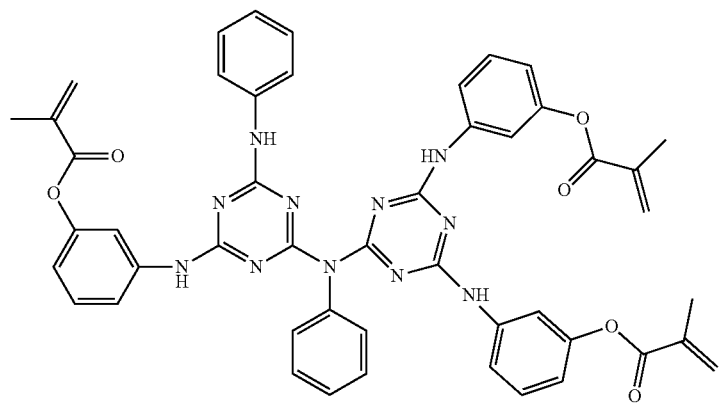
[Compound 122]
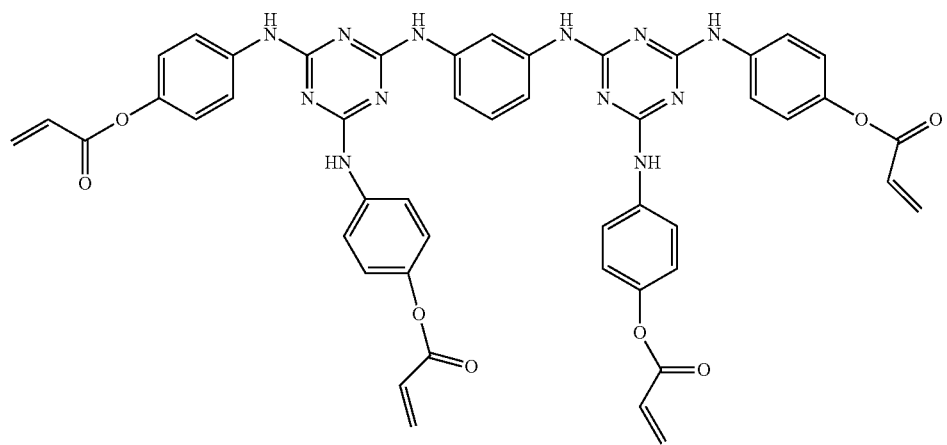

[Compound 123]
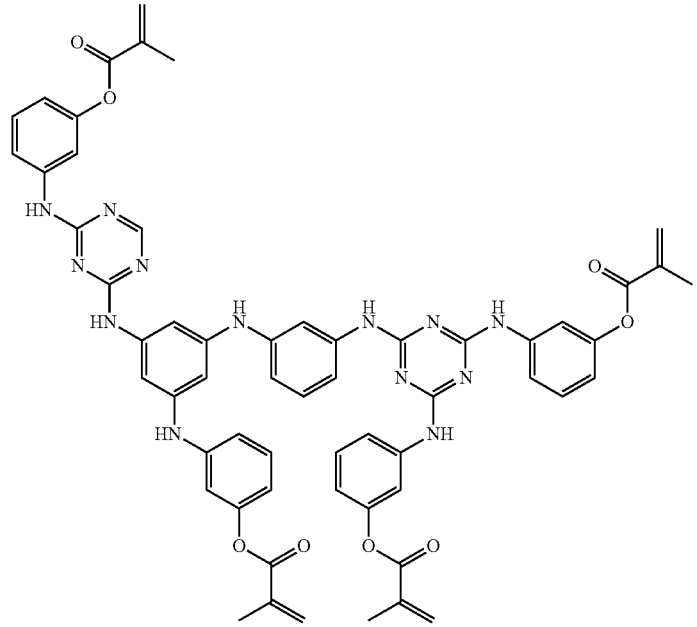
[Compound 124]
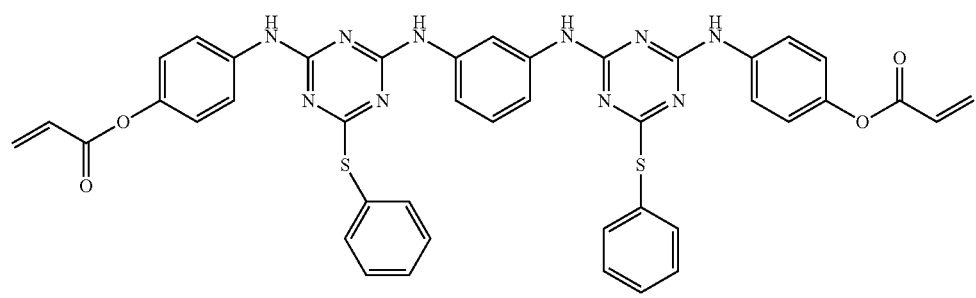
[Compound 125]
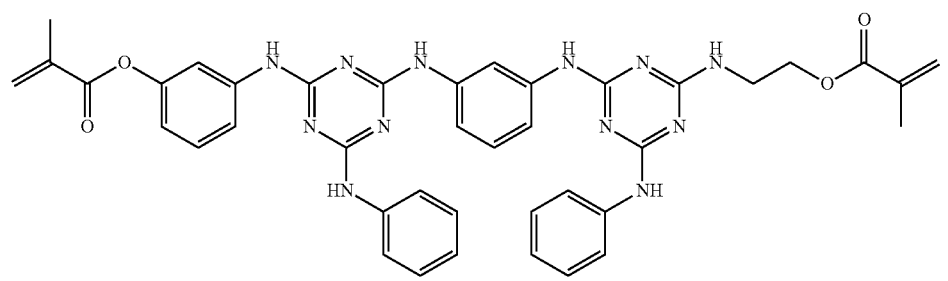
[Compound 126]
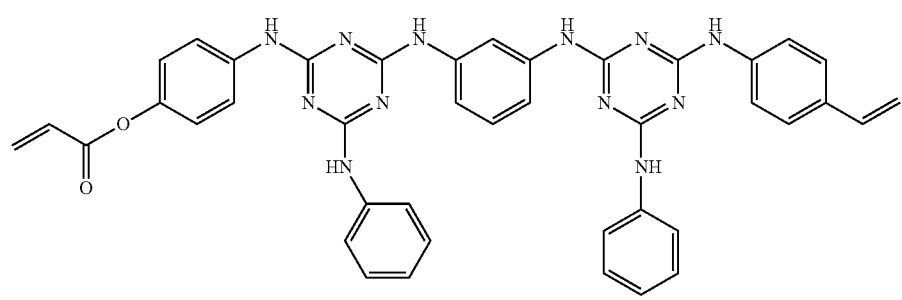

-continued
[Compound 127]
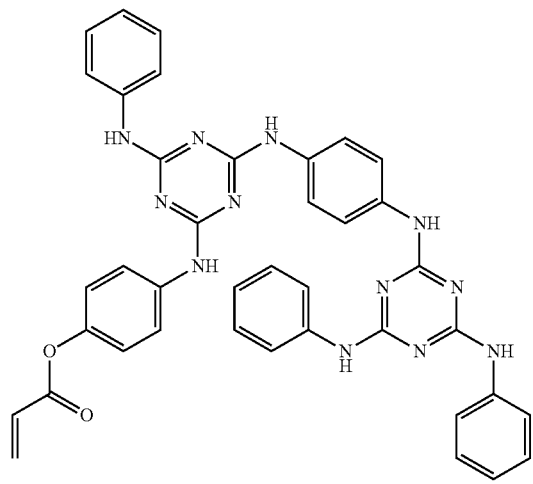
[Compound 128]
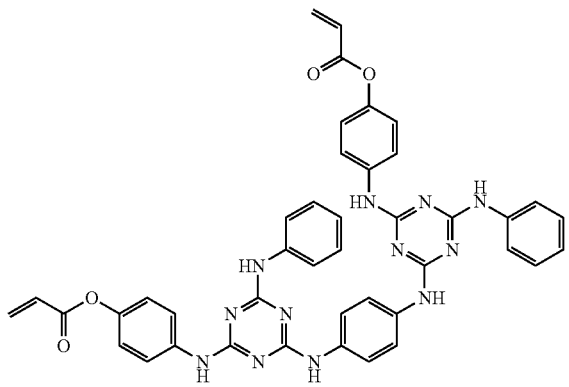
[Compound 129]
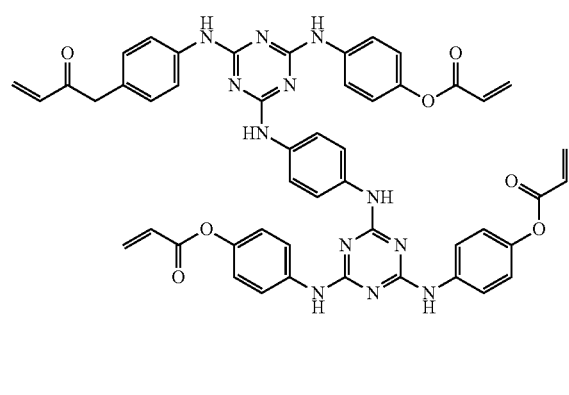
[Compound 130]
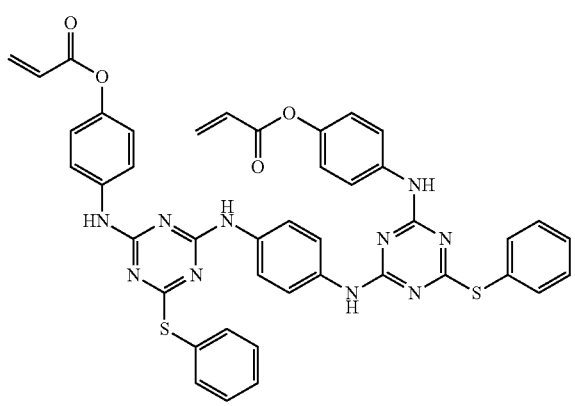
[Compound 131]
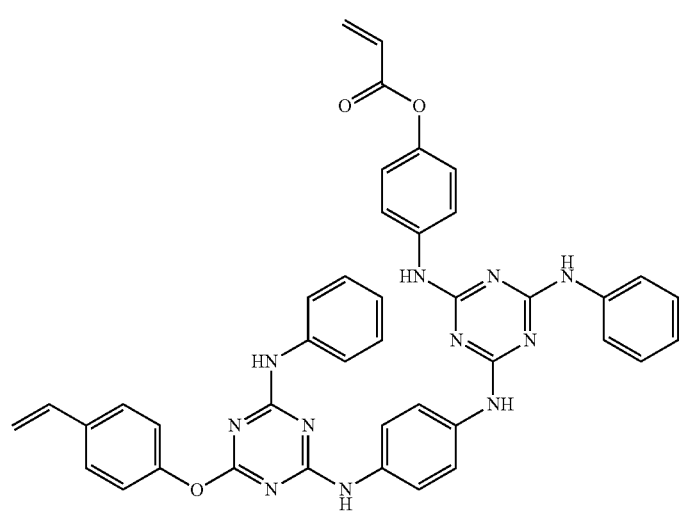

-continued

[Compound 132]
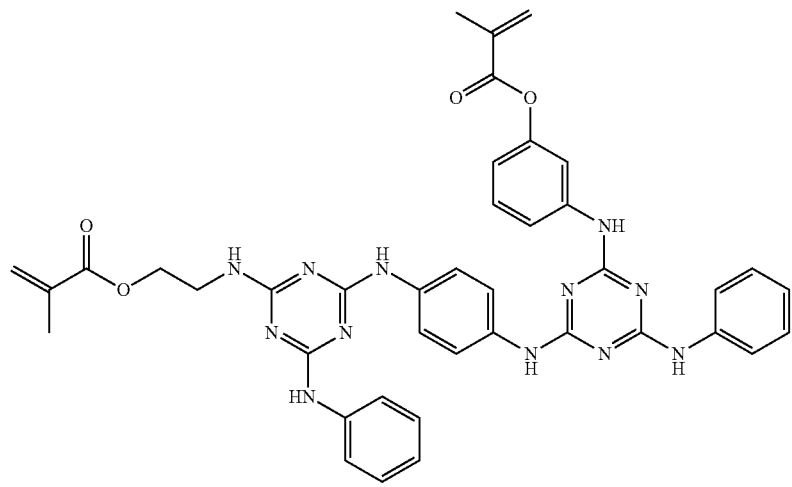

[Compound 133]
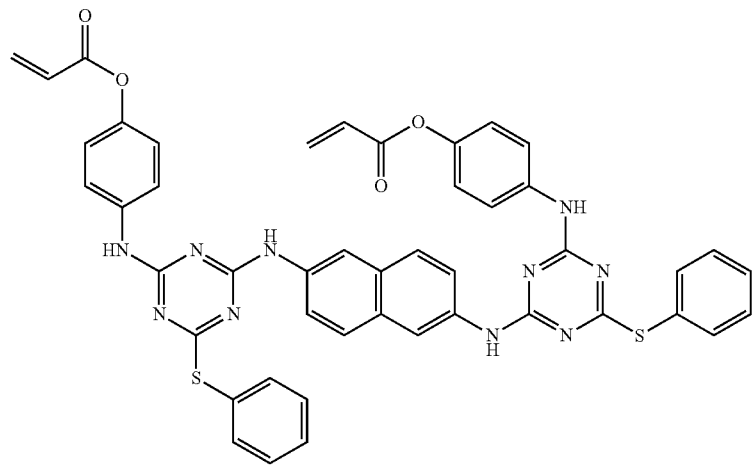

[Compound 134]
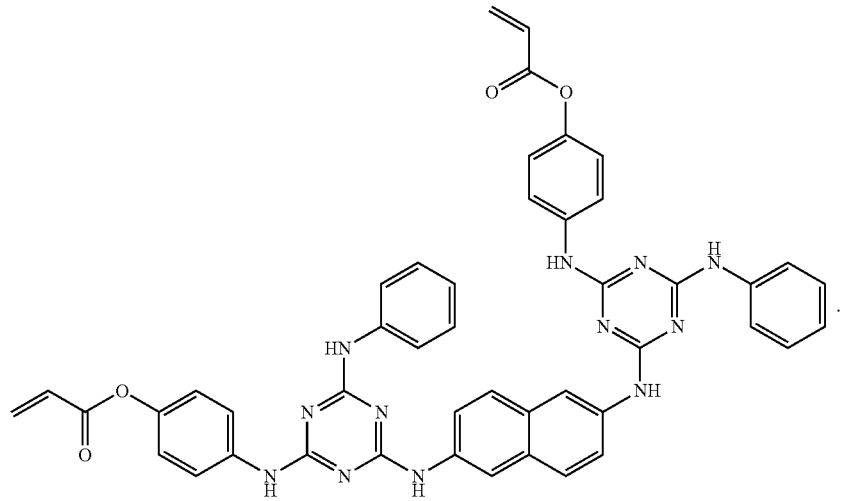

19. A photosensitive composition comprising the compound of claim 1.

20. The photosensitive composition of claim 19, further comprising a photoinitiator or a photopolymerizable monomer.

21. An optical material, obtained by polymerizing the photosensitive composition of claim 19.

22. A photosensitive composition, comprising 1 to 95 parts by weight of the compound of claim 1, 0 to 90 parts by weight of a photopolymerizable compound, and 0.1 to 20 parts by weight of a photoinitiator.

23. The photosensitive composition of claim 22, wherein the photosensitive composition is used for preparing any one selected from a prism sheet, a microlens, a DBEF film, a coating material for LCD, a coating material for an organic light emitting diode (OLED), an optical lens, and a multi-focal lens.

* * * * *